United States Patent
Rader et al.

(10) Patent No.: US 11,834,501 B2
(45) Date of Patent: Dec. 5, 2023

(54) ROR2 ANTIBODY COMPOSITIONS AND RELATED METHODS

(71) Applicant: University of Florida Research Foundation, Incorporated, Gainesville, FL (US)

(72) Inventors: Christoph Rader, Jupiter, FL (US); Haiyong Peng, Jupiter, FL (US); Xiuling Li, Jupiter, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 133 days.

(21) Appl. No.: 17/382,948

(22) Filed: Jul. 22, 2021

(65) Prior Publication Data
US 2021/0347892 A1 Nov. 11, 2021

Related U.S. Application Data

(62) Division of application No. 16/071,361, filed as application No. PCT/US2017/014370 on Jan. 20, 2017, now Pat. No. 11,078,273.

(60) Provisional application No. 62/280,834, filed on Jan. 20, 2016.

(51) Int. Cl.
| | |
|---|---|
| *C07K 16/28* | (2006.01) |
| *A61K 47/68* | (2017.01) |
| *A61P 35/00* | (2006.01) |
| *A61K 39/00* | (2006.01) |

(52) U.S. Cl.
CPC ...... *C07K 16/2803* (2013.01); *A61K 47/6809* (2017.08); *A61K 47/6849* (2017.08); *A61K 47/6889* (2017.08); *A61P 35/00* (2018.01); *A61K 2039/505* (2013.01); *C07K 2317/24* (2013.01); *C07K 2317/33* (2013.01); *C07K 2317/73* (2013.01); *C07K 2317/90* (2013.01); *C07K 2317/92* (2013.01); *C07K 2319/00* (2013.01)

(58) Field of Classification Search
CPC ............ C07K 16/2803; C07K 2317/92; C07K 2317/33; C07K 2317/73; A61K 2039/505; A61K 47/6849; A61P 35/00
See application file for complete search history.

(56) References Cited

U.S. PATENT DOCUMENTS 11,078,273 B2  8/2021  Rader et al.

FOREIGN PATENT DOCUMENTS

| WO | WO-2013/103637 A1 | 7/2013 |
| WO | WO-2015/171938 A1 | 11/2015 |
| WO | WO-2016/142768 A1 | 9/2016 |
| WO | WO-2016/172726 A1 | 10/2016 |

OTHER PUBLICATIONS

International Search Report and Written Opinion for International Application No. PCT/US2017/014370, dated Apr. 3, 2017, (13 pages), European Patent Office, Rijswijk, Netherlands.
Communication Pursuant to Article 94(3) EPC for European Patent Application No. 17702284.5, dated Jun. 25, 2019, (5 pages), European Patent Office, Rijswijk, Netherlands.
Abcam, "Anti-ROR2 Antibody (6F2D10) ab201962," Abcam Catalog, Mar. 1, 2015, pp. 1-3.
Debebe et al. "ROR2 as a Therapeutic Target In Cancer," *Pharmacology & Therapeutics*, vol. 150, Jun. 1, 2015, pp. 143-148, DOI: 10.1016/j.pharmthera.2015.01.010.
R&D Systems. "Human ROR2 Antibody," Catalog No. MAB2064, R&D Catalog, Oct. 13, 2015, p. 1.
Rebagay, Guilly et al. "ROR1 and ROR2 In Human Malignancies: Potentials for Targeted Therapy," *Frontiers In Oncology*, vol. 2, No. 34, Apr. 18, 2012, pp. 1-8, DOI: 10.3389/fonc.2012.00034.
Rudikoff, Stuart et al. "Single Amino Acid Substitution Altering Antigen-Binding Specificity," *Proceedings of the National Academy of Sciences*, vol. 79, No. 6, Mar. 1982, pp. 1979-1983.
Vajdos, Felix F. et al. "Comprehensive Functional Maps of the Antigen-Binding Site of an Anti-ErbB2 Antibody Obtained With Shotgun Scanning Mutagenesis," *Journal of Molecular Biology*, vol. 320, No. 2, Jul. 5, 2002, pp. 415-428, DOI: 10.1016/S0022-2836(02)00264-4.
U.S. Appl. No. 16/071,361, filed Jul. 19, 2018, U.S. Pat. No. 11,078,273, Issued.
PCT/US2017/014370, Jan. 20, 2017, WO 2017/127702, Expired.
U.S. Appl. No. 62/280,834, filed Jan. 20, 2016, Expired.

*Primary Examiner* — Ruixiang Li
(74) *Attorney, Agent, or Firm* — Alston & Bird LLP

(57) ABSTRACT

The invention provides antibodies, antibody fragments or antigen-binding fragments, as well as related antibody drug conjugates (ADCs) and chimeric antigen receptors (CARs), that specifically recognize human ROR2. Also provided in the invention are methods of using such antibodies in various diagnostic and therapeutic applications.

10 Claims, 29 Drawing Sheets
Specification includes a Sequence Listing.

ROR2 mAbs

| Vκ | FR1 | CDR1 | FR2 | CDR2 | FR3 | CDR3 | FR4 |
|---|---|---|---|---|---|---|---|
| | 1 23 | | 35 | 49 | 57 88 | | 98 107 |
| XBR2-401 | DPMLTQTPSSTSAVGDTVTIKC | QASQSISS-DLS | WYQQKPGQRPKLLIY | QASTLAS | GVPSRFKGSGYGTGYTLTISGVQREDAATYYC | LGGYADASYRTIA | FGGGTKLEIK |
| XBR2-416 | AQVLTQTPSSTSAAVGGTVTIKC | QASQSISSSDLS | WYQQKPGQPPKLLIY | ATSYLAS | GVPSRFKGSGSGTEYTLTISGVQREDAATYYC | LGGYPNTSYRSA | FGGGTKVEIK |
| XBR2-327 | DPVLTQTPSSTSAAVGGTVTIKC | QASQSISS-YLS | WYQQKPGQPPKLLIY | GASKLAS | GVPSRFSGSGSGTDYTLTISGVQREDAATYYC | LGGYASASYRTIA | FGGGTKLEIK |
| XBR2-TOP9 | DVVMTQTPSSVSAAVGGTVAINC | QASQNIGP-WLS | WYQQKPGQPPKLLIY | AASTLAS | GVPSRFKGSGSGTDYTLTISGVQREDAATYYC | LGWHSWSDDGWA | FGAGTNVEIK |
| ERR2-308 | DPMLTQTPSSTSAVGGTVTIKC | QASQSITS-WLS | WYQQKPGQPPKLLIY | GASHLAS | GVPSRFKGSGSGTEYTLTISGIQREDAATYYC | LGGYSNSDIV-- | FGGGTELEIL |
| ERR2-316 | DPVLTQTPSSVSEPVGGTVTIKC | QASQSISN-ALA | WYQQKPGQPPKLLIY | KASTPAS | GVPSRFKGSRGTEYTLTISGVQREDAATYYC | LGFSVVSNDGWA | FGAGTNVEIK |
| ERR2-317 | DPVLTQTPSSTSAAVGGTVTIKC | QASQSISS-YLS | WYQQKPGQPPRQLIY | AASTLAS | GVPSRFKGSGSGTETLTISGVQREDAATYYC | LGGYASASYQTA | FGGGTKVEIK |
| ERR2-TOP2 | DVVMTQTPSSVSAAVGGTVSLKC | QASQSITS-WLS | WYQQKPGQPPKLLIY | GASHLAS | GVPSRFKGSGYGTEFTLTISGIQREDAATYYC | LGGTLSASYQTA | FGGGTKVEIK |

| Vλ | FR1 | CDR1 | FR2 | CDR2 | FR3 | CDR3 | FR4 |
|---|---|---|---|---|---|---|---|
| | 1 23 | | 35 | | 57 88 | | 98 107 |
| XBR2-433 | SPVLTQPASVQVMLGQTVSLIC | TADTLSRSYAS- | WYQQKPGQAPVLLIY- | RDTSRPS---- | GVPDRFSGSSSGNTATLTISGAQAGEADYYC | ATSGGSGSNPQYV | FGGGTQLTVTG |
| XBR2-TOP72 | QPVLTQSPSASASALGSSAKLTC | TLSSAHKTYTIA | WYQQQGEAPRLLMML | RTIGSYTKGT | GVPDRFSGSSSGADRYLTISSVQADDAAGYYC | GADYSGGYV--- | FGGGTQLTVTG |
| ERR2-302 | SYELTQLPSVSVSLGQTARITC | GGASIGSKVH- | WYQQKPGLAPGLLIY | DDDERPS---- | GVPDRFSGSNSGDTATLTISGAQGEAEYYC | QLMDGSDTV--- | FGGGTQLTVTG |
| ERR2-TOP35 | SPVLTQPASVQVMLGQTVSLIC | TAETLRSSVAS- | WYQQKPGQAPVLLIY- | RDTSRPS---- | GVPDRFSGSSSGNTATLTISGAQAGEADYYC | ATSDGSGSRVYV | FGGGTQLTVTG |

FIG. 1

| V_H | FR1 | CDR1 | FR2 | CDR2 | FR3 | CDR3 | FR4 |
|---|---|---|---|---|---|---|---|
| | 1 | 30 | 36  49 | | 66  94 | | 103  113 |
| XBR2-401 | QSVKESEGG-LFKPTDTILTLTCTVSGFSLS | SYGVT | WVRQAPGSSGLEWIG | YINTAGNTYYASWAKS | RSTITRNTNENTVTLKMTSLTAADTATYFCAR | DWTSLNI------- | WGPGTLVTISS |
| XBR2-416 | QEQLEESGGGRLVTPGTVPLTCTVSGFSLS | SYNMS | WVRQAPGKGKLEWIG | TTTPGGNIDYATWAKA | RFTVSKTST--TVDLKITSPTTEDTATYFCAR | GIGGAADL------ | WGPGTLVTISS |
| XBR2-433 | QSVKESEGG-LFKPTDTILTLTCTVSGFSLS | TYGVS | WVRQAPGNGLEWIG | AIGSSGSANYASWAKD | RSTITRNTNLNTVTLKMTSLTAADTATYFCAR | DGYYSSGWGPYPNI-- | WGPGTLVTISS |
| XBR2-327 | QEQLEESGGGRLVTPGTPLTLTCTVSGFSLS | SGAIS | WVRQAPGNGLEWIG | FVNSLGNTYYANWAKS | RSAITRNTNENTVTLKMTSLAAADTATYFCAR | DYGMWAFDP----- | WGPGTLVTISS |
| XBR2-TOP9 | QSVEESRG-RLVTPGTPLTLTCTVSGFSLS | SYNIQ | WVRQAPGKGLEWYG | YINTDGSAYYASWAKG | RFTISKTST--TVDLKITSPTTEDTATYFCAR | GGYASSGFNL---- | WGPGTLVTISS |
| XBR2-TOP72 | QEQLEESGGGRLVTPGTPLTLTCTVSGFSLS | SNAMS | WVRQAPGKGLEWYG | FINGGGVHASWARG | RFTISKTST--TVDLKITSPTTEDTATYFCAR | AGTTYYTSPNL--- | WGPGTLVTISS |
| ERR2-302 | QKQLVESGGGLVKPGGSLHLLCTVSGFSLS | SYAIG | WVRQAPGNGLEWIG | IINSYGSTYYASWAKS | RSTITRNTNLNTVTLKMTSLTAADTATYFCAR | SPYGVVSAWGYHRLDL | WGQGTLVTISS |
| ERR2-308 | QEQLEESGGGRLVTPGGSLTLLCAVSGFSLS | NYAMG | WVRQAPGEGGLEWYG | WISAGGAYYASWVNG | RFTISKHSS--TVDLKMTSLTAADTATYFCAR | GASNGDL------ | WGPGTLVTISS |
| ERR2-316 | QKQLVESGGGLVTPGGSLNLLCTVSGFSLS | KYGVS | WVRQAPGNGLEWIG | TIGGSGTSYYASWAKS | RSTITRNTNLNTVTLKMTSLTAADTATYFCAR | YFGMNTGFDI---- | WGPGTLVTISS |
| ERR2-317 | Q-SLRESGGGLVTPGTPLTLLCTASGFSLS | SYEMI | WVRQAPGKGLEWYG | IINAGCNTYYASWAKG | RFTISRHTST--TVDLKMTSPTTEDTATYFCAR | GSSWTCDI----- | WGPGTLVTISS |
| ERR2-TOP2 | Q-SLEESGGGLVTPGTPLTLLCTVSGFSLS | SYAIS | WVRQAPGKGLEWIG | TIGTRGDTAYANWAKG | RFTISKTST--TVTLKMTSPTTEDTATYFCAR | ELVAGGSDL----- | WGPGTLVTISS |
| ERR2-TOP35 | QSVKESEGGLFKPMDT--LILACTVSGFSLN | TYGVS | WVRQAPGNGLEWIG | AVGSSGAINYASWAKS | RSTITRNTNENTVTLKMTSLTAADTATYFCAR | DGYVSSGWGPYFSI-- | WGPGTLVTISS |

FIG. 1 CONT.

SEQUENCE LISTING

<160> NUMBER OF SEQ ID NOS: 142

<210> SEQ ID NO 1
<211> LENGTH: 114
<212> TYPE: PRT
<213> ORGANISM: Oryctolagus cuniculus

<400> SEQUENCE: 1

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ser Tyr Gly
            20                  25                  30

Val Thr Trp Val Arg Gln Ala Pro Gly Ser Gly Leu Glu Trp Ile Gly
        35                  40                  45

Tyr Ile Asn Thr Ala Gly Asn Thr Tyr Tyr Ala Ser Trp Ala Lys Ser
    50                  55                  60

Arg Ser Thr Ile Thr Arg Asn Thr Asn Glu Asn Thr Val Thr Leu Lys
65                  70                  75                  80

Met Thr Ser Leu Thr Ala Ala Asp Thr Ala Thr Tyr Phe Cys Ala Arg
                85                  90                  95

Asp Trp Thr Ser Leu Asn Ile Trp Gly Pro Gly Thr Leu Val Thr Val
            100                 105                 110

Ser Ser

<210> SEQ ID NO 2
<211> LENGTH: 114
<212> TYPE: PRT
<213> ORGANISM: Oryctolagus cuniculus

<400> SEQUENCE: 2

Gln Glu Gln Leu Glu Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Trp Met Ser Trp Val Arg Gln Ala Pro Gly Lys Gly Leu Glu Trp Ile
        35                  40                  45

Gly Thr Ile Thr Pro Gly Gly Asn Thr Asp Tyr Ala Thr Trp Ala Lys
    50                  55                  60

```
Ala Arg Phe Thr Val Ser Lys Thr Ser Thr Thr Val Asp Leu Lys Ile
 65                  70                  75                  80

Thr Ser Pro Thr Thr Glu Asp Thr Ala Thr Tyr Phe Cys Ala Arg Gly
                 85                  90                  95

Ile Gly Gly Ala Ala Asp Leu Trp Gly Pro Gly Thr Leu Val Thr Ile
            100                 105                 110

Ser Ser

<210> SEQ ID NO 3
<211> LENGTH: 121
<212> TYPE: PRT
<213> ORGANISM: Oryctolagus cuniculus

<400> SEQUENCE: 3

Gln Ser Val Lys Glu Ser Glu Gly Gly Leu Phe Lys Pro Thr Asp Thr
 1               5                  10                  15

Leu Thr Leu Thr Cys Thr Val Ser Gly Phe Ser Leu Ser Thr Tyr Gly
                20                  25                  30

Val Ser Trp Val Arg Gln Ala Pro Gly Asn Gly Leu Glu Trp Ile Gly
            35                  40                  45

Ala Ile Gly Ser Ser Gly Ser Ala Asn Tyr Ala Ser Trp Ala Lys Asp
        50                  55                  60

Arg Ser Thr Ile Thr Arg Asn Thr Asn Leu Asn Thr Val Thr Leu Lys
 65                  70                  75                  80

Met Thr Ser Leu Thr Ala Ala Asp Thr Ala Thr Tyr Phe Cys Ala Arg
                85                  90                  95

Asp Gly Tyr Tyr Ser Ser Gly Trp Gly Pro Tyr Phe Asn Ile Trp Gly
            100                 105                 110

Pro Gly Thr Leu Val Thr Ile Ser Ser
        115                 120

<210> SEQ ID NO 4
<211> LENGTH: 117
<212> TYPE: PRT
<213> ORGANISM: Oryctolagus cuniculus

<400> SEQUENCE: 4

Gln Glu Gln Leu Lys Glu Ser Gly Gly Gly Leu Phe Lys Pro Thr Asp
 1               5                  10                  15

Thr Leu Thr Leu Thr Cys Thr Val Ser Gly Phe Ser Leu Ser Ser Gly
                20                  25                  30

Ala Ile Ser Trp Val Arg Gln Ala Pro Gly Asn Gly Leu Glu Tyr Ile
            35                  40                  45

Gly Phe Val Asn Ser Leu Gly Asn Thr Tyr Tyr Ala Asn Trp Ala Lys
        50                  55                  60

Ser Arg Ser Ala Ile Thr Arg Asn Thr Asn Glu Asn Thr Val Thr Leu
 65                  70                  75                  80

Lys Met Thr Ser Leu Ala Ala Ala Asp Thr Ala Thr Tyr Phe Cys Ala
                85                  90                  95

Lys Asp Tyr Gly Asn Trp Ala Phe Asp Pro Trp Gly Pro Gly Thr Leu
            100                 105                 110

Val Thr Val Ser Ser
        115

<210> SEQ ID NO 5
<211> LENGTH: 114
```

```
<212> TYPE: PRT
<213> ORGANISM: Oryctolagus cuniculus

<400> SEQUENCE: 5

Gln Ser Val Glu Glu Ser Arg Gly Arg Leu Val Thr Pro Gly Thr Pro
1               5                   10                  15

Leu Thr Leu Ile Cys Thr Val Ser Gly Ile Asp Leu Ser Ser Tyr Asn
                20                  25                  30

Ile Gln Trp Val Arg Gln Ala Pro Gly Lys Gly Leu Glu Tyr Ile Gly
            35                  40                  45

Tyr Ile Asn Thr Asp Gly Ser Ala Tyr Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Tyr Ala Ser Gly Phe Asn Leu Trp Gly Pro Gly Thr Leu Val Thr Ile
                100                 105                 110

Ser Ser

<210> SEQ ID NO 6
<211> LENGTH: 117
<212> TYPE: PRT
<213> ORGANISM: Oryctolagus cuniculus

<400> SEQUENCE: 6

Gln Glu Gln Leu Glu Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
                20                  25                  30

Ala Met Ser Trp Val Arg Gln Ala Pro Gly Lys Gly Leu Glu Tyr Val
            35                  40                  45

Gly Phe Ile Asn Gly Gly Gly Val His Tyr Ala Ser Trp Ala Arg
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Ala
                85                  90                  95

Gly Thr Thr Tyr Tyr Thr Ser Phe Asn Leu Trp Gly Pro Gly Thr Leu
                100                 105                 110

Val Thr Ile Ser Ser
        115

<210> SEQ ID NO 7
<211> LENGTH: 124
<212> TYPE: PRT
<213> ORGANISM: Oryctolagus cuniculus

<400> SEQUENCE: 7

Gln Lys Gln Leu Val Glu Ser Gly Gly Gly Leu Val Lys Pro Gly Gly
1               5                   10                  15

Ser Leu Thr Leu Thr Cys Thr Val Ser Gly Phe Ser Leu Ser Ser Tyr
                20                  25                  30

Ala Ile Gly Trp Val Arg Gln Ala Pro Gly Asn Gly Leu Glu Trp Ile
            35                  40                  45

Gly Ile Ile Asn Ser Tyr Gly Ser Thr Tyr Tyr Ala Ser Trp Ala Lys
    50                  55                  60
```

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Arg Ser Pro Tyr Gly Tyr Val Ser Ala Trp Gly Tyr His Arg Leu Asp
            100                 105                 110

Leu Trp Gly Gln Gly Thr Leu Val Thr Ile Ser Ser
        115                 120

<210> SEQ ID NO 8
<211> LENGTH: 114
<212> TYPE: PRT
<213> ORGANISM: Oryctolagus cuniculus

<400> SEQUENCE: 8

Gln Glu Gln Leu Glu Glu Ser Gly Gly Arg Leu Val Thr Pro Gly Thr
1               5                   10                  15

Pro Leu Thr Leu Thr Cys Ala Val Ser Gly Phe Ser Leu Ser Asn Tyr
            20                  25                  30

Ala Met Gly Trp Val Arg Gln Ala Pro Gly Glu Gly Leu Glu Tyr Ile
        35                  40                  45

Gly Trp Ile Ser Ala Gly Gly Ala Tyr Tyr Ala Ser Trp Val Asn
    50                  55                  60

Gly Arg Phe Thr Ile Ser Lys Thr Ser Ser Thr Val Asp Leu Lys Met
65                  70                  75                  80

Thr Ser Leu Thr Ala Ala Asp Thr Ala Thr Tyr Phe Cys Ala Arg Gly
                85                  90                  95

Ala Ser Asn Gly Cys Asp Leu Trp Gly Pro Gly Thr Leu Val Thr Val
            100                 105                 110

Ser Ser

<210> SEQ ID NO 9
<211> LENGTH: 118
<212> TYPE: PRT
<213> ORGANISM: Oryctolagus cuniculus

<400> SEQUENCE: 9

Gln Lys Gln Leu Val Glu Ser Gly Gly Arg Leu Val Thr Pro Gly Gly
1               5                   10                  15

Ser Leu Thr Leu Thr Cys Thr Val Ser Gly Phe Ser Leu Ser Lys Tyr
            20                  25                  30

Gly Val Ser Trp Val Arg Gln Ala Pro Gly Ser Gly Leu Glu Tyr Ile
        35                  40                  45

Gly Thr Ile Gly Gly Ser Gly Thr Ser Tyr Tyr Ala Ser Trp Ala Lys
    50                  55                  60

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Arg Tyr Phe Gly Trp Asn Thr Gly Phe Asp Ile Trp Gly Pro Gly Thr
            100                 105                 110

Leu Val Thr Ile Ser Ser
            115

<210> SEQ ID NO 10
<211> LENGTH: 113

```
<212> TYPE: PRT
<213> ORGANISM: Oryctolagus cuniculus

<400> SEQUENCE: 10

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
                20                  25                  30

Met Ile Trp Val Arg Gln Ala Pro Gly Lys Gly Leu Glu Tyr Ile Gly
            35                  40                  45

Ile Ile Asn Ala Gly Gly Asn Thr Tyr Tyr Ala Ser Trp Ala Lys Gly
        50                  55                  60

Arg Phe Thr Ile Ser Arg Thr Ser Thr Thr Val Asp Leu Lys Met Thr
65              70                  75                  80

Ser Pro Thr Thr Glu Asp Thr Ala Thr Tyr Phe Cys Ala Arg Gly Ser
                85                  90                  95

Ser Trp Thr Gly Asp Ile Trp Gly Pro Gly Thr Leu Val Thr Val Ser
                100                 105                 110

Ser

<210> SEQ ID NO 11
<211> LENGTH: 115
<212> TYPE: PRT
<213> ORGANISM: Oryctolagus cuniculus

<400> SEQUENCE: 11

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
                20                  25                  30

Ile Ser Trp Val Arg Gln Ala Pro Gly Lys Gly Leu Glu Trp Ile Gly
            35                  40                  45

Thr Ile Gly Thr Arg Gly Asp Thr Ala Tyr Ala Asn Trp Ala Lys Gly
        50                  55                  60

Arg Phe Thr Ile Ser Lys Thr Ser Thr Thr Val Thr Leu Lys Met Thr
65              70                  75                  80

Ser Pro Thr Thr Glu Asp Thr Ala Thr Tyr Phe Cys Ala Arg Glu Leu
                85                  90                  95

Val Ala Gly Gly Gly Ser Asp Leu Trp Gly Pro Gly Thr Leu Val Thr
                100                 105                 110

Val Ser Ser
        115

<210> SEQ ID NO 12
<211> LENGTH: 121
<212> TYPE: PRT
<213> ORGANISM: Oryctolagus cuniculus

<400> SEQUENCE: 12

Gln Ser Val Lys Glu Ser Glu Gly Gly Leu Phe Lys Pro Met Asp Thr
1               5                   10                  15

Leu Thr Leu Thr Cys Thr Val Ser Gly Phe Ser Leu Asn Thr Tyr Gly
                20                  25                  30

Val Ser Trp Val Arg Gln Ala Pro Gly Asn Gly Leu Glu Trp Ile Gly
            35                  40                  45

Ala Val Gly Ser Ser Gly Ala Thr Asn Tyr Ala Ser Trp Ala Lys Ser
        50                  55                  60
```

```
Arg Ser Thr Ile Thr Arg Asn Thr Asn Glu Asn Thr Val Thr Leu Lys
 65                  70                  75                  80

Met Thr Ser Leu Thr Ala Ala Asp Thr Ala Thr Tyr Phe Cys Ala Arg
                 85                  90                  95

Asp Gly Tyr Tyr Ser Ser Gly Trp Gly Pro Tyr Phe Ser Ile Trp Gly
            100                 105                 110

Pro Gly Thr Leu Val Thr Val Ser Ser
            115                 120
```

<210> SEQ ID NO 13
<211> LENGTH: 110
<212> TYPE: PRT
<213> ORGANISM: Oryctolagus cuniculus

<400> SEQUENCE: 13

```
Asp Pro Met Leu Thr Gln Thr Pro Ser Ser Thr Ser Thr Ala Val Gly
  1               5                  10                  15

Asp Thr Val Thr Ile Lys Cys Gln Ala Ser Gln Ser Ile Ser Ser Asp
                 20                  25                  30

Leu Ser Trp Tyr Gln Gln Lys Pro Gly Gln Arg Pro Lys Leu Leu Ile
             35                  40                  45

Tyr Gln Ala Ser Thr Leu Ala Ser Gly Val Pro Ser Arg Phe Lys Gly
 50                  55                  60

Ser Gly Tyr Gly Thr Glu Tyr Thr Leu Thr Ile Ser Gly Val Gln Arg
 65                  70                  75                  80

Glu Asp Ala Ala Ile Tyr Tyr Cys Leu Gly Gly Tyr Ala Asp Ala Ser
                 85                  90                  95

Tyr Arg Thr Ala Phe Gly Gly Gly Thr Lys Leu Glu Ile Lys
            100                 105                 110
```

<210> SEQ ID NO 14
<211> LENGTH: 111
<212> TYPE: PRT
<213> ORGANISM: Oryctolagus cuniculus

<400> SEQUENCE: 14

```
Ala Gln Val Leu Thr Gln Thr Pro Ser Ser Thr Ser Ala Ala Val Gly
  1               5                  10                  15

Gly Thr Val Thr Ile Lys Cys Gln Ala Ser Gln Ser Ile Ser Ser Ser
                 20                  25                  30

Asp Leu Ser Trp Tyr Gln Gln Lys Pro Gly Gln Pro Pro Lys Leu Leu
             35                  40                  45

Ile Tyr Ala Thr Ser Tyr Leu Ala Ser Gly Val Pro Ser Arg Phe Lys
 50                  55                  60

Gly Ser Gly Ser Gly Thr Glu Tyr Thr Leu Thr Ile Ser Gly Val Gln
 65                  70                  75                  80

Arg Glu Asp Ala Ala Thr Tyr Tyr Cys Leu Gly Gly Tyr Pro Asn Thr
                 85                  90                  95

Ser Tyr Arg Ser Ala Phe Gly Gly Gly Thr Lys Val Glu Ile Lys
            100                 105                 110
```

<210> SEQ ID NO 15
<211> LENGTH: 111
<212> TYPE: PRT
<213> ORGANISM: Oryctolagus cuniculus

<400> SEQUENCE: 15

```
Ser Phe Val Leu Thr Gln Pro Ala Ser Val Gln Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Gly Gly Ser Gly Ser Asn
                85                  90                  95

Pro Gln Tyr Val Phe Gly Gly Gly Thr Gln Leu Thr Val Thr Gly
            100                 105                 110

<210> SEQ ID NO 16
<211> LENGTH: 110
<212> TYPE: PRT
<213> ORGANISM: Oryctolagus cuniculus

<400> SEQUENCE: 16

Asp Pro Val Leu Thr Gln Thr Pro Ser Ser Val Ser Ala Ala Val Gly
1               5                   10                  15

Gly Thr Val Ala Ile Asn Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Gly Ala Ser Lys Leu Ala Ser Gly Val Pro Ser Arg Phe Ser Gly
    50                  55                  60

Ser Gly Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Tyr Ala Ser Ala Ser
                85                  90                  95

Tyr Arg Thr Ala Phe Gly Gly Gly Thr Lys Leu Glu Ile Lys
            100                 105                 110

<210> SEQ ID NO 17
<211> LENGTH: 110
<212> TYPE: PRT
<213> ORGANISM: Oryctolagus cuniculus

<400> SEQUENCE: 17

Asp Val Val Met Thr Gln Thr Pro Ser Ser Thr Ser Ala Ala Val Gly
1               5                   10                  15

Gly Thr Val Thr Ile Lys Cys Gln Ala Ser Gln Asn Ile Gly Pro Trp
            20                  25                  30

Leu Ser Trp Tyr Gln Gln Lys Pro Gly Gln Pro Pro Lys Gln Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Asp Tyr Thr Leu Thr Ile Ser Gly Val Gln Arg
65                  70                  75                  80

Glu Asp Ala Ala Thr Tyr Tyr Cys Leu Gly Trp His Ser Trp Ser Asp
                85                  90                  95

Asp Gly Trp Ala Phe Gly Ala Gly Thr Asn Val Glu Ile Lys
            100                 105                 110
```

<210> SEQ ID NO 18
<211> LENGTH: 112
<212> TYPE: PRT
<213> ORGANISM: Oryctolagus cuniculus

<400> SEQUENCE: 18

Gln Phe Val Leu Thr Gln Ser Pro Ser Ala Ser Ala Leu Gly Ser
1               5                   10                  15

Ser Ala Lys Leu Thr Cys Thr Leu Ser Ser Ala His Lys Thr Tyr Thr
            20                  25                  30

Ile Ala Trp Tyr Gln Gln Gln Gly Glu Ala Pro Arg Leu Leu Met
        35                  40                  45

Met Leu Arg Thr Asp Gly Ser Tyr Thr Lys Gly Thr Gly Val Pro Asp
    50                  55                  60

Arg Phe Ser Gly Ser Ser Ser Gly Ala Asp Arg Tyr Leu Ile Ile Ser
65                  70                  75                  80

Ser Val Gln Ala Asp Asp Ala Ala Gly Tyr Tyr Cys Gly Ala Asp Tyr
                85                  90                  95

Ser Gly Gly Tyr Val Phe Gly Gly Gly Thr Gln Leu Thr Val Thr Gly
            100                 105                 110

<210> SEQ ID NO 19
<211> LENGTH: 107
<212> TYPE: PRT
<213> ORGANISM: Oryctolagus cuniculus

<400> SEQUENCE: 19

Ser Tyr Glu Leu Thr Gln Leu Pro Ser Val Ser Val Ser Leu Gly Gln
1               5                   10                  15

Thr Ala Arg Ile Thr Cys Gly Gly Ala Ser Ile Gly Ser Lys Val Val
            20                  25                  30

His Trp Tyr Gln Gln Lys Pro Gly Leu Ala Pro Gly Leu Leu Ile Tyr
        35                  40                  45

Asp Asp Asp Glu Arg Pro Ser Gly Val Pro Asp Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Glu Tyr Tyr Cys Gln Leu Trp Asp Gly Ser Asp Val Val
                85                  90                  95

Phe Gly Gly Gly Thr Gln Leu Thr Val Thr Gly
            100                 105

<210> SEQ ID NO 20
<211> LENGTH: 108
<212> TYPE: PRT
<213> ORGANISM: Oryctolagus cuniculus

<400> SEQUENCE: 20

Asp Pro Met Leu Thr Gln Thr Pro Ser Ser Val Ser Ala Val Val Gly
1               5                   10                  15

Gly Thr Val Thr Ile Lys Cys Gln Ala Ser Gln Ser Ile Thr Ser Trp
            20                  25                  30

Leu Ser Trp Tyr Gln Gln Lys Pro Gly Gln Pro Pro Lys Leu Leu Ile
        35                  40                  45

Tyr Gly Ala Ser His Leu Ala Ser Gly Val Pro Ser Arg Phe Lys Gly
    50                  55                  60

Ser Gly Tyr Gly Thr Glu Phe Thr Leu Thr Ile Ser Gly Ile Gln Arg

```
                65                  70                  75                  80
Glu Asp Ala Ala Thr Tyr Tyr Cys Leu Gly Gly Tyr Ser Asn Ser Asp
                    85                  90                  95

Ile Val Phe Gly Gly Gly Thr Glu Leu Glu Ile Leu
                100                 105
```

<210> SEQ ID NO 21
<211> LENGTH: 110
<212> TYPE: PRT
<213> ORGANISM: Oryctolagus cuniculus

<400> SEQUENCE: 21

```
Asp Pro Val Met Thr Gln Thr Pro Ser Ser Val Ser Glu Pro Val Gly
1               5                   10                  15

Gly Thr Val Thr Ile Lys Cys Gln Ala Ser Gln Ser Ile Ser Asn Ala
                20                  25                  30

Leu Ala Trp Tyr Gln Gln Lys Pro Gly Gln Pro Pro Lys Arg Leu Ile
            35                  40                  45

Tyr Lys Ala Ser Thr Pro Ala Ser Gly Val Pro Ser Arg Phe Lys Gly
        50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Phe Ser Val Val Ser Asn
                    85                  90                  95

Asp Gly Trp Ala Phe Gly Ala Gly Thr Asn Val Glu Ile Lys
                100                 105                 110
```

<210> SEQ ID NO 22
<211> LENGTH: 110
<212> TYPE: PRT
<213> ORGANISM: Oryctolagus cuniculus

<400> SEQUENCE: 22

```
Asp Pro Val Leu Thr Gln Thr Pro Ser Ser Thr Ser Ala Ala Val Gly
1               5                   10                  15

Gly Thr Val Thr Ile Lys Cys Gln Ala Ser Gln Ser Ile Ser Ser Tyr
                20                  25                  30

Leu Ser Trp Tyr Gln Gln Lys Pro Gly Gln Pro Pro Lys Gln Leu Ile
            35                  40                  45

Tyr Ala Ala Ser Thr Leu Ala Ser Gly Val Pro Ser Arg Phe Lys Gly
        50                  55                  60

Ser Gly Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Tyr Ala Ser Ala Ser
                    85                  90                  95

Tyr Gln Thr Ala Phe Gly Gly Gly Thr Lys Val Glu Ile Lys
                100                 105                 110
```

<210> SEQ ID NO 23
<211> LENGTH: 110
<212> TYPE: PRT
<213> ORGANISM: Oryctolagus cuniculus

<400> SEQUENCE: 23

```
Asp Val Val Met Thr Gln Thr Pro Ser Ser Val Ser Ala Val Val Gly
1               5                   10                  15

Gly Thr Val Thr Ile Lys Cys Gln Ala Ser Gln Ser Ile Thr Ser Trp
                20                  25                  30
```

-continued

Leu Ser Trp Tyr Gln Gln Lys Pro Gly Gln Pro Pro Lys Leu Leu Ile
         35                  40                  45

Tyr Gly Ala Ser His Leu Ala Ser Gly Val Pro Ser Arg Phe Lys Gly
     50                  55                  60

Ser Gly Tyr Gly Thr Glu Phe Thr Leu Thr Ile Ser Gly Ile Gln Arg
65                  70                  75                  80

Glu Asp Ala Ala Thr Tyr Tyr Cys Leu Gly Gly Tyr Leu Ser Ala Ser
                 85                  90                  95

Tyr Gln Thr Ala Phe Gly Gly Gly Thr Lys Val Glu Ile Lys
            100                 105                 110

<210> SEQ ID NO 24
<211> LENGTH: 110
<212> TYPE: PRT
<213> ORGANISM: Oryctolagus cuniculus

<400> SEQUENCE: 24

Ser Phe Val Leu Thr Gln Pro Ala Ser Val Gln Val Asn Leu Gly Gln
1               5                   10                  15

Thr Val Ser Leu Thr Cys Thr Ala Glu Thr Leu Arg Ser Ser Tyr Ala
            20                  25                  30

Ser Trp Tyr Gln Gln Lys Pro Gly Gln Ala Pro Val Leu Leu Ile Tyr
         35                  40                  45

Arg Asp Thr Ser Arg Pro Ser Gly Val Pro Asp Arg Phe Ser Gly Ser
     50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Arg
                 85                  90                  95

Tyr Tyr Val Phe Gly Gly Gly Thr Gln Leu Thr Val Thr Gly
            100                 105                 110

<210> SEQ ID NO 25
<211> LENGTH: 5
<212> TYPE: PRT
<213> ORGANISM: Oryctolagus cuniculus

<400> SEQUENCE: 25

Ser Tyr Gly Val Thr
1               5

<210> SEQ ID NO 26
<211> LENGTH: 16
<212> TYPE: PRT
<213> ORGANISM: Oryctolagus cuniculus

<400> SEQUENCE: 26

Tyr Ile Asn Thr Ala Gly Asn Thr Tyr Tyr Ala Ser Trp Ala Lys Ser
1               5                   10                  15

<210> SEQ ID NO 27
<211> LENGTH: 7
<212> TYPE: PRT
<213> ORGANISM: Oryctolagus cuniculus

<400> SEQUENCE: 27

Asp Trp Thr Ser Leu Asn Ile
1               5

```
<210> SEQ ID NO 28
<211> LENGTH: 5
<212> TYPE: PRT
<213> ORGANISM: Oryctolagus cuniculus

<400> SEQUENCE: 28

Ser Tyr Trp Met Ser
1               5

<210> SEQ ID NO 29
<211> LENGTH: 16
<212> TYPE: PRT
<213> ORGANISM: Oryctolagus cuniculus

<400> SEQUENCE: 29

Thr Ile Thr Pro Gly Gly Asn Thr Asp Tyr Ala Thr Trp Ala Lys Ala
1               5                   10                  15

<210> SEQ ID NO 30
<211> LENGTH: 8
<212> TYPE: PRT
<213> ORGANISM: Oryctolagus cuniculus

<400> SEQUENCE: 30

Gly Ile Gly Gly Ala Ala Asp Leu
1               5

<210> SEQ ID NO 31
<211> LENGTH: 5
<212> TYPE: PRT
<213> ORGANISM: Oryctolagus cuniculus

<400> SEQUENCE: 31

Thr Tyr Gly Val Ser
1               5

<210> SEQ ID NO 32
<211> LENGTH: 16
<212> TYPE: PRT
<213> ORGANISM: Oryctolagus cuniculus

<400> SEQUENCE: 32

Ala Ile Gly Ser Ser Gly Ser Ala Asn Tyr Ala Ser Trp Ala Lys Asp
1               5                   10                  15

<210> SEQ ID NO 33
<211> LENGTH: 14
<212> TYPE: PRT
<213> ORGANISM: Oryctolagus cuniculus

<400> SEQUENCE: 33

Asp Gly Tyr Tyr Ser Ser Gly Trp Gly Pro Tyr Phe Asn Ile
1               5                   10

<210> SEQ ID NO 34
<211> LENGTH: 5
<212> TYPE: PRT
<213> ORGANISM: Oryctolagus cuniculus

<400> SEQUENCE: 34

Ser Gly Ala Ile Ser
1               5

<210> SEQ ID NO 35
<211> LENGTH: 16
```

```
<212> TYPE: PRT
<213> ORGANISM: Oryctolagus cuniculus

<400> SEQUENCE: 35

Phe Val Asn Ser Leu Gly Asn Thr Tyr Tyr Ala Asn Trp Ala Lys Ser
1               5                   10                  15

<210> SEQ ID NO 36
<211> LENGTH: 9
<212> TYPE: PRT
<213> ORGANISM: Oryctolagus cuniculus

<400> SEQUENCE: 36

Asp Tyr Gly Asn Trp Ala Phe Asp Pro
1               5

<210> SEQ ID NO 37
<211> LENGTH: 5
<212> TYPE: PRT
<213> ORGANISM: Oryctolagus cuniculus

<400> SEQUENCE: 37

Ser Tyr Asn Ile Gln
1               5

<210> SEQ ID NO 38
<211> LENGTH: 16
<212> TYPE: PRT
<213> ORGANISM: Oryctolagus cuniculus

<400> SEQUENCE: 38

Tyr Ile Asn Thr Asp Gly Ser Ala Tyr Tyr Ala Ser Trp Ala Lys Gly
1               5                   10                  15

<210> SEQ ID NO 39
<211> LENGTH: 9
<212> TYPE: PRT
<213> ORGANISM: Oryctolagus cuniculus

<400> SEQUENCE: 39

Gly Gly Tyr Ala Ser Gly Phe Asn Leu
1               5

<210> SEQ ID NO 40
<211> LENGTH: 5
<212> TYPE: PRT
<213> ORGANISM: Oryctolagus cuniculus

<400> SEQUENCE: 40

Ser Asn Ala Met Ser
1               5

<210> SEQ ID NO 41
<211> LENGTH: 16
<212> TYPE: PRT
<213> ORGANISM: Oryctolagus cuniculus

<400> SEQUENCE: 41

Phe Ile Asn Gly Gly Gly Gly Val His Tyr Ala Ser Trp Ala Arg Gly
1               5                   10                  15

<210> SEQ ID NO 42
<211> LENGTH: 11
<212> TYPE: PRT
<213> ORGANISM: Oryctolagus cuniculus
```

<400> SEQUENCE: 42

Ala Gly Thr Thr Tyr Tyr Thr Ser Phe Asn Leu
1               5                   10

<210> SEQ ID NO 43
<211> LENGTH: 5
<212> TYPE: PRT
<213> ORGANISM: Oryctolagus cuniculus

<400> SEQUENCE: 43

Ser Tyr Ala Ile Gly
1               5

<210> SEQ ID NO 44
<211> LENGTH: 16
<212> TYPE: PRT
<213> ORGANISM: Oryctolagus cuniculus

<400> SEQUENCE: 44

Ile Ile Asn Ser Tyr Gly Ser Thr Tyr Tyr Ala Ser Trp Ala Lys Ser
1               5                   10                  15

<210> SEQ ID NO 45
<211> LENGTH: 16
<212> TYPE: PRT
<213> ORGANISM: Oryctolagus cuniculus

<400> SEQUENCE: 45

Ser Pro Tyr Gly Tyr Val Ser Ala Trp Gly Tyr His Arg Leu Asp Leu
1               5                   10                  15

<210> SEQ ID NO 46
<211> LENGTH: 5
<212> TYPE: PRT
<213> ORGANISM: Oryctolagus cuniculus

<400> SEQUENCE: 46

Asn Tyr Ala Met Gly
1               5

<210> SEQ ID NO 47
<211> LENGTH: 16
<212> TYPE: PRT
<213> ORGANISM: Oryctolagus cuniculus

<400> SEQUENCE: 47

Trp Ile Ser Ala Gly Gly Gly Ala Tyr Tyr Ala Ser Trp Val Asn Gly
1               5                   10                  15

<210> SEQ ID NO 48
<211> LENGTH: 8
<212> TYPE: PRT
<213> ORGANISM: Oryctolagus cuniculus

<400> SEQUENCE: 48

Gly Ala Ser Asn Gly Cys Asp Leu
1               5

<210> SEQ ID NO 49
<211> LENGTH: 5
<212> TYPE: PRT
<213> ORGANISM: Oryctolagus cuniculus

<400> SEQUENCE: 49

```
Lys Tyr Gly Val Ser
1               5
```

<210> SEQ ID NO 50
<211> LENGTH: 16
<212> TYPE: PRT
<213> ORGANISM: Oryctolagus cuniculus

<400> SEQUENCE: 50

```
Thr Ile Gly Gly Ser Gly Thr Ser Tyr Tyr Ala Ser Trp Ala Lys Ser
1               5                   10                  15
```

<210> SEQ ID NO 51
<211> LENGTH: 10
<212> TYPE: PRT
<213> ORGANISM: Oryctolagus cuniculus

<400> SEQUENCE: 51

```
Tyr Phe Gly Trp Asn Thr Gly Phe Asp Ile
1               5                   10
```

<210> SEQ ID NO 52
<211> LENGTH: 5
<212> TYPE: PRT
<213> ORGANISM: Oryctolagus cuniculus

<400> SEQUENCE: 52

```
Ser Tyr Asp Met Ile
1               5
```

<210> SEQ ID NO 53
<211> LENGTH: 16
<212> TYPE: PRT
<213> ORGANISM: Oryctolagus cuniculus

<400> SEQUENCE: 53

```
Ile Ile Asn Ala Gly Gly Asn Thr Tyr Tyr Ala Ser Trp Ala Lys Gly
1               5                   10                  15
```

<210> SEQ ID NO 54
<211> LENGTH: 8
<212> TYPE: PRT
<213> ORGANISM: Oryctolagus cuniculus

<400> SEQUENCE: 54

```
Gly Ser Ser Trp Thr Gly Asp Ile
1               5
```

<210> SEQ ID NO 55
<211> LENGTH: 5
<212> TYPE: PRT
<213> ORGANISM: Oryctolagus cuniculus

<400> SEQUENCE: 55

```
Ser Tyr Ala Ile Ser
1               5
```

<210> SEQ ID NO 56
<211> LENGTH: 16
<212> TYPE: PRT
<213> ORGANISM: Oryctolagus cuniculus

<400> SEQUENCE: 56

```
Thr Ile Gly Thr Arg Gly Asp Thr Ala Tyr Ala Asn Trp Ala Lys Gly
```

<210> SEQ ID NO 57
<211> LENGTH: 10
<212> TYPE: PRT
<213> ORGANISM: Oryctolagus cuniculus

<400> SEQUENCE: 57

Glu Leu Val Ala Gly Gly Gly Ser Asp Leu
1               5                   10

<210> SEQ ID NO 58
<211> LENGTH: 5
<212> TYPE: PRT
<213> ORGANISM: Oryctolagus cuniculus

<400> SEQUENCE: 58

Thr Tyr Gly Val Ser
1               5

<210> SEQ ID NO 59
<211> LENGTH: 16
<212> TYPE: PRT
<213> ORGANISM: Oryctolagus cuniculus

<400> SEQUENCE: 59

Ala Val Gly Ser Ser Gly Ala Thr Asn Tyr Ala Ser Trp Ala Lys Ser
1               5                   10                  15

<210> SEQ ID NO 60
<211> LENGTH: 14
<212> TYPE: PRT
<213> ORGANISM: Oryctolagus cuniculus

<400> SEQUENCE: 60

Asp Gly Tyr Tyr Ser Ser Gly Trp Gly Pro Tyr Phe Ser Ile
1               5                   10

<210> SEQ ID NO 61
<211> LENGTH: 11
<212> TYPE: PRT
<213> ORGANISM: Oryctolagus cuniculus

<400> SEQUENCE: 61

Gln Ala Ser Gln Ser Ile Ser Ser Asp Leu Ser
1               5                   10

<210> SEQ ID NO 62
<211> LENGTH: 7
<212> TYPE: PRT
<213> ORGANISM: Oryctolagus cuniculus

<400> SEQUENCE: 62

Gln Ala Ser Thr Leu Ala Ser
1               5

<210> SEQ ID NO 63
<211> LENGTH: 12
<212> TYPE: PRT
<213> ORGANISM: Oryctolagus cuniculus

<400> SEQUENCE: 63

Leu Gly Gly Tyr Ala Asp Ala Ser Tyr Arg Thr Ala
1               5                   10

<210> SEQ ID NO 64
<211> LENGTH: 12
<212> TYPE: PRT
<213> ORGANISM: Oryctolagus cuniculus

<400> SEQUENCE: 64

Gln Ala Ser Gln Ser Ile Ser Ser Ser Asp Leu Ser
1               5                   10

<210> SEQ ID NO 65
<211> LENGTH: 7
<212> TYPE: PRT
<213> ORGANISM: Oryctolagus cuniculus

<400> SEQUENCE: 65

Ala Thr Ser Tyr Leu Ala Ser
1               5

<210> SEQ ID NO 66
<211> LENGTH: 12
<212> TYPE: PRT
<213> ORGANISM: Oryctolagus cuniculus

<400> SEQUENCE: 66

Leu Gly Gly Tyr Pro Asn Thr Ser Tyr Arg Ser Ala
1               5                   10

<210> SEQ ID NO 67
<211> LENGTH: 11
<212> TYPE: PRT
<213> ORGANISM: Oryctolagus cuniculus

<400> SEQUENCE: 67

Thr Ala Asp Thr Leu Ser Arg Ser Tyr Ala Ser
1               5                   10

<210> SEQ ID NO 68
<211> LENGTH: 7
<212> TYPE: PRT
<213> ORGANISM: Oryctolagus cuniculus

<400> SEQUENCE: 68

Arg Asp Thr Ser Arg Pro Ser
1               5

<210> SEQ ID NO 69
<211> LENGTH: 13
<212> TYPE: PRT
<213> ORGANISM: Oryctolagus cuniculus

<400> SEQUENCE: 69

Ala Thr Ser Gly Gly Ser Gly Ser Asn Pro Gln Tyr Val
1               5                   10

<210> SEQ ID NO 70
<211> LENGTH: 11
<212> TYPE: PRT
<213> ORGANISM: Oryctolagus cuniculus

<400> SEQUENCE: 70

Gln Ala Ser Gln Ser Ile Ser Ser Tyr Leu Ser
1               5                   10

<210> SEQ ID NO 71

```
<211> LENGTH: 7
<212> TYPE: PRT
<213> ORGANISM: Oryctolagus cuniculus

<400> SEQUENCE: 71

Gly Ala Ser Lys Leu Ala Ser
1               5

<210> SEQ ID NO 72
<211> LENGTH: 12
<212> TYPE: PRT
<213> ORGANISM: Oryctolagus cuniculus

<400> SEQUENCE: 72

Leu Gly Gly Tyr Ala Ser Ala Ser Tyr Arg Thr Ala
1               5                   10

<210> SEQ ID NO 73
<211> LENGTH: 11
<212> TYPE: PRT
<213> ORGANISM: Oryctolagus cuniculus

<400> SEQUENCE: 73

Gln Ala Ser Gln Asn Ile Gly Pro Trp Leu Ser
1               5                   10

<210> SEQ ID NO 74
<211> LENGTH: 7
<212> TYPE: PRT
<213> ORGANISM: Oryctolagus cuniculus

<400> SEQUENCE: 74

Ala Ala Ser Thr Leu Ala Ser
1               5

<210> SEQ ID NO 75
<211> LENGTH: 12
<212> TYPE: PRT
<213> ORGANISM: Oryctolagus cuniculus

<400> SEQUENCE: 75

Leu Gly Trp His Ser Trp Ser Asp Asp Gly Trp Ala
1               5                   10

<210> SEQ ID NO 76
<211> LENGTH: 12
<212> TYPE: PRT
<213> ORGANISM: Oryctolagus cuniculus

<400> SEQUENCE: 76

Thr Leu Ser Ser Ala His Lys Thr Tyr Thr Ile Ala
1               5                   10

<210> SEQ ID NO 77
<211> LENGTH: 10
<212> TYPE: PRT
<213> ORGANISM: Oryctolagus cuniculus

<400> SEQUENCE: 77

Arg Thr Asp Gly Ser Tyr Thr Lys Gly Thr
1               5                   10

<210> SEQ ID NO 78
<211> LENGTH: 9
<212> TYPE: PRT
```

```
<213> ORGANISM: Oryctolagus cuniculus

<400> SEQUENCE: 78

Gly Ala Asp Tyr Ser Gly Gly Tyr Val
1               5

<210> SEQ ID NO 79
<211> LENGTH: 11
<212> TYPE: PRT
<213> ORGANISM: Oryctolagus cuniculus

<400> SEQUENCE: 79

Gly Gly Ala Ser Ile Gly Ser Lys Val Val His
1               5                   10

<210> SEQ ID NO 80
<211> LENGTH: 7
<212> TYPE: PRT
<213> ORGANISM: Oryctolagus cuniculus

<400> SEQUENCE: 80

Asp Asp Asp Glu Arg Pro Ser
1               5

<210> SEQ ID NO 81
<211> LENGTH: 9
<212> TYPE: PRT
<213> ORGANISM: Oryctolagus cuniculus

<400> SEQUENCE: 81

Gln Leu Trp Asp Gly Ser Asp Val Val
1               5

<210> SEQ ID NO 82
<211> LENGTH: 11
<212> TYPE: PRT
<213> ORGANISM: Oryctolagus cuniculus

<400> SEQUENCE: 82

Gln Ala Ser Gln Ser Ile Thr Ser Trp Leu Ser
1               5                   10

<210> SEQ ID NO 83
<211> LENGTH: 7
<212> TYPE: PRT
<213> ORGANISM: Oryctolagus cuniculus

<400> SEQUENCE: 83

Gly Ala Ser His Leu Ala Ser
1               5

<210> SEQ ID NO 84
<211> LENGTH: 10
<212> TYPE: PRT
<213> ORGANISM: Oryctolagus cuniculus

<400> SEQUENCE: 84

Leu Gly Gly Tyr Ser Asn Ser Asp Ile Val
1               5                   10

<210> SEQ ID NO 85
<211> LENGTH: 11
<212> TYPE: PRT
<213> ORGANISM: Oryctolagus cuniculus
```

```
<400> SEQUENCE: 85

Gln Ala Ser Gln Ser Ile Ser Asn Ala Leu Ala
1               5                   10

<210> SEQ ID NO 86
<211> LENGTH: 7
<212> TYPE: PRT
<213> ORGANISM: Oryctolagus cuniculus

<400> SEQUENCE: 86

Lys Ala Ser Thr Pro Ala Ser
1               5

<210> SEQ ID NO 87
<211> LENGTH: 12
<212> TYPE: PRT
<213> ORGANISM: Oryctolagus cuniculus

<400> SEQUENCE: 87

Leu Gly Phe Ser Val Val Ser Asn Asp Gly Trp Ala
1               5                   10

<210> SEQ ID NO 88
<211> LENGTH: 11
<212> TYPE: PRT
<213> ORGANISM: Oryctolagus cuniculus

<400> SEQUENCE: 88

Gln Ala Ser Gln Ser Ile Ser Ser Tyr Leu Ser
1               5                   10

<210> SEQ ID NO 89
<211> LENGTH: 7
<212> TYPE: PRT
<213> ORGANISM: Oryctolagus cuniculus

<400> SEQUENCE: 89

Ala Ala Ser Thr Leu Ala Ser
1               5

<210> SEQ ID NO 90
<211> LENGTH: 12
<212> TYPE: PRT
<213> ORGANISM: Oryctolagus cuniculus

<400> SEQUENCE: 90

Leu Gly Gly Tyr Ala Ser Ala Ser Tyr Gln Thr Ala
1               5                   10

<210> SEQ ID NO 91
<211> LENGTH: 11
<212> TYPE: PRT
<213> ORGANISM: Oryctolagus cuniculus

<400> SEQUENCE: 91

Gln Ala Ser Gln Ser Ile Thr Ser Trp Leu Ser
1               5                   10

<210> SEQ ID NO 92
<211> LENGTH: 7
<212> TYPE: PRT
<213> ORGANISM: Oryctolagus cuniculus

<400> SEQUENCE: 92
```

```
<210> SEQ ID NO 93
<211> LENGTH: 12
<212> TYPE: PRT
<213> ORGANISM: Oryctolagus cuniculus

<400> SEQUENCE: 93

Leu Gly Gly Tyr Leu Ser Ala Ser Tyr Gln Thr Ala
1               5                   10

<210> SEQ ID NO 94
<211> LENGTH: 11
<212> TYPE: PRT
<213> ORGANISM: Oryctolagus cuniculus

<400> SEQUENCE: 94

Thr Ala Glu Thr Leu Arg Ser Ser Tyr Ala Ser
1               5                   10

<210> SEQ ID NO 95
<211> LENGTH: 7
<212> TYPE: PRT
<213> ORGANISM: Oryctolagus cuniculus

<400> SEQUENCE: 95

Arg Asp Thr Ser Arg Pro Ser
1               5

<210> SEQ ID NO 96
<211> LENGTH: 12
<212> TYPE: PRT
<213> ORGANISM: Oryctolagus cuniculus

<400> SEQUENCE: 96

Ala Thr Ser Asp Gly Ser Gly Ser Arg Tyr Tyr Val
1               5                   10

<210> SEQ ID NO 97
<211> LENGTH: 48
<212> TYPE: DNA
<213> ORGANISM: Artificial sequence
<220> FEATURE:
<223> OTHER INFORMATION: Synthetic sequence

<400> SEQUENCE: 97
gcctaagctt gtctccgggt gccgaagtgg aggttctgga tccgaacg              48

<210> SEQ ID NO 98
<211> LENGTH: 36
<212> TYPE: DNA
<213> ORGANISM: Artificial sequence
<220> FEATURE:
<223> OTHER INFORMATION: Synthetic sequence

<400> SEQUENCE: 98
gctcacgcgg cttgggtgtc cgggagcgcg cgtcgc                           36

<210> SEQ ID NO 99
<211> LENGTH: 36
<212> TYPE: DNA
<213> ORGANISM: Artificial sequence
<220> FEATURE:
<223> OTHER INFORMATION: Synthetic sequence
```

Gly Ala Ser His Leu Ala Ser
1               5

<400> SEQUENCE: 99
gcgacgcgcg ctcccggaca cccaagccgc gtgagc                                      36

<210> SEQ ID NO 100
<211> LENGTH: 48
<212> TYPE: DNA
<213> ORGANISM: Artificial sequence
<220> FEATURE:
<223> OTHER INFORMATION: Synthetic sequence

<400> SEQUENCE: 100
agctctcgag tcaccccatc ttgctgctgt ctcggggact acacgagg                         48

<210> SEQ ID NO 101
<211> LENGTH: 99
<212> TYPE: DNA
<213> ORGANISM: Artificial sequence
<220> FEATURE:
<223> OTHER INFORMATION: Synthetic sequence

<400> SEQUENCE: 101
gctgggtacc ggcgcgccac catggactgg acttggagaa tcctgtttct cgtagctgct           60
gcaactggag cacactccgc ccggggcgcc gccgcccag                                  99

<210> SEQ ID NO 102
<211> LENGTH: 52
<212> TYPE: DNA
<213> ORGANISM: Artificial sequence
<220> FEATURE:
<223> OTHER INFORMATION: Synthetic sequence

<400> SEQUENCE: 102
cggcctcgag tcagtgatgg tgatggtggt gctccatctt gttcttctcc tt                   52

<210> SEQ ID NO 103
<211> LENGTH: 99
<212> TYPE: DNA
<213> ORGANISM: Artificial sequence
<220> FEATURE:
<223> OTHER INFORMATION: Synthetic sequence

<400> SEQUENCE: 103
gctgggtacc ggcgcgccac catggactgg acttggagaa tcctgtttct cgtagctgct           60
gcaactggag cacactccga agtggaggtt ctggatccg                                  99

<210> SEQ ID NO 104
<211> LENGTH: 52
<212> TYPE: DNA
<213> ORGANISM: Artificial sequence
<220> FEATURE:
<223> OTHER INFORMATION: Synthetic sequence

<400> SEQUENCE: 104
cggcctcgag tcagtgatgg tgatggtggt gccccatctt gctgctgtct cg                   52

<210> SEQ ID NO 105
<211> LENGTH: 42
<212> TYPE: DNA
<213> ORGANISM: Artificial sequence
<220> FEATURE:
<223> OTHER INFORMATION: Synthetic sequence

<400> SEQUENCE: 105
gaggaggagc tcactctcag tcagtgaagg agtccgaggg ag                              42

<210> SEQ ID NO 106
<211> LENGTH: 60
<212> TYPE: DNA
<213> ORGANISM: Artificial sequence
<220> FEATURE:
<223> OTHER INFORMATION: Synthetic sequence

<400> SEQUENCE: 106
cgatgggccc ttggtggagg ctgaagagac ggtgacgagg gtccctggtc cccagatgtt    60

<210> SEQ ID NO 107
<211> LENGTH: 41
<212> TYPE: DNA
<213> ORGANISM: Artificial sequence
<220> FEATURE:
<223> OTHER INFORMATION: Synthetic sequence

<400> SEQUENCE: 107
gaggaggagc tcactctcag gagcagctgg aggagtccgg g                        41

<210> SEQ ID NO 108
<211> LENGTH: 60
<212> TYPE: DNA
<213> ORGANISM: Artificial sequence
<220> FEATURE:
<223> OTHER INFORMATION: Synthetic sequence

<400> SEQUENCE: 108
cgatgggccc ttggtggagg ctgaggagat ggtgaccagg gtgcctggcc cccacaagtc    60

<210> SEQ ID NO 109
<211> LENGTH: 41
<212> TYPE: DNA
<213> ORGANISM: Artificial sequence
<220> FEATURE:
<223> OTHER INFORMATION: Synthetic sequence

<400> SEQUENCE: 109
gaggaggagc tcactctcag tcagtgaagg agtccgaggg a                        41

<210> SEQ ID NO 110
<211> LENGTH: 60
<212> TYPE: DNA
<213> ORGANISM: Artificial sequence
<220> FEATURE:
<223> OTHER INFORMATION: Synthetic sequence

<400> SEQUENCE: 110
cgatgggccc ttggtggagg ctgaggagat ggtgaccagg gtgcctggcc cccagatgtt    60

<210> SEQ ID NO 111
<211> LENGTH: 60
<212> TYPE: DNA
<213> ORGANISM: Artificial sequence
<220> FEATURE:
<223> OTHER INFORMATION: Synthetic sequence

<400> SEQUENCE: 111
gagaagcttg ttgctctgga tctctggtgc ctacggggac cctatgctga cccagactcc    60

<210> SEQ ID NO 112
<211> LENGTH: 60
<212> TYPE: DNA
<213> ORGANISM: Artificial sequence
<220> FEATURE:

<223> OTHER INFORMATION: Synthetic sequence

<400> SEQUENCE: 112
gagaagcttg ttgctctgga tctctggtgc ctacgggcaa gtgctgaccc agactccatc    60

<210> SEQ ID NO 113
<211> LENGTH: 60
<212> TYPE: DNA
<213> ORGANISM: Artificial sequence
<220> FEATURE:
<223> OTHER INFORMATION: Synthetic sequence

<400> SEQUENCE: 113
gagaagcttg ttgctctgga tctctggtgc ctacgggtcc ttcgtgctga ctcagccagc    60

<210> SEQ ID NO 114
<211> LENGTH: 21
<212> TYPE: DNA
<213> ORGANISM: Artificial sequence
<220> FEATURE:
<223> OTHER INFORMATION: Synthetic sequence

<400> SEQUENCE: 114
ggccatggct ggttgggcag c                                              21

<210> SEQ ID NO 115
<211> LENGTH: 60
<212> TYPE: DNA
<213> ORGANISM: Artificial sequence
<220> FEATURE:
<223> OTHER INFORMATION: Synthetic sequence

<400> SEQUENCE: 115
ggtaccggcg cgccaccatg gactggactt ggagaatcct gtttctcgta gctgctgcaa    60

<210> SEQ ID NO 116
<211> LENGTH: 20
<212> TYPE: DNA
<213> ORGANISM: Artificial sequence
<220> FEATURE:
<223> OTHER INFORMATION: Synthetic sequence

<400> SEQUENCE: 116
gccgctggtc agggctcctg                                                20

<210> SEQ ID NO 117
<211> LENGTH: 20
<212> TYPE: DNA
<213> ORGANISM: Artificial sequence
<220> FEATURE:
<223> OTHER INFORMATION: Synthetic sequence

<400> SEQUENCE: 117
caggagccct gaccagcggc                                                20

<210> SEQ ID NO 118
<211> LENGTH: 30
<212> TYPE: DNA
<213> ORGANISM: Artificial sequence
<220> FEATURE:
<223> OTHER INFORMATION: Synthetic sequence

<400> SEQUENCE: 118
ggcctcgagt catttacccg gagacaggga                                     30

-continued

```
<210> SEQ ID NO 119
<211> LENGTH: 54
<212> TYPE: DNA
<213> ORGANISM: Artificial sequence
<220> FEATURE:
<223> OTHER INFORMATION: Synthetic sequence

<400> SEQUENCE: 119
tttctcgtag ctgctgcaac tggagcacac tcccaggagc agctggagga gtcc         54

<210> SEQ ID NO 120
<211> LENGTH: 54
<212> TYPE: DNA
<213> ORGANISM: Artificial sequence
<220> FEATURE:
<223> OTHER INFORMATION: Synthetic sequence

<400> SEQUENCE: 120
tttctcgtag ctgctgcaac tggagcacac tcccagtcgt tggaggagtc cggg         54

<210> SEQ ID NO 121
<211> LENGTH: 54
<212> TYPE: DNA
<213> ORGANISM: Artificial sequence
<220> FEATURE:
<223> OTHER INFORMATION: Synthetic sequence

<400> SEQUENCE: 121
tttctcgtag ctgctgcaac tggagcacac tcccaggagc agctgaagga gtcc         54

<210> SEQ ID NO 122
<211> LENGTH: 36
<212> TYPE: PRT
<213> ORGANISM: Artificial sequence
<220> FEATURE:
<223> OTHER INFORMATION: Synthetic sequence

<400> SEQUENCE: 122

Gly Gly Ala Gly Gly Cys Gly Cys Cys Ala Gly Gly Gly Gly
1               5                   10                  15

Ala Ala Gly Ala Cys Cys Gly Ala Thr Gly Gly Gly Cys Cys Cys Thr
            20                  25                  30

Thr Gly Gly Thr
        35

<210> SEQ ID NO 123
<211> LENGTH: 54
<212> TYPE: DNA
<213> ORGANISM: Artificial sequence
<220> FEATURE:
<223> OTHER INFORMATION: Synthetic sequence

<400> SEQUENCE: 123
tttctcgtag ctgctgcaac tggagcacac tcctcctatg agctgacaca gctg         54

<210> SEQ ID NO 124
<211> LENGTH: 54
<212> TYPE: DNA
<213> ORGANISM: Artificial sequence
<220> FEATURE:
<223> OTHER INFORMATION: Synthetic sequence

<400> SEQUENCE: 124
tttctcgtag ctgctgcaac tggagcacac tcccagtttg tgctgactca gtcg         54
```

```
<210> SEQ ID NO 125
<211> LENGTH: 54
<212> TYPE: DNA
<213> ORGANISM: Artificial sequence
<220> FEATURE:
<223> OTHER INFORMATION: Synthetic sequence

<400> SEQUENCE: 125
tttctcgtag ctgctgcaac tggagcacac tccgaccct a tgctgaccca gact      54

<210> SEQ ID NO 126
<211> LENGTH: 54
<212> TYPE: DNA
<213> ORGANISM: Artificial sequence
<220> FEATURE:
<223> OTHER INFORMATION: Synthetic sequence

<400> SEQUENCE: 126
tttctcgtag ctgctgcaac tggagcacac tccgaccctg tgctgaccca gact      54

<210> SEQ ID NO 127
<211> LENGTH: 30
<212> TYPE: DNA
<213> ORGANISM: Artificial sequence
<220> FEATURE:
<223> OTHER INFORMATION: Synthetic sequence

<400> SEQUENCE: 127
ggcctcgagt tatgaacatt ctgtaggggc                                  30

<210> SEQ ID NO 128
<211> LENGTH: 30
<212> TYPE: DNA
<213> ORGANISM: Artificial sequence
<220> FEATURE:
<223> OTHER INFORMATION: Synthetic sequence

<400> SEQUENCE: 128
ggcctcgagt taacactctc ccctgttgaa                                  30

<210> SEQ ID NO 129
<211> LENGTH: 342
<212> TYPE: DNA
<213> ORGANISM: Oryctolagus cuniculus

<400> SEQUENCE: 129
cagtcagtga aggagtccga gggaggtctc ttcaagccaa cggatacct gacactcacc  60 tgcacagtct ctggattctc cctcagtagc tatggagtga cctgggtccg ccaggctcca 120
gggagcgggc tggaatggat cggatacatt aatactgctg gtaacacata ctacgcgagc 180
tgggcgaaaa gccggtccac catcaccagg aacaccaacg agaacacggt gactctgaaa 240
atgaccagtc tgacagccgc ggacacggcc acctatttct gtgcgagaga ttggacatcc 300
cttaacatct ggggaccagg gaccctcgtc accgtctctt ca                   342

<210> SEQ ID NO 130
<211> LENGTH: 342
<212> TYPE: DNA
<213> ORGANISM: Oryctolagus cuniculus

<400> SEQUENCE: 130
caggagcagc tggaggagtc cgggggtcgc ctggtcacgc ctgggacacc cctgacactc  60
acctgcacag tctctggatt ctccctcagt agctactgga tgagctgggt ccgccaggct 120
```

```
ccagggaagg ggctggaatg gatcgggacc attacgcctg gtggtaacac ggactacgcg    180
acctgggcga aagcccgatt caccgtctcc aaaacctcga ccacggtgga tctaaaaatc    240
accagtccga caaccgagga cacggccacc tatttctgtg ccagagggat aggtggtgct    300
gctgacttgt gggggccagg caccctggtc accatctcct ca                      342
```

<210> SEQ ID NO 131
<211> LENGTH: 363
<212> TYPE: DNA
<213> ORGANISM: Oryctolagus cuniculus

<400> SEQUENCE: 131

```
cagtcagtga aggagtccga gggaggtctc ttcaagccaa cggatagcct gacactcacc    60
tgcacagtct ctggattctc cctcagtacc tatggagtga gctgggtccg ccaggctcca   120
gggaacgggc tggaatggat cggggccatt ggtagtagtg gtagcgcaaa ctacgcgagc   180
tgggcgaaag accgatccac catcaccaga aacaccaacc tgaacacggt gactctgaaa   240
atgaccagtc tgacagccgc ggacacggcc acctatttct gtgcgagaga tggttactat   300
agtagtggct gggtcccta ctttaacatc tgggggccag gcaccctggt caccatctcc   360
tca                                                                 363
```

<210> SEQ ID NO 132
<211> LENGTH: 330
<212> TYPE: DNA
<213> ORGANISM: Oryctolagus cuniculus

<400> SEQUENCE: 132

```
gaccctatgc tgacccagac tccatcctcc acgtctaccg ctgtgggaga cacagtcacc    60
atcaagtgcc aggctagtca gagcattagt agtgacttat cctggtatca gcagaaacca   120
gggcagcgtc ccaagctcct gatctaccag gcatccactc tggcatctgg ggtcccatcg   180
cggttcaaag gcagtggata tgggacagag tacactctca ccatcagcgg cgtgcagcgt   240
gaggatgctg ccatctacta ctgtctaggt ggttatgctg atgcttctta tcgaactgct   300
ttcggcggag gaaccaagct ggagatcaaa                                    330
```

<210> SEQ ID NO 133
<211> LENGTH: 330
<212> TYPE: DNA
<213> ORGANISM: Oryctolagus cuniculus

<400> SEQUENCE: 133

```
caagtgctga cccagactcc atcctccacg tctgccgctg tgggaggcac agtcaccatc    60
aagtgccagg ccagtcagag cattagtagt agcgacttat cctggtatca gcagaaacca   120
gggcagcctc ccaagctcct gatctatgct acatcctatc tggcatctgg agtcccatcg   180
cggttcaaag gcagtggatc tgggacagag tacactctca ccatcagcgg cgtgcagcgt   240
gaggatgctg ccacctacta ctgtctaggt ggttatccta atacttctta ccggtctgct   300
ttcggcggag ggaccaaggt ggagatcaaa                                    330
```

<210> SEQ ID NO 134
<211> LENGTH: 333
<212> TYPE: DNA
<213> ORGANISM: Oryctolagus cuniculus

<400> SEQUENCE: 134

```
tccttcgtgc tgactcagcc agcctcagtg caggtgaact gggacagac ggtctccctc    60
```

```
acatgcactg cagatacact gagcagaagt tatgcttcct ggtaccagca gaagccaggc    120
caggcccctg tgctgctcat ctacagggat accagtcggc cctcagggct ccctgaccgc    180
ttctctggct ccagctcagg gaacacggcc accctgacca tcagtggggc ccaggctggg    240
gacgaggctg actactattg tgctacaagc ggtggcagtg gcagcaaccc tcagtatgtg    300
ttcggcggag ggacccagct gaccgtcaca ggc                                 333
```

<210> SEQ ID NO 135
<211> LENGTH: 449
<212> TYPE: PRT
<213> ORGANISM: Artificial sequence
<220> FEATURE:
<223> OTHER INFORMATION: Synthetic sequence

<400> SEQUENCE: 135

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
            305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 136
<211> LENGTH: 214
<212> TYPE: PRT
<213> ORGANISM: Artificial sequence
<220> FEATURE:
<223> OTHER INFORMATION: Synthetic sequence

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 137
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 137

Leu Pro Xaa Ser Gly
1               5

<210> SEQ ID NO 138
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 138

Leu Pro Xaa Ala Gly
1               5

<210> SEQ ID NO 139
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 139

Leu Pro Xaa Thr Gly
1               5

<210> SEQ ID NO 140
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 140

Leu Ala Xaa Thr Gly
1               5

<210> SEQ ID NO 141
<211> LENGTH: 5
<212> TYPE: PRT
<213> ORGANISM: Artificial sequence
<220> FEATURE:
<223> OTHER INFORMATION: Synthetic sequence

<400> SEQUENCE: 141
```

```
Asn Pro Gln Thr Gly
1               5

<210> SEQ ID NO 142
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 142

Leu Pro Xaa Thr
1
```

ROR2 ANTIBODY COMPOSITIONS AND RELATED METHODS

CROSS-REFERENCE TO RELATED APPLICATIONS

The subject patent application is a divisional of U.S. patent application Ser. No. 16/071,361 (filed Jul. 19, 2018; now pending), which is a § 371 U.S. national phase filing of PCT International Patent Application No. PCT/US2017/014370 (filed Jan. 20, 2017; now expired), which claims the benefit of priority to U.S. Provisional Patent Application No. 62/280,834 (filed Jan. 20, 2016). The full disclosures of the priority applications are incorporated herein by reference in their entirety and for all purposes.

BACKGROUND OF THE INVENTION

Cancer is one of the leading causes of death. It is a class of diseases which is caused by malignant transformation of healthy cells, caused by genetic alterations, like chromosomal translocations, mutations in tumor suppressor genes, transcription factors or growth-factor receptors, leading to the immortalization of the cells. If the immortalization is combined with excessive proliferation the immortalized cells generate tumors with or without metastasis (in case of solid tumors) or leukemias and lymphomas (cancers of the blood). Defective apoptosis, or programmed cell death, can further contribute to malignant transformation of cells leading to cancer.

A family of membrane associated receptor tyrosine kinases, consisting of the receptor tyrosine kinase orphan receptors-1 and -2 (ROR1 and ROR2) have been described as being specifically associated with particular cancers (Rebagay et al. (2012) *Front Oncol.* 2(34)), while being largely absent in expression on healthy tissue with, at least in case of ROR1, few exceptions (Balakrishnan et al. (2016) *Clin Cancer Res.* doi: 10.1158/1078-0432). Whether or not ROR expression is functionally associated with tumorigenesis remains unclear. However, due to the very tumor-selective expression of the ROR family members, they represent relevant targets for targeted cancer therapies. Importantly, ROR2 is expressed on the tumor cell surface in neuroblastoma, osteosarcoma, renal cell carcinoma, breast cancer, gastric cancer, prostate cancer, melanoma, squamous cell carcinoma, multiple myeloma and other cancers.

In normal physiology, ROR2 is responsible for aspects of bone and cartilage growth during embryonic development. After birth expression of ROR2 is downregulated and ROR2 is normally undetectable or expressed at very low levels in adult tissues. Weak expression of ROR2 has only been reported in stomach and thyroid issue (Morioka et al., Cancer Sci. 100: 1227-1233, 2009). ROR2 has previously been recognized as a target for the development of ROR2 specific antibodies (WO2013103637). However, there are no antibodies against the hROR2 target with known sequences described in the literature.

Therefore, there is a need for high-quality anti-ROR2 binding antibodies that can be used as a basis for the development of antibody-based targeted therapies of ROR2 expressing cancers. There is also a need for additional diagnostic tools for detecting ROR2 expressions in ROR2-related disease conditions, e.g. such as Western-blotting and or immunohistochemistry (IHC). The instant invention is directed to addressing these and other needs.

SUMMARY OF THE INVENTION

In one aspect, the invention provides novel, high-affinity binding domains of rabbit antibodies that specifically bind to the extracellular domain of human receptor tyrosine kinase-like orphan receptor 2 (hROR2) and that have been selected from highly diverse phage-display libraries of non-immunized rabbits using human ROR2 (hROR2) extracellular domains expressed in mammalian cells as a bait. The variable regions of rabbit antibodies have been selected by screening for the binding against the ECD of hROR2 both as recombinant proteins and also based on the binding of hROR2 over-expressed on the surface of mammalian host cells. By this strategy novel antibodies for hROR2 of high quality and favorable functional properties have been identified. Furthermore, the invention provides chimeric full-length antibodies of the rabbit variable domains fused to the constant region domains of human $IgG_1$ antibodies.

In a second aspect of the invention site-specifically conjugated antibody drug conjugates (ADCs) based on the chimeric rabbit-human anti-human ROR2 (hROR2) antibodies with an ultra-potent anthracycline toxin are provided by the invention. The site-specific conjugation is achieved by enzymatic conjugation using sortase enzyme, essentially as disclosed in WO2014140317. The ultra-potent anthracycline toxin resulting in anti-hROR2 ADCs with high potency in vitro has been disclosed in WO2016102679, which is incorporated by reference herein.

Lastly, the invention provides chimeric antigen receptors (CARs) and T cells engineered with these CARs, i.e. so-called CAR-T cells, employing said anti-hROR2 binding domains showing high efficacy in vitro.

Therefore the invention relates to anti-hROR2 antibodies, antibody-based binding proteins, antibody fragments (antigen-binding fragments) thereof, antibody drug conjugates (ADCs), or CARs having the same binding specificity for hROR2 as that of hROR2 specific antibodies containing an immunoglobulin heavy chain variable region sequence and an immunoglobulin light chain variable region sequence, respectively, shown in (i) SEQ ID NO:1 and SEQ ID NO:13; (ii) SEQ ID NO:2 and SEQ ID NO:14; (iii) SEQ ID NO:3 and SEQ ID NO:15; (iv) SEQ ID NO:4 and SEQ ID NO:16; (v) SEQ ID NO:5 and SEQ ID NO:17; (vi) SEQ ID NO:6 and SEQ ID NO:18; (vii) SEQ ID NO:7 and SEQ ID NO:19; (vii) SEQ ID NO:8 and SEQ ID NO:20; (ix) SEQ ID NO:9 and SEQ ID NO:21; (x) SEQ ID NO:10 and SEQ ID NO:22; (xi) SEQ ID NO:11 and SEQ ID NO:23; or (xii) SEQ ID NO:12 and SEQ ID NO:24.

The invention further relates to anti-hROR2 antibodies, antibody-based binding proteins, antibody fragments thereof, antibody drug conjugates (ADCs), or CARs comprising a heavy chain variable region sequence or a light chain variable region sequence, one or both of which are at least 90%, or at least 95% or greater than 95%, but less than 100% identical, to a heavy chain variable region sequence or a light chain variable region sequence respectively shown in (i) SEQ ID NO:1 and SEQ ID NO:13; (ii) SEQ ID NO:2 and SEQ ID NO:14; (iii) SEQ ID NO:3 and SEQ ID NO:15; (iv) SEQ ID NO:4 and SEQ ID NO:16; (v) SEQ ID NO:5 and SEQ ID NO:17; (vi) SEQ ID NO:6 and SEQ ID NO:18; (vii) SEQ ID NO:7 and SEQ ID NO:19; (vii) SEQ ID NO:8 and SEQ ID NO:20; (ix) SEQ ID NO:9 and SEQ ID NO:21; (x) SEQ ID NO:10 and SEQ ID NO:22; (xi) SEQ ID NO:11 and SEQ ID NO:23; or (xii) SEQ ID NO:12 and SEQ ID NO:24.

The invention further relates to anti-hROR2 antibodies, antibody-based binding proteins, antibody fragments thereof, antibody drug conjugates (ADCs), or CARs comprising a heavy chain variable region sequence or a light chain variable region sequence, one or both of which are identical to a heavy chain variable region sequence and a light chain variable region sequence respectively shown in (i) SEQ ID NO:1 and SEQ ID NO:13; (ii) SEQ ID NO:2 and SEQ ID NO:14; (iii) SEQ ID NO:3 and SEQ ID NO:15; (iv) SEQ ID NO:4 and SEQ ID NO:16; (v) SEQ ID NO:5 and SEQ ID NO:17; (vi) SEQ ID NO:6 and SEQ ID NO:18; (vii) SEQ ID NO:7 and SEQ ID NO:19; (vii) SEQ ID NO:8 and SEQ ID NO:20; (ix) SEQ ID NO:9 and SEQ ID NO:21; (x) SEQ ID NO:10 and SEQ ID NO:22; (xi) SEQ ID NO:11 and SEQ ID NO:23; or (xii) SEQ ID NO:12 and SEQ ID NO:24.

The invention further relates to anti-hROR2 antibodies, antibody-based binding proteins, antibody fragments thereof, antibody drug conjugates (ADCs), or CARs comprising immunoglobulin heavy chain CDR sequences and immunoglobulin light chain CDR sequences that are at least 90%, or at least 95% or greater than 95%, but less than 100% identical, respectively, to (i) SEQ ID NOs:25-27 and SEQ ID NOs:61-63, (ii) SEQ ID NOs:28-30 and SEQ ID NOs:64-66, (iii) SEQ ID NOs:31-33 and SEQ ID NOs:67-69, (iv) SEQ ID NOs:34-36 and SEQ ID NOs:70-72, (v) SEQ ID NOs:37-39 and SEQ ID NOs:73-75, (vi) SEQ ID NOs:40-42 and SEQ ID NOs:76-78, (vii) SEQ ID NOs:43-45 and SEQ ID NOs:79-81, (viii) SEQ ID NOs:46-48 and SEQ ID NOs:82-84, (ix) SEQ ID NOs:49-51 and SEQ ID NOs:85-87, (x) SEQ ID NOs:52-54 and SEQ ID NOs:88-90, (xi) SEQ ID NOs:55-57 and SEQ ID NOs:91-93, or (xii) SEQ ID NOs:58-60 and SEQ ID NOs:94-96.

The invention further relates to anti-hROR2 antibodies, antibody-based binding proteins, antibody fragments thereof, antibody drug conjugates (ADCs), or CARs of the invention that contain heavy chain CDR1-3 sequences or light chain CDR1-3 sequences that are identical, respectively, to (i) SEQ ID NOs:25-27 and SEQ ID NOs:61-63, (ii) SEQ ID NOs:28-30 and SEQ ID NOs:64-66, (iii) SEQ ID NOs:31-33 and SEQ ID NOs:67-69, (iv) SEQ ID NOs:34-36 and SEQ ID NOs:70-72, (v) SEQ ID NOs:37-39 and SEQ ID NOs:73-75, (vi) SEQ ID NOs:40-42 and SEQ ID NOs: 76-78, (vii) SEQ ID NOs:43-45 and SEQ ID NOs:79-81, (viii) SEQ ID NOs:46-48 and SEQ ID NOs:82-84, (ix) SEQ ID NOs:49-51 and SEQ ID NOs:85-87, (x) SEQ ID NOs: 52-54 and SEQ ID NOs:88-90, (xi) SEQ ID NOs:55-57 and SEQ ID NOs:91-93, or (xii) SEQ ID NOs:58-60 and SEQ ID NOs:94-96.

The invention further relates to anti-hROR2 antibodies, antibody-based binding proteins, antibody fragments thereof, antibody drug conjugates (ADCs), or CARs of the invention that contain a heavy chain variable region sequence and a light chain variable region sequence respectively shown in (i) SEQ ID NO:1 and SEQ ID NO:13; (ii) SEQ ID NO:2 and SEQ ID NO:14; (iii) SEQ ID NO:3 and SEQ ID NO:15; (iv) SEQ ID NO:4 and SEQ ID NO:16; (v) SEQ ID NO:5 and SEQ ID NO:17; (vi) SEQ ID NO:6 and SEQ ID NO:18; (vii) SEQ ID NO:7 and SEQ ID NO:19; (vii) SEQ ID NO:8 and SEQ ID NO:20; (ix) SEQ ID NO:9 and SEQ ID NO:21; (x) SEQ ID NO:10 and SEQ ID NO:22; (xi) SEQ ID NO:11 and SEQ ID NO:23; or (xii) SEQ ID NO:12 and SEQ ID NO:24.

The invention further relates to anti-hROR2 antibodies, antibody-based binding proteins, antibody fragments thereof, antibody drug conjugates (ADCs), or CARs of the invention that contain at least one heavy chain CDR sequence selected from the group consisting of SEQ ID NOs:25-60. Some of these molecules further contain a light chain CDR sequence selected from the group consisting of SEQ ID NOs:61-96.

The invention further relates to anti-hROR2 antibodies, antibody-based binding proteins, antibody fragments thereof, antibody drug conjugates (ADCs), or CARs that contain heavy chain CDR1, CDR2, and CDR3 sequences that are respectively identical to SEQ ID NOs:25-27, SEQ ID NOs:28-30, SEQ ID NOs:31-33, SEQ ID NO:34-36, SEQ ID NOs:37-39, SEQ ID NOs:40-42, SEQ ID NOs:43-45, SEQ ID NOs:46-48, SEQ ID NOs:49-51, SEQ ID NOs:52-54, SEQ ID NOs:55-57, or SEQ ID NOs:58-60.

The invention further relates to anti-hROR2 antibodies, antibody-based binding proteins, antibody fragments thereof, antibody drug conjugates (ADCs), or CARs of the invention that contain at least one light chain CDR sequence selected from the group consisting of SEQ ID NOs:61-96. Some of these molecules additionally contain a heavy chain CDR sequence selected from the group consisting of SEQ ID NOs:25-60.

The invention further relates to anti-hROR2 antibodies, antibody-based binding proteins, antibody fragments thereof, antibody drug conjugates (ADCs), or CARs that contain light chain CDR1, CDR2, and CDR3 sequences that are respectively identical to SEQ ID NOs:61-63, SEQ ID NOs:64-66, SEQ ID NOs:67-69, SEQ ID NOs:70-72, SEQ ID NOs:73-75, SEQ ID NOs:76-78, SEQ ID NOs:79-81, SEQ ID NOs:82-84, SEQ ID NOs:85-87, SEQ ID NOs:88-90, SEQ ID NOs:91-93, or SEQ ID NOs:94-96.

The invention further relates to anti-hROR2 antibodies, antibody-based binding proteins, antibody fragments thereof, antibody drug conjugates (ADCs), or CARs that contain heavy chain CDR1, CDR2 and CDR3 sequences and light chain CDR1, CDR2 and CDR3 sequences respectively shown in (i) SEQ ID NOs:25-27 and SEQ ID NOs:61-63, (ii) SEQ ID NOs:28-30 and SEQ ID NOs:64-66, (iii) SEQ ID NOs:31-33 and SEQ ID NOs:67-69, (iv) SEQ ID NOs: 34-36 and SEQ ID NOs:70-72, (v) SEQ ID NOs:37-39 and SEQ ID NOs:73-75, (vi) SEQ ID NOs:40-42 and SEQ ID NOs:76-78, (vii) SEQ ID NOs:43-45 and SEQ ID NOs:79-81, (vii) SEQ ID NOs:46-48 and SEQ ID NOs:82-84, (ix) SEQ ID NOs:49-51 and SEQ ID NOs:85-87, (x) SEQ ID NOs:52-54 and SEQ ID NOs:88-90, (xi) SEQ ID NOs:55-57 and SEQ ID NOs:91-93, or (xii) SEQ ID NOs:58-60 and SEQ ID NOs:94-96.

In various embodiments, the anti-hROR2 antibodies, antibody-based binding proteins, antibody fragments thereof of the invention can be either of IgA1, IgA2, IgD, IgE, IgG1, IgG2, IgG3, IgG4 or IgM isotypes, or F(ab)2, Fv, scFv, IgGACH2, F(ab')2, scFv2CH3, Fab, VL, VH, scFv4, scFv3, scFv2, dsFv, Fv, scFv-Fc, (scFv)2 fragments thereof, or non-depleting IgG, a diabody, or a bivalent antibody. In some embodiments, the anti-hROR2 antibodies or antibody-based binding proteins is an IgG selected from the group consisting of naturally occurring IgG1, IgG2, IgG3, IgG4 isotypes, or synthetic IgGs. In some other embodiments, the anti-hROR2 antibody fragment is a Fab, a scFv, or a dsFv. In some embodiments, the anti-hROR2 antibodies, antibody-based binding proteins, antibody fragments thereof are conjugated to a synthetic molecule. In some of these embodiments, the anti-hROR2 antibodies, antibody-based binding proteins, antibody fragments thereof are conjugated to a transmembrane region and an intracellular T-cell receptor (TCR) signaling domain to form a chimeric antigen receptor (CAR).

The invention further relates to antibody drug conjugates (ADCs) comprising a hROR2-specific antibody, antibody-based binding protein or antibody fragment of the invention with a toxin payload that effects killing of hROR2 specific cells. In said ADCs the toxin payload can be conjugated non-site-specifically to the antibody, antibody-based binding protein or antibody fragment via lysine or cysteine amino acid side chains employing classical chemical linkers with maleimide functionality, or other chemical known in the art that can mediate conjugation to lysine or cysteine amino acid side chains. In said ADCs the small molecular weight payload can also be conjugated site-specifically either by chemical, chemo-enzymatic, or enzymatic conjugations known in the art, like e.g. with bifunctional linkers, linkers allowing Pictet-Spengler chemistry on formyl-glycine forming enzyme modified antibodies, by glycan-remodeled antibodies, or by bacterial transglutaminase or sortase enzymes In a related aspect, the invention provides pharmaceutical compositions that contain a therapeutically effective amount of an anti-hROR2 antibody, antibody-based binding protein, antibody fragment thereof, antibody drug conjugate (ADC) of the invention and a pharmaceutically acceptable carrier. Also provided in the invention are pharmaceutical combinations or kits that contain at least one of the antibody, antibody-based binding proteins, antibody fragments thereof or antibody drug conjugates (ADCs) disclosed herein. Further provided in the invention are isolated or substantially purified polynucleotides that encode the variable region of the immunoglobulin heavy chain or immunoglobulin light chain of the anti-hROR2 antibodies, antibody-based binding proteins, antibody fragments thereof, antibody drug conjugates (ADCs), or CARs disclosed herein, as well as expression vectors harboring such a polynucleotide sequence.

In another aspect, the invention provides methods of killing or inhibiting the growth of a cell expressing hROR2 in a subject. The methods entail administering a therapeutically effective amount of an anti-hROR2 antibody, antibody-based binding protein, antibody fragment thereof, antibody drug conjugate (ADC), or CAR disclosed herein to a subject in need of treatment. This enables killing or inhibiting the growth of the cell expressing hROR2 in the subject. In various embodiments, the cell expressing hROR2 is a tumor cell. In a related aspect, the invention provides methods of treating a disease or condition associated with elevated expression of hROR2 in a subject. These methods involve administering a therapeutically effective amount of an anti-hROR2 antibody, antibody-based binding protein, antibody fragment thereof, antibody drug conjugate (ADC), or CAR of the invention to a subject that is afflicted with a disease or condition associated with elevated expression of hROR2. This enables treatment of the disease or condition in the subject. Some of these methods are directed to treating a cancer in the subject. Cancers that are amendable to treatment with methods of the invention include, e.g., neuroblastoma, osteosarcoma, renal cell carcinoma, breast cancer, gastric cancer, prostate cancer, melanoma, squamous cell carcinoma and multiple myeloma. In various embodiments, the administered anti-hROR2 antibody, antibody-based binding protein, antibody fragment thereof, or the antibody drug conjugates (ADC) or CARs based thereon, are F(ab)2, Fv, scFv, IgGACH2, F(ab')2, scFv2CH3, Fab, VL, VH, scFv4, scFv3, scFv2, dsFv, Fv, (scFv)2, or a synthetic IgG. In some methods, the administered anti-hROR2 antibody, antibody-based binding protein or antibody fragment thereof is conjugated to a synthetic molecule. In some of these embodiments, the anti-hROR2 antibody, antibody-based binding protein, antibody fragment thereof is conjugated to a transmembrane region and an intracellular T-cell receptor (TCR) signaling domain to form a chimeric antigen receptor (CAR). In some embodiments, the chimeric antigen receptor (CAR) is present on a T cell to be administered to the subject. In some other embodiments, the antibody can be conjugated to a cytotoxic agent, a radioisotope, or a liposome.

In another aspect, the invention provides methods for detecting an altered ROR2 level in a subject. The methods involve (a) obtaining a biological sample from the subject, (b) contacting the sample with an anti-hROR2 antibody, antibody-based binding protein, antibody fragment thereof disclosed herein, (c) determining the level of ROR2 in the biological sample, and (d) comparing the level of ROR2 in the biological sample to a control level of ROR2. This allows determination of whether the ROR2 level in the biological sample is altered relative to the control level of ROR2. In these methods, an increased ROR2 level in the subject relative to the control level is indicative of a disease or condition associated with elevated expression of ROR2 in the subject. For example, detection of elevated ROR2 expression can be indicative of the presence of neuroblastoma, osteosarcoma, renal cell carcinoma, breast cancer, gastric cancer, prostate cancer, melanoma, squamous cell carcinoma, or multiple myeloma in the subject.

In still another aspect, the invention provides methods for detecting an ROR2-expressing tumor in a subject. These methods entail (a) administering an anti-hROR2 antibody, antibody-based binding protein, antibody fragment thereof of the invention to a subject that has, is suspected to have, or is at risk of developing an ROR2-expressing tumor, and (b) imaging the subject for a region of altered conjugated label density or concentration, wherein the density or concentration is relative to (i) background in proximal tissue or (ii) the density or concentration previously detected in the same region of the subject. The existence of a region of altered conjugated label density or concentration is an indication of the presence of an ROR2-expressing tumor in the subject.

A further understanding of the nature and advantages of the present invention may be realized by reference to the remaining portions of the specification and claims.

DESCRIPTION OF THE DRAWINGS

FIG. 1 shows amino acid sequences of variable immunoglobulin heavy and light chains of novel rabbit anti-hROR2 mAbs as indicated. The amino acid sequence alignment of the rabbit variable domains ($V_\kappa$, $V_\lambda$, and $V_H$) clones is shown with framework regions (FR) and complementarity determining regions (CDR) using Kabat numbering. Shown in the figure are the heavy chain variable domain sequences (SEQ ID NOs:1-12, respectively) and the light chain variable domain sequences (SEQ ID NOs:13-24, respectively) of 12 antibodies designated XBR2-401, XBR2-416, XBR2-433, XBR2-327, XBR2-TOP9, XBR2-TOP72, ERR2-302, ERR2-308, ERR2-316, ERR2-317, ERR2-TOP2, and ERR2-TOP35. As indicated in the figure, clones XBR2-401, XBR2-416, XBR2-327, XBR2-TOP9, ERR2-308, ERR2-316, ERR2-317, and ERR2-TOP2 comprise variable domains of immunoglobulin κ light chains, while antibodies XBR2-433, XBR2-TOP72, ERR2-302, and ERR2-TOP35 comprise variable domains of immunoglobulin λ light chains.

DETAILED DESCRIPTION

I. Overview

Receptor tyrosine kinase orphan receptors-1 and -2, ROR1 and ROR2, are the only two family members defining a new receptor tyrosine kinase family, based on the overall structural design and some functional similarities. Both ROR1 and ROR2 proteins are type I-single pass trans-membrane receptors with an extracellular domain (ECD) consisting of an immunoglobulin domain, a cysteine rich frizzled domain and a Kringle domain. These three extra-cellular domains are followed by a trans-membrane domain connecting the ECD to an intracellular portion of the protein comprising kinase domains (Rabagay et al. (2012) Frontiers Oncol. 2: 1-8).

The human ROR1 and ROR2 proteins are 58% homologous between each other, but each of the ROR proteins is highly conserved between species. This represents a challenge for the development of human ROR2 specific monoclonal antibodies and very few antibodies are known, and no sequences of anti-ROR2 antibodies have been described in the literature.

In order to develop anti-hROR2 antibodies, the present inventors have generated a very high-complexity naïve rabbit antibody Fab library displayed by phage and selected this library for binders to the mammalian cell expressed human ECD of hROR2 and to cell-surface expressed human ROR2, in order to select most functional and diverse antibody clones reactive with native human ROR2 protein.

This strategy was chosen, because the antibody repertoire to be mined is still derived from natural rabbit B lymphocytes and thus selected for immune-system pre-selected antibody heavy and light chains. However, due to the applied screening strategy involving native recombinant and cell-expressed human ROR2 it was the hope that hROR2 specific antibodies would be identified with high functional qualities that are potentially useful for the therapy of human diseases associated with ROR2 expression, like in particular ROR2-positive cancer.

Figure 2:
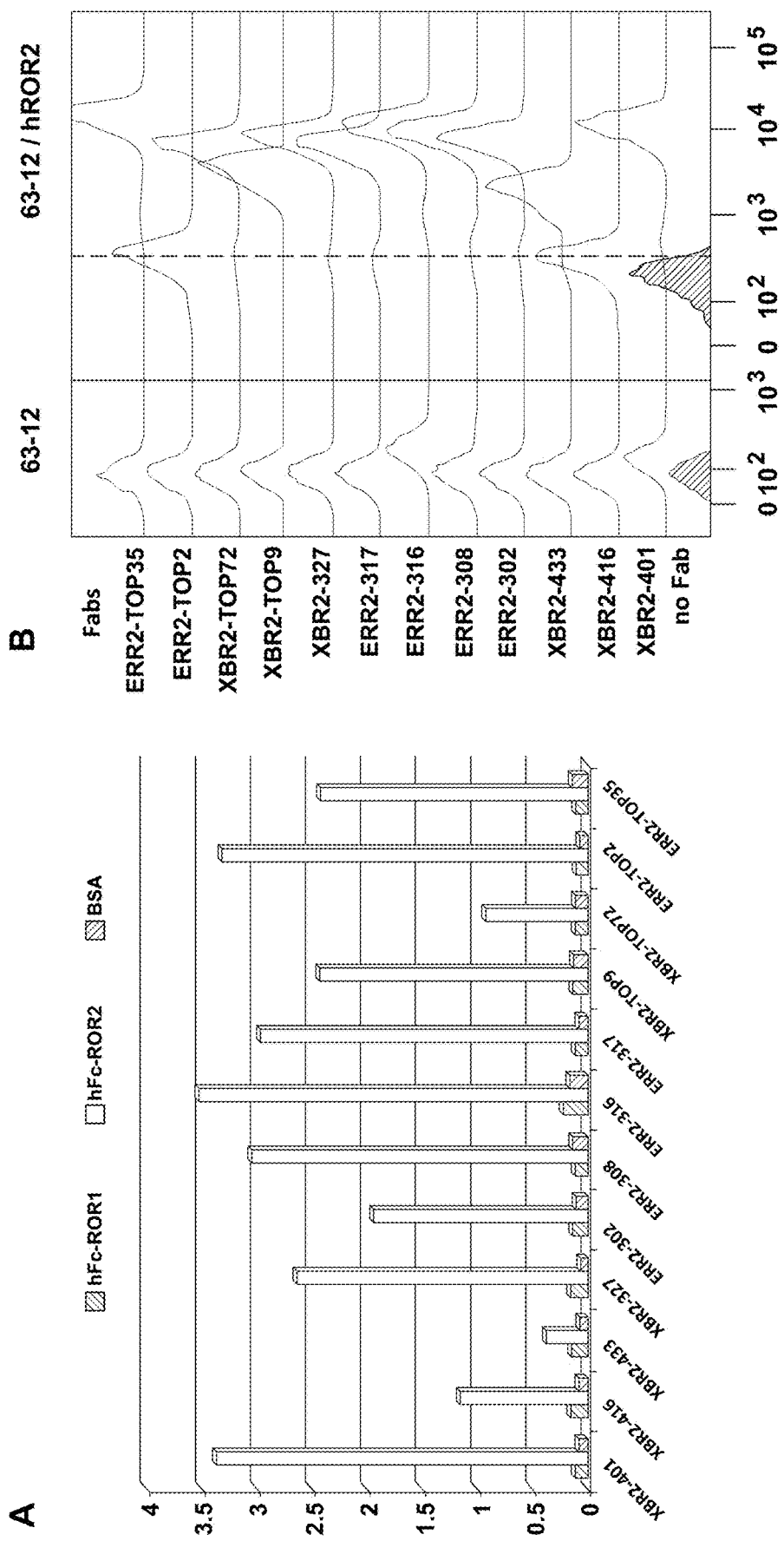
FIG. 2 shows binding activity of chimeric rabbit/human Fabs to ROR2. (A) The binding of each chimeric rabbit/human Fab to immobilized human ROR2 (hFc-hROR2). As controls for the hROR2 specificity, ELISAs with the sister-molecule of ROR2, hROR1 (hFc-hROR1) expressed in mammalian cells and with BSA as an unrelated control were performed with the different novel antibodies identified in the phage-display selection against hFc-hROR2. (B) The panel displays the binding of chimeric rabbit/human Fab to ectopically expressed hROR2 on mouse pre-B cell (63-12) surface as analyzed by flow cytometry.
Figure 3:
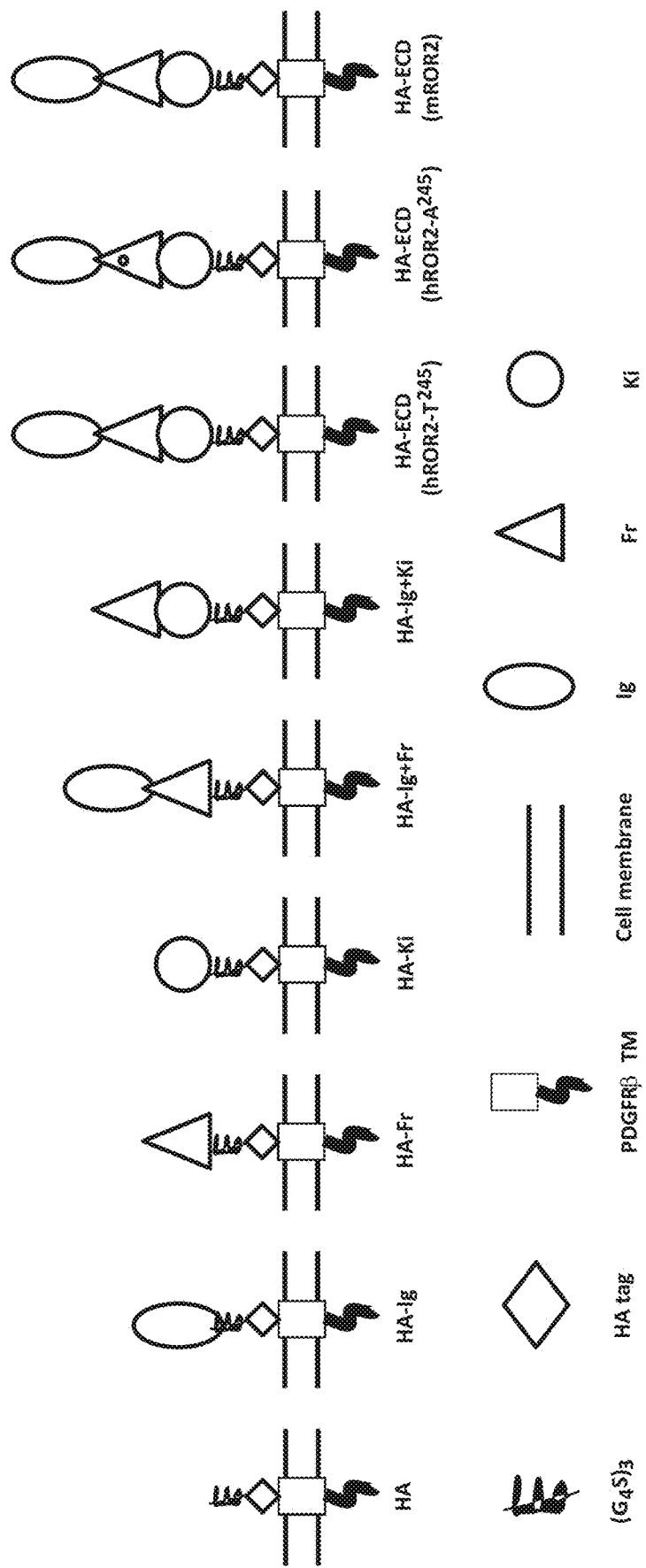
FIG. 3 is a schematic representation of the structure of various hROR2 domain proteins and control proteins displayed on HEK 293F cells for epitope mapping studies of the novel identified antibodies. Eight constructs with different isolated domains of the extracellular domains (ECD) of human ROR2 or control domains, were cloned and stably transfected into HEK 293F cells.
Figure 10:
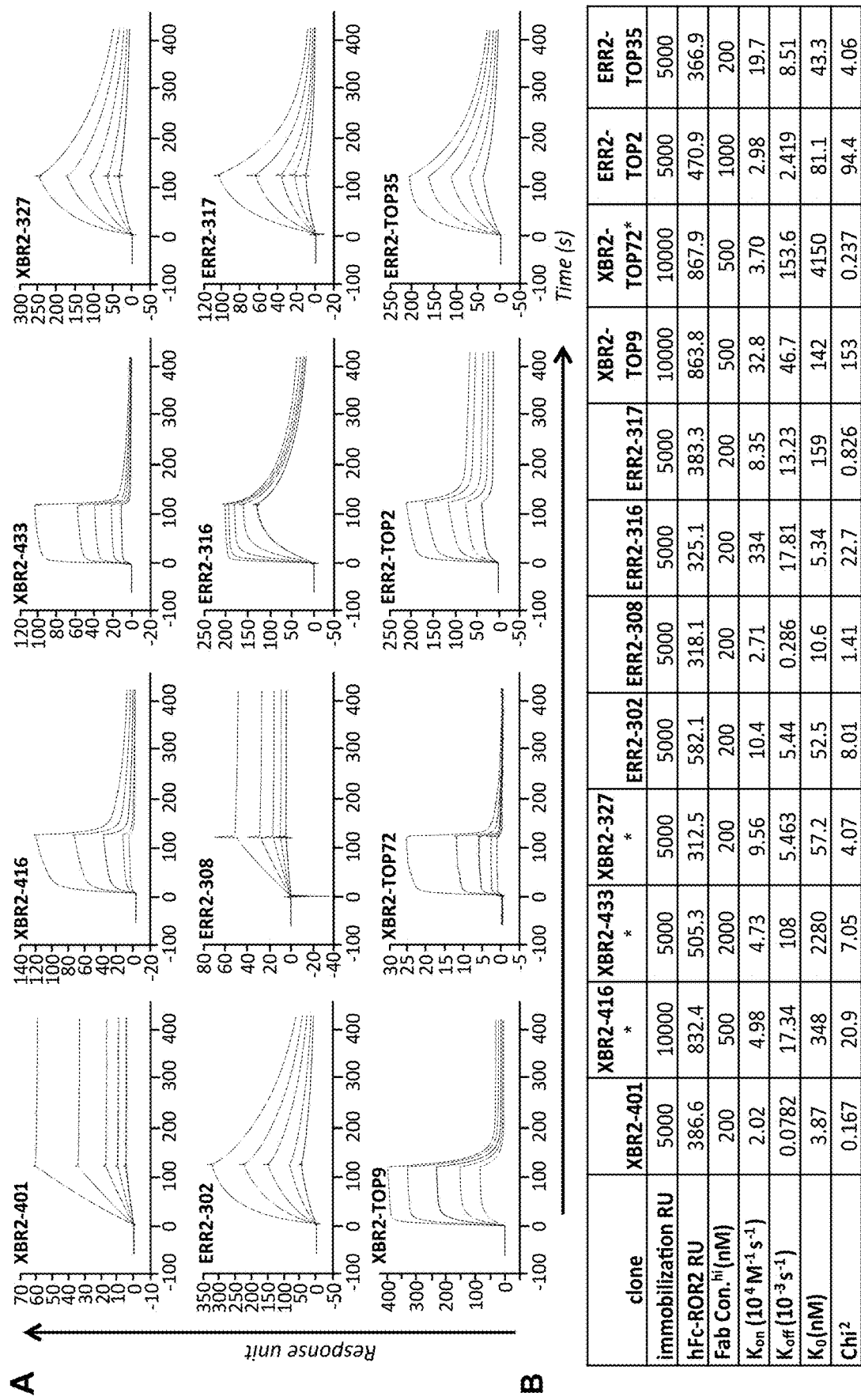
FIG. 10 shows affinity measurements of anti-hROR2 specific Fabs to hROR2 ECD by surface plasmon resonance. (A) Shown are Biacore X100 sensorgrams obtained for the binding of each Fab to Fc-hROR2 captured by anti-human Fc-γ antibody immobilized on a CM5 chip after instantaneous background depletion. Fabs were injected at five different concentrations with the highest concentration indicated in table (B), one of the five concentrations was tested in duplicates. (B) Monovalent affinities of each Fab are shown in the table. The equilibrium dissociation constant ($K_D$) was calculated from $k_{off}/k_{on}$ ($k_{on}$, association rate constant; $k_{off}$, dissociation rate constant).
Figure 11:
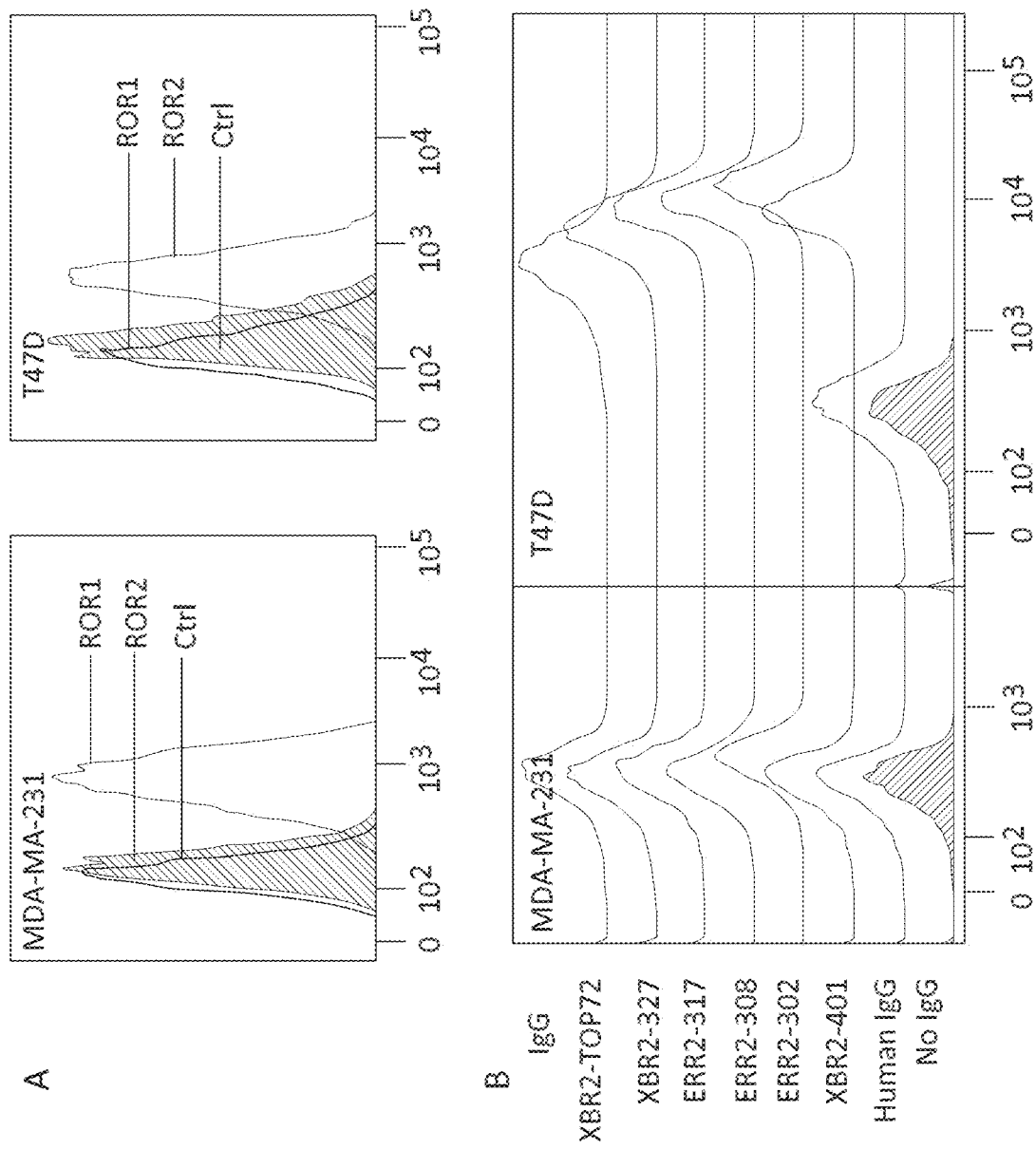
FIG. 11 shows the binding activity of selected chimeric rabbit/human IgG1 to endogenous hROR2 expressed on breast cancer cells measured by flow cytometry. Human breast cancer cell line T47D is known to express hROR2, human breast cancer cell line MDA-MB-231 is known to be negative for hROR2. In contrast, T47D is known to be ROR1 negative, whereas MDA-MB-231 is known to be positive for ROR1 expression. (A) The expression of endogenous hROR2 on breast cancer cells was detected by flow cytometry using commercially available goat anti-human ROR2 polyclonal antibodies (R&D Systems) followed by Alexa Fluor 647-conjugated AffiniPure F(ab')$_2$ donkey anti-goat IgG (H+L) polyclonal antibodies (Jackson ImmunoResearch Laboratories). (B) Binding of chimeric rabbit/human IgG1 to hROR2 was detected by flow cytometry on the cell surface of human T47D breast cancer cells. Human MDA-MB-231 breast cancer cells were used as a negative control cell line.

As a result of the chosen strategy a number of novel rabbit high-affinity anti-human ROR2 antibodies have been identified with diverse CDR1, 2 and 3 sequences (FIG. 1) and with high binding selectivity for human ROR2, but not for its most related "sister molecule", human ROR1 (FIGS. 2 and 3). Some of the hROR2-specific antibodies showed high affinity (single-digit nM affinities) to the hROR2 target (FIG. 10). The invention is predicated in part on the generation by the present inventors of a large naïve chimeric rabbit/human Fab library and selection for binders to human ROR2. As detailed herein, several monoclonal chimeric rabbit/human Fab antibodies (mAbs) were obtained by the inventors (see FIG. 1). These mAbs all bind to purified human ROR2 as analyzed by ELISA and to cell surface human ROR2 as analyzed by flow cytometry. Neither binds to ROR1, which is the closest relative of ROR2 and shares 58% amino acid sequence identity with ROR2. In addition, the affinity of the mAbs and the location of their epitopes (which are different) have been determined. Further, several mAbs (antibody clones XBR2-401, XBR2-416, XBR2-433, ERR2-302, ERR2-308, ERR2-317, XBR2-327, and XBR2-TOP72) were also converted to the chimeric rabbit/human IgG1 format, expressed in mammalian cells, and purified by Protein A affinity chromatography. Binding activities of these IgG1 antibodies were also determined.

In addition to this, several, mAbs were expressed as chimeric rabbit/human IgG1 with C-terminal sortase-recognition tags, allowing site-specific conjugation of payloads to the antibody C-termini by sortase-enzyme mediated antibody conjugation technology (SMAC-Technology™) essentially as described in WO2014140317. These anti-hROR2 antibodies have then been site-specifically conjugated to a highly potent anthracycline-based PNU-159682 toxin derivative, Gly$_5$-EDA-PNU (FIG. 13), in order to generate antibody drug conjugates (ADCs), essentially as disclosed in WO2016102679 (which is incorporated by reference herein). These ADCs have functionally been evaluated in vitro, and all have been found to effectively kill mouse breast cancer cells ectopically expressing human ROR2.

Figure 16:
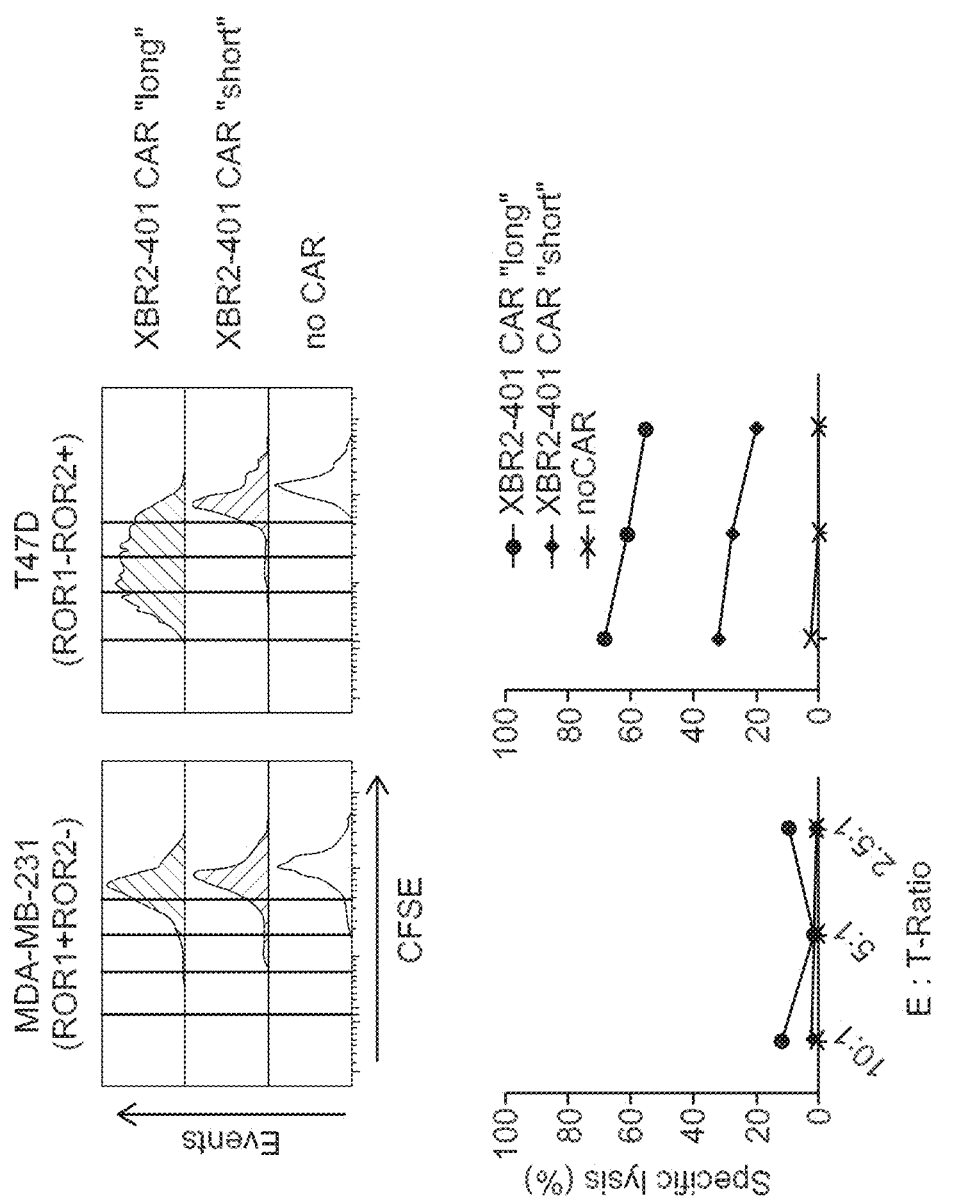
FIG. 16 shows a comparison of the in vitro activities of ROR2-targeting XBR2-401 CAR-T cells on ROR2 negative human breast cancer cells MDA-MB-231, and on ROR2 positive human breast cancer cells T47D with short and long spacer. The upper panels show the cellular proliferation of T cells with or without CARs (long and short spacer) as indicated upon co-culture with ROR2 negative MDA-MB-231 and ROR2 positive T47D cells and as analyzed by CFSE staining. Only ROR2 positive T47D cells induce very strong proliferation of T cells engineered with a ROR2 CAR with long spacer. The lower panels show the corresponding cell killing activity at different effector-target ratios of CAR T cells to breast cancer target cells as indicated. Also this data set shows strongest activity of the T cells with a ROR2 CAR having a long spacer.
Figure 17:
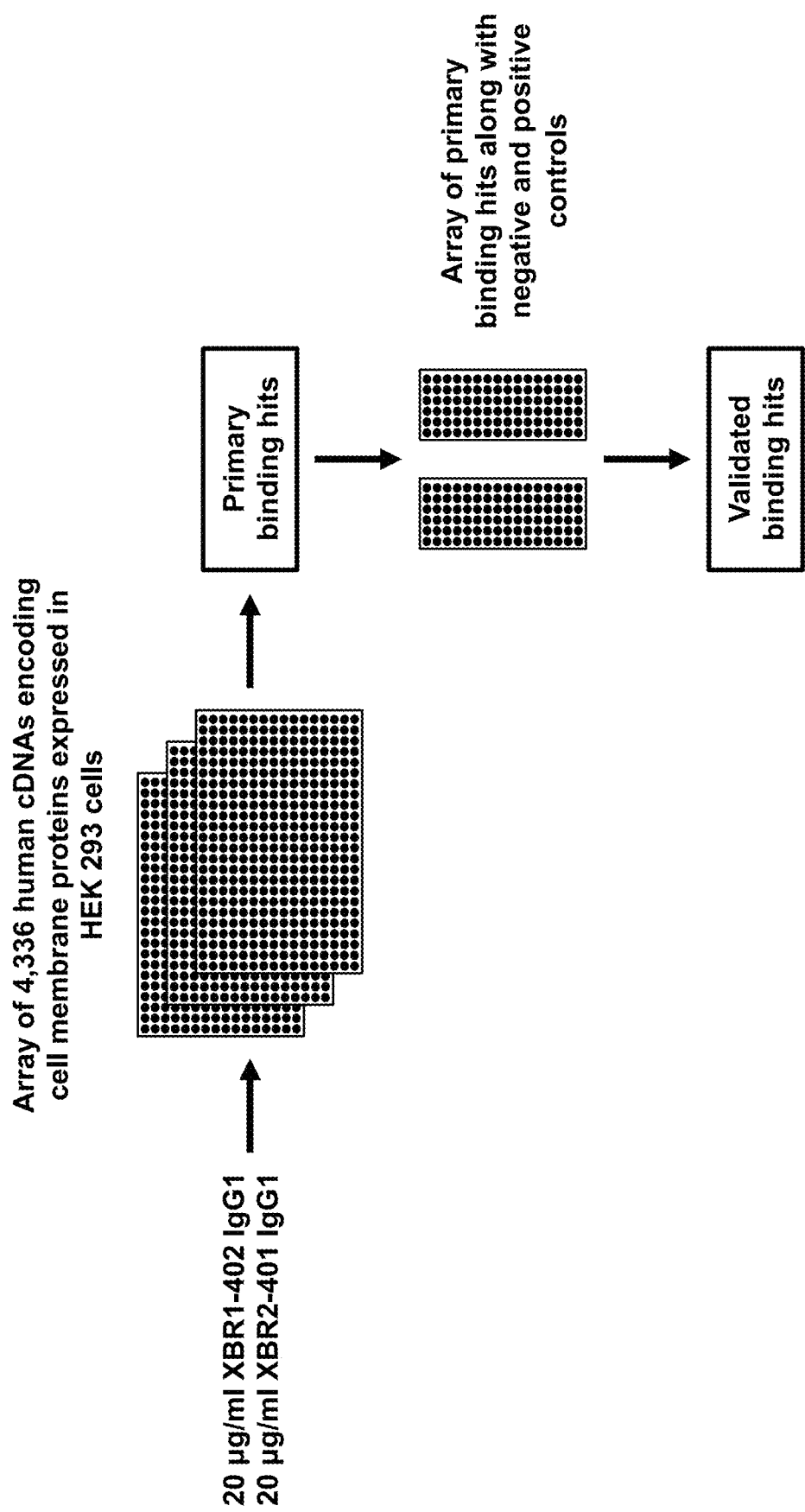
FIG. 17 provides an overview of the method for specificity analysis of chimeric rabbit/human anti-human ROR2 IgG1 XBR2-401 and, as a control, chimeric rabbit/human anti-human ROR1 IgG1 XBR1-402, with the Retrogenix Cell Microarray Platform.

To further investigate the therapeutic utility of ROR2-targeting mAbs, CAR-T cells based on XBR2-401 were engineered using previously described methods (Hudecek, M, Lupo-Stanghellini, M T, Kosasih, P. L., Sommermeyer, D., Jensen, M C., Rader, C., and Riddell, S. R. (2013) *Receptor affinity and extracellular domain modifications affect tumor recognition by ROR1-specific chimeric antigen receptor T cells. Clin. Cancer Res.* 19, 3153-3164). In brief, ex vivo expanded healthy donor CD8+CD62L+ T cells were lentivirally transduced with an EF1a promoter-driven expression cassette containing XBR2-401 in scFv format, followed by a short or long spacer, the transmembrane domain of human CD28, the signaling domain of 4-1BB, the signaling domain of CD3ζ, and a T2A-separated transmembrane EGFR fragment with truncated ligand binding and tyrosine kinase domains. FACS isolation of EGFR+ transduced T cells, revealed robust anti-ROR2 recognition in >90% of CAR-T cells. The activity of the ROR2-targeting XBR2-401 CAR-T with short and long spacer was tested against breast cancer cell lines T47D (ROR2+ROR1−) and MDA-MB-231 (ROR2−ROR1+). Since XBR2-401 binds to a membrane-proximal epitope in the Kr domain of ROR2, the inventors hypothesized predicted that XBR2-401 CAR-T cells are more active with a long rather than a short spacer. This was confirmed with respect to proliferation, IFN-γ and IL-2 secretion, and cytotoxicity in the presence of ROR2+ROR1− target cells (FIG. 16).

In accordance with these studies, the present invention provides monoclonal antibodies and related antibody-based binding proteins and antibody fragments (antigen-binding fragments) thereof that specifically recognize hROR2. The invention also provides antibody drug conjugates (ADCs) and chimeric antigen receptors (CARs) derived from the hROR2 antibodies described herein. Further provided in the invention are methods of using these antibody agents and related compositions in therapeutic and diagnostic applications for diseases and conditions with associated abnormal or elevated ROR2 expression, e.g., cancer.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press (4th ed., 2000). In addition, the following definitions are provided to assist the reader in the practice of the invention.

The term "antibody" also synonymously called "immunoglobulins" (Ig), or "antigen-binding fragment" refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate species. They can be generated using any suitable technology, e.g., hybridoma technology, ribosome display, phage display, gene shuffling libraries, semi-synthetic or fully synthetic libraries or combinations thereof. Unless otherwise noted, the term "antibody" as used in the present invention includes intact antibodies, antigen-binding polypeptide fragments and other designer antibodies that are described below or well known in the art (see, e.g., Serafini, J Nucl. Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region of most IgG isotypes (subclasses) is comprised of three domains, $C_{H1}$, $C_{H2}$ and $C_{H3}$, some IgG isotypes, like IgM or IgE comprise a fourth constant region domain, $C_{H4}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., *Sequences of Proteins of Immunological Interest*, U.S. Department of Health and Human Services, U.S. Government Printing Office (1987 and 1991).

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) $F_c$-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments (antigen-binding fragments).

"Binding affinity" is generally expressed in terms of equilibrium association or dissociation constants ($K_A$ or $K_D$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same. The binding affinity of an antibody is usually be expressed as the $K_D$ of a monovalent fragment (e.g. a $F_{ab}$ fragment) of the antibody, with $K_D$ values in the single-digit nanomolar range or below (subnanomolar or picomolar) being considered as very high and of therapeutic and diagnostic relevance.

As used herein, the term "binding specificity" refers to the selective affinity of one molecule for another such as the binding of antibodies to antigens (or an epitope or antigenic determinant thereof), receptors to ligands, and enzymes to substrates. Thus, all monoclonal antibodies that bind to a particular antigenic determinant of an entity (e.g., a specific epitope of ROR1 or ROR2) are deemed to have the same binding specificity for that entity.

The term "Antibody Drug Conjugate", or "ADC" refers to an antibody to which a therapeutically active substance or an active pharmaceutical ingredient (API) has been covalently coupled, such that the therapeutically active substance or an active pharmaceutical ingredient (API) can be targeted to the binding target of the antibody to exhibit its pharmacologic function. The therapeutically active substance or an active pharmaceutical ingredient can be a cellular toxin that is able to effect killing of the cells targeted by the ADCs, preferably malignant or cancer cells. The covalent attachment of a therapeutically active substance, an active pharmaceutical ingredient or a cellular toxin can be performed in a non-site specific manner using standard chemical linkers that couple payloads to lysine or cysteine residues, or, preferably the conjugation is performed in a site-specific manner, that allows full control of conjugation site and drug to antibody ratio (DAR) of the ADC to be generated.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "contacting" has its normal meaning and refers to combining two or more agents (e.g., polypeptides or phage), combining agents and cells, or combining two populations of different cells. Contacting can occur in vitro, e.g., mixing an antibody and a cell or mixing a population of antibodies with a population of cells in a test tube or growth medium. Contacting can also occur in a cell or in situ, e.g., contacting two polypeptides in a cell by coexpression in the cell of recombinant polynucleotides encoding the two polypeptides, or in a cell lysate. Contacting can also occur in vivo inside a subject, e.g., by administering an agent to a subject for delivery the agent to a target cell.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, WI); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

The term "subject" refers to human and non-human animals (especially non-human mammals). The term "subject" is used herein, for example, in connection with therapeutic and diagnostic methods, to refer to human or animal subjects. Animal subjects include, but are not limited to, animal models, such as, mammalian models of conditions or disorders associated with elevated ROR2 expression such as neuroblastoma, osteosarcoma, renal cell carcinoma, breast cancer, gastric cancer, prostate cancer, melanoma, squamous cell carcinoma, multiple myeloma and other cancers. Other specific examples of non-human subjects include, e.g., cows, horses, sheep, pigs, cats, dogs, mice, rats, rabbits, guinea pigs, monkeys.

Artificial T cell receptors (also known as chimeric T cell receptors, chimeric immunoreceptors, chimeric antigen receptors (CARs) or T-bodies) are engineered receptors, which graft an arbitrary specificity onto an immune effector cell. Typically, these receptors are used to graft the specificity of a monoclonal antibody onto a T cell; with transfer of their coding sequence facilitated by retroviral or lentiviral vectors or by transposons. CAR-engineered T cells (also abbreviated CAR-T cells) are genetically engineered T cells armed with chimeric receptors whose extracellular recognition unit is comprised of an antibody-derived recognition domain and whose intracellular region is derived from lymphocyte stimulating moiety(ies). The structure of the prototypic CAR is modular, designed to accommodate various functional domains and thereby to enable choice of specificity and controlled activation of T cells. The preferred antibody-derived recognition unit is a single chain variable fragment (scFv) that combines the specificity and binding residues of both the heavy and light chain variable regions of a monoclonal antibody. The most common lymphocyte activation moieties include a T-cell costimulatory (e.g. CD28) domain in tandem with a T-cell triggering (e.g. CD3zeta) moiety. By arming effector lymphocytes (such as T cells and natural killer cells) with such chimeric receptors, the engineered cell is redirected with a predefined specificity to any desired target antigen, in a non-HLA restricted manner. CAR constructs are introduced ex vivo into T cells from peripheral lymphocytes of a given patient using retroviral or lentiviral vectors or transposons. Following infusion of the resulting CAR-engineered T cells back into the patient, they traffic, reach their target site, and upon interaction with their target cell or tissue, they undergo activation and perform their predefined effector function. Therapeutic targets for the CAR approach include cancer and HIV-infected cells, or autoimmune effector cells.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

III. Antibodies, Antibody-Based Binding Proteins, Antibody Fragments Thereof, Antibody Drug Conjugates (ADCs), or CARs Specifically Binding to ROR2 and Related Derivative Compounds In one aspect, the invention provides novel antibodies, antibody-based binding proteins, antibody fragments (also termed "antigen-binding fragments") thereof, ADCs or CARs that specifically bind to human ROR2 with the same binding specificity as that of anti-ROR2 antibody exemplified herein (FIG. 1). Antibodies of the invention include intact antibodies (e.g., IgG1 antibodies exemplified herein), antibody fragments (e.g., Fab antibodies exemplified herein), antibody-based binding proteins, antibody fragments thereof, ADCs or CARs which contain the antigen-binding portions of an intact antibody that retain capacity to bind the cognate antigen, ROR2. Examples of such antibody fragments include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ or $V_L$ domain (see, e.g., Ward et al., Nature 341:544-546, 1989); and (vii) an isolated complementarity determining region (CDR) as a linear or cyclic peptide. Examples of antibody-based binding proteins are polypeptides in which the binding domains of the antibodies are combined with other polypeptides or polypeptide domains, e.g. alternative molecular scaffolds, Fc-regions, other functional or binding domains of other polypeptides or antibodies resulting in molecules with addition binding properties, e.g. bi- or multispecific proteins or antibodies. Such polypeptides can create an arrangement of binding or functional domains normally not found in naturally occurring antibodies or antibody fragments.

Antibodies of the invention also encompass antibody fragments, like single chain antibodies. The term "single chain antibody" refers to a polypeptide comprising a $V_H$ domain and a $V_L$ domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules.

Antibodies of the present invention also encompass single domain antigen-binding units, which have a camelid scaffold. Animals in the camelid family include camels, llamas, and alpacas. Camelids produce functional antibodies devoid of light chains. The heavy chain variable ($V_H$) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies.

The various antibodies, antibody-based binding proteins, and antibody fragments thereof described herein can be produced by enzymatic or chemical modification of the intact antibodies, or synthesized de novo using recombinant DNA methodologies, or identified using phage display libraries. Methods for generating these antibodies, antibody-based binding proteins, and antibody fragments thereof are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242:423-426, 1988; and Huston et al., Proc. Natl. Acad. Sci. USA 85:5879-5883, 1988. Fv antibody fragments can be generated as described in Skerra and Plückthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nat. Struct. Biol. 11:500-515, 2002; Ghahroudi et al., FEBS Letters 414:521-526, 1997; and Bond et al., J. Mol. Biol. 332:643-55, 2003. Other types of antigen-binding fragments (e.g., Fab, F(ab')2 or Fd fragments) can also be readily produced with routinely practiced immunology methods. See, e.g., Harlow & Lane, *Using Antibodies, A Laboratory Manual*, Cold Spring Harbor Laboratory Press, Cold Spring Harbor, New York, 1998.

In some embodiments, the antibodies, antibody fragments, antibody-based binding proteins, ADCs or CARs of the invention have their heavy chain CDR1, CDR2 and CDR3 sequences and their light chain CDR1, CDR2 and CDR3 sequences that are substantially identical to that of the antibodies shown in FIG. 1. The light chain and heavy chain CDR sequences of the exemplified antibodies are all indicated in the figure. In some of these embodiments, the antibodies, antibody fragments, antibody-based binding proteins, ADCs or CARs have (1) heavy chain CDR1-3 sequences that are substantially identical to SEQ ID NOs: 25-27, respectively; and light chain CDR1-3 sequences that are substantially identical to SEQ ID NOs:61-63, respectively; (2) heavy chain CDR1-3 sequences that are substantially identical to SEQ ID NOs:28-30, respectively; and light chain CDR1-3 sequences that are substantially identical to SEQ ID NOs:64-66, respectively; (3) heavy chain CDR1-3 sequences that are substantially identical to SEQ ID NOs: 31-33, respectively; and light chain CDR1-3 sequences that are substantially identical to SEQ ID NOs:67-69, respectively; (4) heavy chain CDR1-3 sequences that are substantially identical to SEQ ID NOs:34-36, respectively; and light chain CDR1-3 sequences that are substantially identical to SEQ ID NOs:70-72, respectively; (5) heavy chain CDR1-3 sequences that are substantially identical to SEQ ID NOs: 37-39, respectively; and light chain CDR1-3 sequences that are substantially identical to SEQ ID NOs:73-75, respectively; (6) heavy chain CDR1-3 sequences that are substantially identical to SEQ ID NOs:40-42, respectively; and light chain CDR1-3 sequences that are substantially identical to SEQ ID NOs:76-78, respectively; (7) heavy chain CDR1-3 sequences that are substantially identical to SEQ ID NOs: 43-45, respectively; and light chain CDR1-3 sequences that are substantially identical to SEQ ID NOs:79-81, respectively; (8) heavy chain CDR1-3 sequences that are substantially identical to SEQ ID NOs:46-48, respectively; and light chain CDR1-3 sequences that are substantially identical to SEQ ID NOs:82-84, respectively; (9) heavy chain CDR1-3 sequences that are substantially identical to SEQ ID NOs: 49-51, respectively; and light chain CDR1-3 sequences that are substantially identical to SEQ ID NOs:85-87, respectively; (10) heavy chain CDR1-3 sequences that are substantially identical to SEQ ID NOs:52-54, respectively; and light chain CDR1-3 sequences that are substantially identical to SEQ ID NOs:88-90, respectively; (11) heavy chain CDR1-3 sequences that are substantially identical to SEQ ID NOs:55-57, respectively; and light chain CDR1-3 sequences that are substantially identical to SEQ ID NOs:91-93, respectively; or (12) heavy chain CDR1-3 sequences that are substantially identical to SEQ ID NOs:58-60, respectively; and light chain CDR1-3 sequences that are substantially identical to SEQ ID NOs:94-96, respectively.

In some embodiments, the antibodies, antibody fragments, antibody-based binding proteins, ADCs or CARs of the invention comprise the heavy chain CDR1-CDR3 and light chain CDR1-CDR3 sequences that are respectively identical to the sequences shown in (1) SEQ ID NOs:25-27 and SEQ ID NOs:61-63 (antibody XBR2-401), (2) SEQ ID NOs:28-30 and SEQ ID NOs:64-66 (antibody XBR2-416), (3) SEQ ID NOs:31-33 and SEQ ID NOs:67-69 (antibody XBR2-433), (4) SEQ ID NOs:34-36 and SEQ ID NOs:70-72 (antibody XBR2-327), (5) SEQ ID NOs:37-39 and SEQ ID NOs:73-75 (antibody XBR2-TOP9), (6) SEQ ID NOs:40-42 and SEQ ID NOs:76-78 (antibody XBR2-TOP72), (7) SEQ ID NOs:43-45 and SEQ ID NOs:79-81 (antibody ERR2-302), (8) SEQ ID NOs:46-48 and SEQ ID NOs:82-84 (antibody ERR2-308), (9) SEQ ID NOs:49-51 and SEQ ID NOs:85-87 (antibody ERR2-316), (10) SEQ ID NOs:52-54 and SEQ ID NOs:88-90 (antibody ERR2-317), (11) SEQ ID NOs:55-57 and SEQ ID NOs:91-93 (antibody ERR2-TOP2), or (12) SEQ ID NOs:58-60 and SEQ ID NOs:94-96 (antibody ERR2-TOP35).

In other embodiments, the antibodies, antibody fragments, antibody-based binding proteins, ADCs or CARs of the invention that specifically bind to human ROR2 contain (a) a light chain variable domain having a sequence that is substantially identical to any one of SEQ ID NOs:13-24, (b) a heavy chain variable domain having a sequence that is substantially identical to any one of SEQ ID NOs:1-12, or (c) both a light chain of (a) and a heavy chain of (b). In some embodiments, the antibody, antibody fragment, antibody-based binding protein, ADC or CAR of the invention comprises both a light chain of (a) and a heavy chain of (b). In some embodiments, the antibody, antibody fragment, antibody-based binding protein, ADC or CAR of the invention contains (a) a light chain variable domain having at least 90% identity to any one of SEQ ID NOs:13-24, (b) a heavy chain variable domain having at least 90% sequence identity to any one of SEQ ID NOs:1-12, or (c) both a light chain of (a) and a heavy chain of (b). In some embodiments, the percentage identity can be at least 91%, at least 92%, at least 93%, at least 94%, at least 95%, at least 96%, at least 97%, at least 98%, or at least 99%, or even 100%. In some embodiments, the light chain variable domain has at least 95% identity to any one of SEQ ID NOs:13-24. In some embodiments, the light chain variable domain has 100% identity to any one of SEQ ID NOs:13-24. In some embodiments, the antibody, antibody fragment, antibody-based binding protein, ADC or CAR of the invention contains a heavy chain variable domain having at least 90% identity to any one of SEQ ID NOs:1-12. In other embodiments, the percentage identity can be at least 91%, at least 92%, at least 93%, at least 94%, at least 95%, at least 96%, at least 97%, at least 98%, or at least 99%, or even 100%. In some embodiments, the heavy chain variable domain has at least 95% identity to any one of SEQ ID NOs:1-12. In some embodiments, the heavy chain variable domain has 100% identity to any one of SEQ ID NOs:1-12.

In some embodiments, the antibody, antibody fragment, antibody-based binding protein, ADC or CAR of the invention of the invention can comprise any heavy chain as described herein (e.g., heavy chains shown in FIG. 1) in combination with any suitable light chain, such as those exemplified herein. Likewise, the antibody can comprise any of the light chains as described above (e.g., light chains shown in FIG. 1) in combination with any suitable heavy chain, such as those exemplified herein. For example, in preferred embodiments, the antibody, antibody fragment, antibody-based binding protein, ADC or CAR of the invention comprises a light chain having at least 90% identity to SEQ ID NO:13 and a heavy chain having at least 90% identity to SEQ ID NO:1, or a light chain having at least 90% identity to SEQ ID NO:14 and a heavy chain having at least 90% identity to SEQ ID NO:2, or a light chain having at least 90% identity to SEQ ID NO:15 and a heavy chain having at least 90% identity to SEQ ID NO:3. In some embodiments, the antibody, antibody fragment, antibody-based binding protein, ADC or CAR of the invention can comprise the light chain and heavy chain sequences respectively shown in (1) SEQ ID NO:13 and SEQ ID NO:1, (2) SEQ ID NO:14 and SEQ ID NO:2, or (3) SEQ ID NO:15 and SEQ ID NO:3. In the various embodiments, percent (%) identity of peptide sequences can be calculated, for example, as 100×[(identical positions)/min(TGA, TGB)], where TGA and TGB are the sum of the number of residues and internal gap positions in peptide sequences A and B in the alignment that minimizes TGA and TGB. See, e.g., Russell et al, J. Mol. Biol., 244: 332-350 (1994).

The antibody, antibody fragment, antibody-based binding protein, ADC or CAR of the invention of the invention can be any antibody including a full length antibody or an antibody fragment that specifically recognizes or binds to the extracellular domain of human ROR2. For example, the antibody, antibody fragment or antibody-based binding protein can be polyclonal, monoclonal, recombinant, chimeric, or humanized. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment or antibody-based binding protein having specificity for the extracellular domain of human ROR2, such as F(ab)2, Fv, scFv, IgGACH2, F(ab')2, scFv2CH3, Fab, VL, VH, scFv4, scFv3, scFv2, dsFv, Fv, scFv-Fc, (scFv)2, a diabody, and a bivalent antibody. The antibody can be any modified or synthetic antibody, including, but not limited to, non-depleting IgG antibodies, CARs, or other Fc or Fab variants of antibodies.

In addition to a heavy chain as described above, the antibody, antibody-based binding proteins or antibody fragments thereof of the invention can further comprise a light chain selected from a Fab library using sequential naive chain shuffling. Likewise, in addition to a light chain as described above, the antibody of the invention can further comprise a heavy chain selected from a Fab library using sequential naive chain shuffling.

In some embodiments, the invention provides antibodies, antibody-based binding proteins or antibody fragments thereof that are conservatively modified variants of the anti-ROR2 antibodies exemplified herein. Typically, the variable regions of these variants have an amino acid sequence that is identical to one of these exemplified sequences except for conservative substitutions at one or more amino acid residues. In some embodiments, the antibody, antibody fragment, antibody-based binding protein, ADC or CAR of the invention specifically binds to human ROR2 and contains at least one CDR having a sequence selected from the group consisting of SEQ ID NOs:25-96. The invention also provides an isolated antibody, antibody fragment, antibody-based binding protein, ADC or CAR with specificity for ROR2 containing one or more variants of the foregoing CDR sequences or substantially identically CDR sequences. The variant CDR sequences in these antibodies can include 1, 2, or 3 substitutions, insertions, deletions, or combinations thereof in a sequence selected from the group consisting of SEQ ID NOs:25-96. For example, a recombinant chimeric or humanized antibody (or fragment thereof) can include one, two, three, four, five, or six of the foregoing CDR sequences. In some embodiments, however, the recombinant chimeric or humanized antibody (or fragment thereof) includes three CDR sequences of the same light or heavy chain, e.g., light chain CDRS shown in SEQ ID NOs:61-63, SEQ ID NOs:64-66, or SEQ ID NOs: 67-69; and heavy chain CDRs shown in SEQ ID NOs:25-27, SEQ ID NOs:28-30; or SEQ ID NOs:31-33. In some embodiments, the recombinant chimeric or humanized antibody (or fragment thereof) includes six CDR sequences of the same antibody, e.g., (a) SEQ ID NOs:61-63 and SEQ ID NOs:25-27; (b) SEQ ID NOs:64-66 and SEQ ID NOs:28-30; or (c) SEQ ID NOs:67-69 and SEQ ID NOs:31-33.

In some embodiments, the invention provides antibodies, antibody-based binding proteins or antibody fragments thereof with avidity for ROR2 of about 10 µM or less, 5 µM or less, 2 µM or less, 1 µM or less, 500 nM or less, 400 nM or less, 300 nM or less, or 200 nM or less. In some embodiments, the antibodies, antibody-based binding proteins or antibody fragments thereof bind to ROR2 with an avidity of about 100 nM or less, about 75 nM or less, about 50 nM or less, about 25 nM or less, about 10 nM or less, or about 5 nM or less. In some embodiments, the antibodies, antibody-based binding proteins or antibody fragments thereof bind to ROR2 with an avidity of about 1 nM or less, about 800 pM or less, about 700 pM or less, about 600 pM or less, about 500 pM or less, about 400 pM or less, about 300 pM or less, about 200 pM or less, or about 100 pM or less. Avidity can be measured using art-known techniques, such as ELISA, biolayer inferometry, or surface plasmon resonance.

The antibody, antibody-based binding protein or antibody fragment thereof of the invention can be produced by any suitable technique, for example, using any suitable eukaryotic or non-eukaryotic expression system. In certain embodiments, the antibody, antibody-based binding protein or antibody fragment thereof is produced using a mammalian expression system. Some specific techniques for generating the antibodies or antigen-binding fragments of the invention are exemplified herein. In some embodiments, the antibodies or antigen-binding fragments of the invention can be produced using a suitable non-eukaryotic expression system such as a bacterial expression system. Bacterial expression systems can be used to produce fragments such as a F(ab)2, Fv, scFv, IgGACH2, F(ab')2, scFv2CH3, Fab, VL, VH, scFv4, scFv3, scFv2, dsFv, Fv, scFv-Fc, (scFv)2, and diabodies. Techniques for altering DNA coding sequences to produce such fragments are known in the art.

The antibodies, antibody-based binding proteins or antibody fragments thereof of the invention can be conjugated to a synthetic molecule using any type of suitable conjugation. Recombinant engineering and incorporated selenocysteine (e.g., as described in U.S. Pat. No. 8,916,159 issued on Dec. 23, 2014) can be used to conjugate a synthetic molecule. Other methods of conjugation can include covalent coupling to native or engineered lysine side-chain amines or cysteine side-chain thiols. See, e.g., Wu et al., Nat. Biotechnol, 23: 1 137-1 146 (2005).

In a preferred embodiment, the antibodies, antibody-based binding proteins or antibody fragments thereof of the invention conjugated to a synthetic molecule (called "ADC" for antibody drug conjugate with the synthetic molecule being a toxin) are obtained by means of site-specific sortase-enzyme mediated antibody conjugation. As disclosed in WO2014140317, sortases (also called sortase transpeptidases) form a group of prokaryotic enzymes that modify surface proteins by recognizing and cleaving a specific peptide motif called "sortase recognition tag" or "sortase tag". Usually, a given sortase enzyme recognizes one or more sortase recognition tags. Sortase enzymes can be naturally occurring, or may have undergone genetic engineering (Dorr et al., PNAS 2014; 111, 13343-8).

In a preferred embodiment, the conjugate is obtained by means of site-specific sortase-enzyme mediated conjugation of (a) an antibody, antibody-based binding protein or antibody fragment thereof as described herein carrying one or more sortase recognition tags, and (b) one or more synthetic molecules carrying a glycine or oligoglycine tag, Gly(n). Preferably, the sortase recognition tag is fused or conjugated to the C-terminus of at least one subdomain of the antibody. Said sortase recognition tag is preferably selected from the group consisting of LPXSG (SEQ ID NO:137), LPXAG (SEQ ID NO:138), LPXTG (SEQ ID NO:139), LAXTG (SEQ ID NO:140), 3 and NPQTG (SEQ ID NO:141), with X being any amino acid residue. Preferably, the oligoglycine tag, Gly(n), has a length of 1 to 21 glycine residues, preferably with a length of 3 to 5 amino acids, i.e., $Gly_{(3)}$, $Gly_{(4)}$, or $Gly_{(5)}$.

The synthetic molecule can be any molecule such as one targeting a tumor. In some embodiments, the synthetic molecule for conjugation to the antibody is a protein (e.g., an antibody) or an RNA or DNA aptamer. In one embodiment, the antibodies, antibody-based binding proteins or antibody fragments thereof of the invention conjugated to a synthetic molecule have the general formula $A-(L-P)_n$, in which: A is an antibody, antibody-based binding protein or antibody fragment thereof as described herein, L is one or more linkers, P is one or more payloads selected from the group consisting of a label and a cytotoxic or cytostatic agent, and in which n is an integer between $\geq 1$ and $\leq 10$. In this embodiment, the linker preferably comprises, or consists of, at least one selected from the group consisting of: an oligopeptide linker (including cleavable and non-cleavable oligopeptide linkers), a hydrazine linker, a thiourea linker, a self-immolative linker, a succinimidyl trans-4-(maleimidylmethyl)cyclohexane-1-carboxylate (SMCC) linker, a maleimide linker, a disulfide linker, a thioether linker, and/or a maleimide linker.

The skilled person understands that further linkers may be suitable. Such linkers may be non-cleavable or may be cleaved by changes in pH, redox potential or specific intracellular enzymes. Cleavable oligopeptide linkers include protease- or matrix metalloprotease-cleavable linkers. It is understood that the linker may comprise combinations of the above. For example, the linker may be a valine-citruline PAB linker. In a preferred embodiment, the linker comprises an oligopeptide with a sequence comprising the pentapeptide motif LPXSG (SEQ ID NO:137), LPXAG (SEQ ID NO:138), LPXTG (SEQ ID NO:139), LAXTG (SEQ ID NO:140), or NPQTG (SEQ ID NO:141) with X being any amino acid, followed by an oligo-glycine stretch, $Gly_{(n)}$, with n being an integer between $\geq 1$ and $\leq 21$. In a preferred embodiment, the linker is conjugated to the C-terminus of at least one subdomain of the antibody, antibody-based binding proteins or antibody fragments thereof.

In various embodiments, suitable synthetic molecules ("payloads") for conjugation to the antibody include, e.g., therapeutic agents such as cytotoxic, cytostatic, or antiangiogenic agents, radioisotopes, and liposomes. A cytotoxic agent can be a plant, fungal, or bacterial molecule. In some embodiments, the cytotoxic agent for conjugation to the antibody of the invention is a small molecular weight toxin (MW<2'000 Dalton, preferably MW<1'000 Dalton), a peptide toxin, or a protein toxin. Many specific examples of these toxins are well known in the art. See, e.g., Dyba et al., Curr. Pharm. Des. 10:2311-34, 2004; Kuyucak et al., Future Med. Chem. 6:1645-58, 2014; Beraud et al., Inflamm. Allergy Drug Targets. 10:322-42, 2011; and Middlebrook et al., Microbiol. Rev. 48:199-221, 1984. In some embodiments, a therapeutic agent is conjugated to the antibody. For example, the therapeutic agent can be a maytansinoid (e.g., maytansinol or DM1 maytansinoid), a taxane, a calicheamicin, a cemadotin, a monomethyllauristatin (e.g., monomethylauristatin E or monomethylauristatin F), a pyrrolobenzodiazepine (PBD), preferably an anthracycline, more preferably a derivative of the highly potent anthracycline PNU-159682. Particularly preferred derivatives of the highly potent anthracycline PNU-159682 are disclosed in WO2016102679 (which is incorporated by reference herein). Therapeutic agents also include vincristine and prednisone. In various embodiments, the therapeutic agent that may be employed in the invention can be an antimetabolite (e.g., an antifolate such as methotrexate, a fluoropyrimidine such as 5-fluorouracil, cytosine arabinoside, or an analogue of purine or adenosine); an intercalating agent an intercalating agent (for example, an anthracycline such as doxorubicin, nemorubicine, or preferably a derivative of PNU-159682), daunomycin, epirabicin, idarubicin, mitomycin-C, dactinomycin, or mithramycin, or other intercalating agents such as pyrrolobenzodiazepine); a DNA-reactive agent such as calicheamicins, tiancimycins, and other enediynes; a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an RNA polymerase inhibitor such as α-amanitin; an antimitotic agent (e.g., a vinca alkaloid such as vincristine, or a taxoid such as paclitaxel or docetaxel); a topoisomerase inhibitor (for example, etoposide, teniposide, amsacrine, topotecan); a cell cycle inhibitor (for example, a flavopyridol); or a microbtubule agent (e.g., an epothilone, a tubulysine, a pre-tubulysine, a discodermolide analog, or an eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include iodine ($^{131}$I), yttrium ($^{90}$Y), lutetium ($^{177}$Lu), actinium ($^{225}$Ac), praseodymium, astatine (At), rhenium (Re), bismuth (Bi or Bi), and rhodium (Rh). Antiangiogenic agents include linomide, bevacuzimab, angiostatin, and razoxane.

In a preferred embodiment, the synthetic toxin molecule is selected from PNU-159682 as described in Quintieri et al. (2005) and derivatives thereof (see formula (i) below), maytansine, monomethyl auristatin MMAE, and monomethyl auristatin MMAF. In a preferred embodiment, the toxin, joined to the linker at its wavy line, is of formula (i), as described in WO 2016102679 (which is incorporated by reference herein):

formula (i)

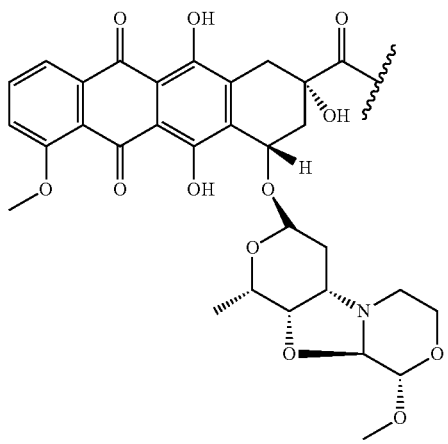

Figure 13:
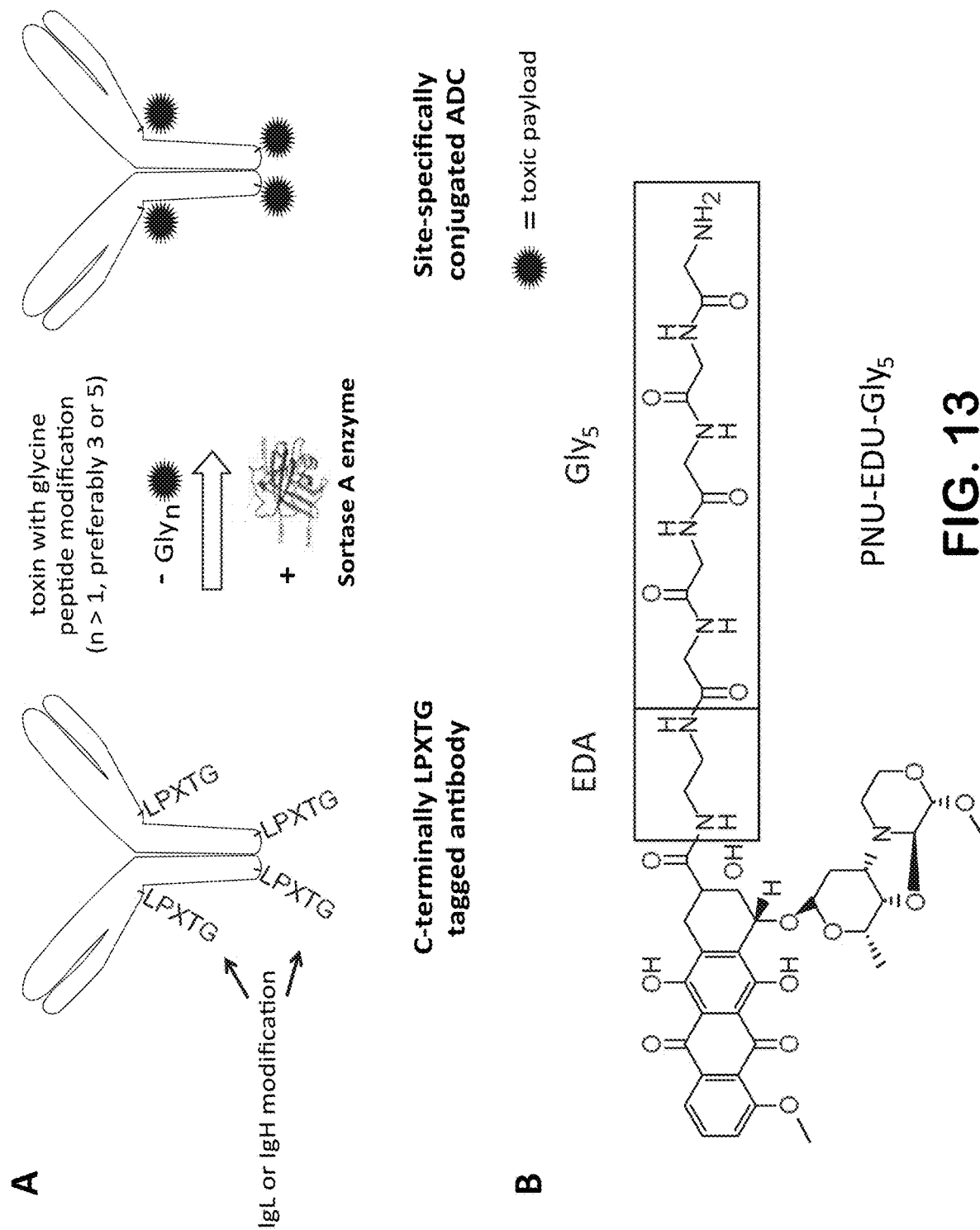
FIG. 13 shows schematically how site-specifically conjugated ADCs disclosed in this invention have been generated. (A) shows schematically the mechanism of sortase-enzyme mediated antibody conjugation (SMAC-technology) as disclosed in WO2014140317. In order to generate site-specifically conjugated ADCs, recombinant antibodies were expressed with the C-terminal pentapeptide motif LPXTG (SEQ ID NO:139), which serve as recognition sites for the sortase enzyme A from *Staphylococcus aureus* (SrtA). When a glycine modified toxin substrate is incubated with pentapeptide motif LPXTG containing antibody and sortase A enzyme, the sortase A enzyme catalyzes a transpeptidation reaction by which the glycine-modified toxin replaces the C-terminal glycine of the LPXTG motif and is covalently coupled to the threonine of the remaining LPXT (SEQ ID NO:142) sequence. This way site-specifically and C-terminally toxin-conjugated ADCs can be generated with high efficiency. (B) shows the structure of the preferred toxin, a PNU-159682 derivative comprising a glycine(5×)-ethylene-diamino (Gly$_{(5)}$-EDA) linker connecting a 5× glycine stretch to the carbonyl group at C13 of the anthracycline structure, as disclosed in WO2016102697.

In the embodiment where the synthetic molecule is of formula (i), it is preferred that the linker comprise an alkyldiamino group of the form $NH_2—(CH_2)_m—NH_2$, where m≥1 and ≤11, preferably m=2, such that one amino group is directly linked at the wavy line of formula (i) to form an amide bond. It is moreover preferred that the second amino group is linked to an oligopeptide linker, which is more preferably an oligoglycine, $Gly_{(n)}$, with n being ≥1 and ≤21. The most preferred payload is shown in FIG. 13 (B).

In some embodiments, the synthetic molecule can be conjugated to any antibody, antibody-based binding protein, or antibody-fragment. In some embodiments, the synthetic molecule can be a label. Labels can be useful in diagnostic applications and can include, for example, contrast agents. A contrast agent can be a radioisotope label such as iodine ($^{131}$I or $^{125}$I) indium ($^{111}$In), technetium ($^{99}$Tc), phosphorus ($^{32}$P), carbon ($^{14}$C), tritium ($^{3}$H), other radioisotope (e.g., a radioactive ion), or a therapeutic radioisotope such as one of the therapeutic radioisotopes listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

In some other embodiments, the synthetic molecule can be a liposome, as described in Bendas, BioDrugs, 15: 215-224, 2001. In such embodiments, the antibody can be conjugated to a colloidal particle, e.g., a liposome, and used for controlled delivery of an agent to diseased cells. In preparing an antibody conjugated to a liposome, e.g., an immunoliposome, an agent such as a chemotherapeutic or other drug can be entrapped in the liposome for delivery to a target cell. In some embodiments, the antibodies, antibody-based binding proteins or antibody fragments thereof of the invention can also have specificity for one or more antigens in addition to ROR2. For example, the antibody of the invention can be engineered (e.g., as a bivalent diabody or a conjugated Fab dimer or trimer) to have specificity for ROR2 and another tumor antigen, e.g., an antigen associated with neuroblastoma, renal cell carcinoma, breast cancer, gastric cancer, prostate cancer, colon cancer (e.g., colon adenocarcinoma), or breast cancer (e.g., breast adenocarcinoma). The antibody can be engineered to have specificity for ROR2 and an antigen that promotes activation or targeting of cytotoxic effector cells.

To further investigate the therapeutic utility of ROR2-targeting mAbs, chimeric antigen receptors (CARs) and CAR-T cells based on the mAbs were generated. Typically, the chimeric antigen receptor of the invention contains a hROR2 antibody or antibody fragment described herein that is fused to a transmembrane region and an intracellular T-cell receptor (TCR) signaling domain. CAR-T cells based on XBR2-401 were engineered using previously described methods (Hudecek, M, Lupo-Stanghellini, M T, Kosasih, P. L., Sommermeyer, D., Jensen, M. C., Rader, C., and Riddell, S. R. (2013) *Receptor affinity and extracellular domain modifications affect tumor recognition by ROR1-specific chimeric antigen receptor T cells. Clin. Cancer Res.* 19, 3153-3164). In brief, ex vivo expanded healthy donor CD8+ CD62L+ T cells were lentivirally transduced with an EF1α promoter-driven expression cassette containing XBR2-401 in scFv format, followed by a short or long spacer, the transmembrane domain of human CD28, the signaling domain of 4-1BB, the signaling domain of CD3, and a T2A-separated transmembrane EGFR fragment with truncated ligand binding and tyrosine kinase domains. FACS isolation of EGFR+ transduced T cells, revealed robust anti-ROR2 recognition in >90% of CAR-T cells. The activity of the ROR2-targeting XBR2-401 CAR-T with short and long spacer against breast cancer cell lines T47D (ROR2+ ROR1−) and MDA-MB-231 (ROR2−ROR1+). Since XBR2-401 binds to a membrane-proximal epitope in the Kr domain of ROR2, it is likely that XBR2-401 CAR-T cells are more active with a long rather than a short spacer. This was confirmed with respect to proliferation, IFN-γ and IL-2 secretion, and cytotoxicity in the presence of ROR2+ ROR1− target cells (FIG. 16).

IV. Polynucleotides, Vectors and Host Cells for Producing ROR2 Antibodies

The invention provides substantially purified polynucleotides (DNA or RNA) that are identical or complementary to sequences encoding polypeptides comprising segments or domains of the antibody, antibody-based binding protein or antibody fragment thereof chains described herein. In some embodiments, the polynucleotides of the invention encode the heavy chain or light chain domains sequences shown in FIG. 1. As exemplifications, a pair of polynucleotides encoding the heavy chain variable domain and light chain variable domain sequences of antibodies XBR2-401, XBR2-416 and XBR2-433 are shown in SEQ ID NOs:129 and 132, SEQ ID NOs:130 and 133, and SEQ ID NOs:131 and 134, respectively. Some of the polynucleotides of the invention comprise the nucleotide sequence as shown in SEQ ID NO:129, 130, or 131 and/or the light chain variable region sequence as shown in SEQ ID NO:132, 133, or 134. Some other polynucleotides of the invention comprise nucleotide sequences that are substantially identical (e.g., at least 65, 80%, 95%, or 99%) to a sequence selected from SEQ ID NOs:129-134. When expressed from appropriate expression vectors, polypeptides encoded by these polynucleotides are capable of exhibiting ROR2 antigen binding capacity.

Also provided in the invention are polynucleotides which encode at least one CDR region and usually all three CDR regions from the heavy or light chain of the antibodies described herein. Some other polynucleotides encode all or substantially all of the variable region sequence of the heavy chain and/or the light chain of the exemplified antibodies. For example, some of these polynucleotides encode the amino acid sequence of the heavy chain variable region shown in any one SEQ ID NOs:1-12, and/or the amino acid sequence of the light chain variable region shown in any one SEQ ID NOs:13-24. Because of the degeneracy of the code, a variety of nucleic acid sequences will encode each of the immunoglobulin amino acid sequences.

The polynucleotides of the invention can encode only the variable region sequences of the exemplified antibodies. They can also encode both a variable region and a constant region of the antibody. Some of polynucleotide sequences of the invention nucleic acids encode a mature heavy chain variable region sequence that is substantially identical (e.g., at least 80%, 90%, 95% or 99%) to the mature heavy chain variable region sequence shown in any one SEQ ID NOs: 1-12. Some other polynucleotide sequences encode a mature light chain variable region sequence that is substantially identical to the mature light chain variable region sequence shown in any one SEQ ID NOs:13-24. Some of the polynucleotide sequences encode a polypeptide that comprises variable regions of both the heavy chain and the light chain of one of the exemplified antibodies. Some other polynucleotides encode two polypeptide segments that respectively are substantially identical to the variable regions of the heavy chain or the light chain of one of the exemplified antibodies.

The polynucleotide sequences can be produced by de novo solid-phase DNA synthesis or by PCR mutagenesis of an existing sequence (e.g., sequences as described in the Examples below) encoding an exemplified functional antibody. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., *PCR Technology: Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the invention are expression vectors and host cells for producing the functional antibodies described herein. Specific examples of plasmid and transposon based vectors for expressing the antibodies are described in the Examples below. Various other expression vectors can also be employed to express the polynucleotides encoding the functional antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). For example, nonviral vectors useful for expression of the antibody polynucleotides and polypeptides in mammalian (e.g., human) cells include pCEP4, pREP4, pThioHis A, B & C, pcDNA3.1/His, pEBVHis A, B & C (Invitrogen, San Diego, CA), MPSV vectors, and numerous other vectors known in the art for expressing other proteins. Other useful nonviral vectors comprise expression cassettes that can be mobilized with Sleeping Beauty, PiggyBack and other transposon systems. Useful viral vectors include vectors based on lentiviruses or other retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a functional antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a functional antibody chain or fragment. These elements typically include an ATG initiation codon and adjacent ribosome binding site (Kozak consensus sequence) or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted functional antibody sequences. More often, the inserted functional antibody sequences are linked to a signal sequences before inclusion in the vector. Vectors to be used to receive sequences encoding the functional antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human, and preferably of human IgG1 antibodies.

The host cells for harboring and expressing the functional antibody chains can be either prokaryotic or eukaryotic. In some preferred embodiments, mammalian host cells are used to express and to produce the antibody polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. In addition to the cell lines exemplified herein, a number of other suitable host cell lines capable of secreting intact immunoglobulins are also known in the art. These include, e.g., the CHO cell lines, various HEK 293 cell lines, various Cos cell lines, HeLa cells, myeloma cell lines, transformed B-cells and hybridomas. The use of mammalian tissue cell culture to express polypeptides is discussed generally in, e.g., Winnacker, *From Genes to Clones*, VCH Publishers, N.Y., N.Y., 1987. Expression vectors for mammalian host cells can include expression control sequences, such as an origin of replication, a promoter, and an enhancer, and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EF1α and human UbC promoters exemplified herein, the metallothionein promoter, the constitutive adenovirus major late promoter, the dexamethasone-inducible MMTV promoter, the SV40 promoter, the MRP pol III promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transformation is commonly utilized for prokaryotic cells, whereas calcium phosphate treatment or electroporation may be used for other cellular hosts (see generally Brent et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate for the cell type.

The invention further provides eukaryotic or non-eukaryotic cells (e.g., T lymphocytes) that have been recombinantly engineered to produce the antibodies, antibody-based binding proteins or antibody fragments thereof of the invention. The eukaryotic or non-eukaryotic cells can be used as an expression system to produce the antibody of the invention. In some embodiments, the invention provides ROR2 targeted immune cells that are engineered to recombinantly express an ROR2 specific antibody of the invention. For example, the invention provides a T cell engineered to express an antibody of the invention (e.g., an scFv, scFv-Fc, or (scFv)2), which is linked to a synthetic molecule containing one or more of the following domains: a spacer or hinge region (e.g., a CD28 sequence or a IgG4 hinge-Fc sequence), a transmembrane region (e.g., a transmembrane canonical domain), and an intracellular T-cell receptor (TCR) signaling domain, thereby forming a chimeric antigen receptor (CAR) or T-body. Intracellular TCR signaling domains that can be included in a CAR (or T-body) include, but are not limited to, CD3ζ, FcR-γ, and Syk-PT signaling domains as well as the CD28, 4-1BB, and CD134 co-signaling domains. Methods for constructing T-cells expressing a CAR (or T-body) are known in the art. See, e.g., Marcu-Malina et al., Expert Opinion on Biological Therapy, Vol. 9, No. 5 (posted online on Apr. 16, 2009).

V. Therapeutic and Diagnostic Applications

In one aspect, the invention provides methods for inhibiting cells that express ROR2 (ROR2 cells) by contacting the cells with an antibody, antibody-based binding protein or antibody fragment thereof of the invention, or an antibody drug conjugate (ADC) or an engineered cell harboring a chimeric antigen receptor (CAR) described herein. The antibody, antibody-based binding protein or antibody fragment thereof can be a naked (unconjugated) molecule or an antibody molecule conjugated to a synthetic molecule, e.g., a cytotoxic, cytostatic, or antiangiogenic agent, a radioisotope, or even to a liposome. The method can be used to inhibit ROR2 cells in vitro or in a subject (i.e., in vivo). The contacted ROR2 cells can be in, for example, a cell culture or animal model of a disorder associated with elevated levels of ROR2. The methods are useful, for example, to measure and/or rank (relative to another antibody) the antibody's inhibitory activity for a specific ROR2 cell type. Inhibiting ROR2 cells can include blocking or reducing the activity or growth of ROR2 cells. Inhibiting can also include the killing of ROR2 cells. While the methods are not bound by or limited to any particular mechanism of action, inhibitory activity can be mediated by blocking ROR2-mediated signaling or by blocking the signaling of an ROR2 associated receptor. Inhibitory activity can also be mediated by recruitment of immune system effectors that attack ROR2 cells, e.g., by activating constituents of the antibody-dependent cell-mediated cytotoxicity (ADCC) or complement systems.

In some related embodiments, the invention provides methods for treating a subject that has, is suspected to have, or is at risk of developing a disorder associated with elevated levels of ROR2. Generally, the methods include administering a pharmaceutical composition that contains a therapeutically effective amount of an isolated antibody, antibody-based binding protein, antibody fragment thereof, ADC or CAR of the invention to the subject. The antibody can be any anti-ROR2 antibody of the invention as described herein. Thus, the antibody can be chimeric, humanized, synthetic, F(ab)2, Fv, scFv, IgGACH2, F(ab')2, scFv2CH3, Fab, VL, VH, scFv4, scFv3, scFv2, dsFv, Fv, or (scFv)2. In some embodiments, the method includes administering an IgG, an scFv, a dsFv, a F(ab')2, a diabody, or a bivalent antibody. The administered antibody or antigen-binding fragment can be conjugated to a synthetic molecule described above, e.g., a cytotoxic, cytostatic, or antiangiogenic agent, a therapeutic radioisotope, or a liposome. An exemplary cytotoxic agent is Pseudomonas exotoxin A (PE38). Disorders that can be treated include neuroblastoma, osteosarcoma, renal cell carcinoma, breast cancer, gastric cancer, prostate cancer, melanoma, squamous cell carcinoma, multiple myeloma and other disorders with elevated ROR2 expression.

In some embodiments, the invention provides methods for treating a subject that has, is suspected to have, or is at risk of developing a disorder associated with expression of ROR2 by adoptive transfer of the genetically engineered T-cells described herein, which express an antibody or antigen-binding fragment of the invention as a chimeric antigen receptor (CAR) that selectively binds ROR2. Recombinant technology can be used to introduce CAR-encoding genetic material into any suitable T-cells, e.g., central memory T-cells from the subject to be treated. The T-cells carrying the genetic material can be expanded (e.g., in the presence of cytokines). The genetically engineered T-cells are transferred, typically by infusion, to the patient. The transferred T-cells of the invention can then mount an immune response against ROR2 expressing cells in the subject. The adoptive transfer method can be used, for example, to treat subjects that have or are suspected to have any of the cancers associated with ROR2, including neuroblastoma, osteosarcoma, renal cell carcinoma, breast cancer, gastric cancer, prostate cancer, melanoma, squamous cell carcinoma, multiple myeloma and other cancers.

In some embodiments, the foregoing methods of treatment can further include coadministering a second therapeutic agent for treating the disorder associated with elevated ROR2. For example, when the disorder to be treated involves an ROR2-expressing cancer, the method can further include co-administration of a cytotoxic, cystostatic, or antiangiogenic or immune-stimulatory agent (e.g. immune-checkpoint inhibitor antibodies, for instance, but not limited to, those binding to PD1, PDL1, CTLA4, OX40, TIM3, GITR, LAG3 and the like) suitable for treating the cancer. If the cancer is a B-cell malignancy, the method can further include, for example, co-administration of rituximab, alemtuzumab, ofatumumab, ocrelizumab, or a CHOP chemotherapeutic regimen.

In some other embodiments, the invention provides method for detecting in a biological sample an altered level of ROR2 (e.g., cell surface ROR2), for example, relative to a control, either by FACS, immunohistochemistry (IHC) or Western Blotting. Generally, the method includes contacting a biological sample with an antibody, antibody-based binding protein, antibody fragment thereof of the invention and determining the amount of antibody that selectively binds to material (e.g., cells) in the sample to thereby determine the level of ROR2 in the biological sample. A biological sample can be from a cell culture or from a test subject, e.g., a plasma or a tissue sample from a subject that has, is suspected to have, or is at risk of developing a disease or condition associated with elevated ROR2 in a subject. A control level desirably corresponds to the ROR2 level detected using the same antibody in a corresponding sample(s) from one or more control cultures or disease-free subjects. Methods of using the antibody of the invention to determine ROR2 levels can include any immunoassay such as immuno-(Western) blotting, enzyme-linked immunosorbent assay (ELISA), Immunohistochemistry (IHC) and flow cytometry, e.g., fluorescence-activated cell sorting (FACS) analysis.

The methods of detection can be used to screen for the presence of a disorder associated with elevated ROR2. The methods include obtaining a sample from a test subject in need of screening, e.g., a subject that has, is suspected to have, or is at risk of developing a disorder associated with elevated ROR2. The level of ROR2 (e.g., the amount or concentration) in the sample is measured using an antibody, antibody-based binding protein, antibody fragment thereof of the invention, and the level in the sample is compared to a control level of ROR2. The control level represents, for example, the mean level (e.g., the amount or concentration) in sample(s) from one or, preferably, multiple control group subjects that do not have a disorder associated with elevated ROR2. Alternatively, the control level can correspond to the level or mean level of ROR2 in one or more samples taken from the test subject at one or more prior times, such as when the test subject did not have or did not exhibit, a condition associated with elevated ROR2. A significantly higher level of ROR2 in the biological sample relative to the control level is indicative of a disorder associated with elevated ROR2 in the subject. In subjects such as humans, where cell surface ROR2 expression is largely restricted to embryonic development, a control level of ROR2 can be zero or none. Thus, in some embodiments of the method of the invention, any significant and detectable amount of ROR2 in a biological sample can be indicative of a disorder associated with elevated ROR2 in the subject.

Additionally, the methods of detection can be used to monitor the progress of a disorder associated with elevated ROR2. The method includes obtaining a sample from a subject in need of screening, e.g., a subject having been diagnosed or suspected to have a disorder associated with elevated ROR2. The level of ROR2 in the sample is measured using an antibody, antibody-based binding protein, antibody fragment thereof of the invention, and the level in the sample is compared to a control level corresponding to the level or mean level of ROR2 in one or more samples taken from the test subject at one or more prior times. Levels of ROR2 that are significantly elevated or decreased relative to control indicate that the subject's disorder is deteriorating or improving, respectively. The foregoing methods of detection can be used to screen for the presence or to monitor the progress of disorders including, for example, neuroblastoma, osteosarcoma, renal cell carcinoma, breast cancer, gastric cancer, prostate cancer, melanoma, squamous cell carcinoma, multiple myeloma and other cancers.

In some embodiments, the invention provides methods for screening a subject for an altered level of ROR2. Generally, the methods entail administering to the subject an antibody, antibody-based binding protein, antibody fragment thereof of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the methods include determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk of developing an ROR2-expressing tumor, such as neuroblastoma, osteosarcoma, renal cell carcinoma, breast cancer, gastric cancer, prostate cancer, melanoma, squamous cell carcinoma, multiple myeloma and other cancers, and the method is used to screen for or detect the presence of the tumor. In another embodiment, the method can be used to monitor the size or density of a ROR2-expressing tumor over time, e.g., during a course of treatment.

VI. Pharmaceutical Compositions and Combinations

In another aspect, the invention provides pharmaceutical compositions that contain an antibody, an antibody fragment, an antibody-based binding protein, or an ADC as described herein and a pharmaceutically acceptable carrier. Pharmaceutical compositions can be prepared from any of the antibodies or related compounds described herein. Exemplary compositions include one or more of a chimeric antibody having SEQ ID NO:13 (light chain) and/or SEQ ID NO:1 (heavy chain), a chimeric antibody having SEQ ID NO:14 (light chain) and/or SEQ ID NO:2 (heavy chain), and a chimeric antibody having SEQ ID NO:15 (light chain) and/or SEQ ID NO:3 (heavy chain). Other antibodies, antibody fragments, antibody-based binding proteins, or ADCs suitable for the pharmaceutical compositions of the invention include those having a light chain sequence as shown in SEQ ID NOs:16-24 and/or a heavy chain sequence as shown in SEQ ID NOs:4-12. Other exemplary compositions of the invention can contain a humanized antibody having one, two, three, four, five, or six CDRs selected from the group consisting of SEQ ID NOs:25-96. In some embodiments, however, the antibody includes three CDR sequences of the same exemplified light or heavy chains shown in FIG. 1. These include the heavy chain CDR1, CDR2 and CDR3 sequences and light chain CDR1, CDR2 and CDR3 sequences respectively shown in (i) SEQ ID NOs:25-27 and SEQ ID NOs:61-63 (antibody XBR2-401), (ii) SEQ ID NOs:28-30 and SEQ ID NOs:64-66 (antibody XBR2-416), (iii) SEQ ID NOs:31-33 and SEQ ID NOs:67-69 (antibody XBR2-433), (iv) SEQ ID NOs:34-36 and SEQ ID NOs:70-72 (antibody XBR2-327), (v) SEQ ID NOs:37-39 and SEQ ID NOs:73-75 (antibody XBR2-TOP9), (vi) SEQ ID NOs:40-42 and SEQ ID NOs:76-78 (antibody XBR2-TOP72), (vii) SEQ ID NOs:43-45 and SEQ ID NOs:79-81 (antibody ERR2-302), (vii) SEQ ID NOs:46-48 and SEQ ID NOs:82-84 (antibody ERR2-308), (ix) SEQ ID NOs:49-51 and SEQ ID NOs:85-87 (antibody ERR2-316), (x) SEQ ID NOs:52-54 and SEQ ID NOs:88-90 (antibody ERR2-317), (xi) SEQ ID NOs:55-57 and SEQ ID NOs:91-93 (antibody ERR2-TOP2), and (xii) SEQ ID NOs:58-60 and SEQ ID NOs:94-96 (antibody ERR2-TOP35). In some embodiments, the pharmaceutical composition includes an antibody having six CDR sequences of the same antibody exemplified in FIG. 1, e.g., (a) SEQ ID NOs:25-27 and SEQ ID NOs:61-63 (antibody XBR2-401); (b) SEQ ID NOs:28-30 and SEQ ID NOs:64-66 (antibody XBR2-416); or (c) SEQ ID NOs:31-33 and SEQ ID NOs:67-69 (antibody XBR2-433). Still another exemplary pharmaceutical composition includes a dsFv fragment, which can include one or more modifications to the amino acid sequence as appropriate and understood by one of ordinary skill in the art.

In some embodiments, the compositions of the invention contain a carrier for the antibody, the antibody fragment, the antibody-based binding protein or the ADC, desirably a pharmaceutically acceptable carrier. The pharmaceutically acceptable carrier can be any suitable pharmaceutically acceptable carrier. It can be one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. Pharmaceutically acceptable materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

Pharmaceutical compositions of the invention can additionally contain suitable buffering agents, including, for example, acetic acid in a salt, citric acid in a salt, boric acid in a salt, and phosphoric acid in a salt. The compositions can also optionally contain suitable preservatives, such as benzalkonium chloride, chlorobutanol, parabens, and thimerosal. Pharmaceutical compositions of the invention can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, PA.

Preparation of pharmaceutical compositions of the invention and their various routes of administration can be carried out in accordance with methods well known in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat.

Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The invention also provides kits suitable for carrying out the methods of the invention. Typically, the kits contain two or more components required for performing the therapeutic or diagnostic methods of the invention. Kit components include, but are not limited to, one or more antibodies, antibody-based binding proteins, antibody fragments thereof, or ADCs of the invention, appropriate reagents, and/or equipment. In some embodiments, the kits can contain an antibody, antibody-based binding protein, antibody fragment thereof, or ADC of the invention and an immunoassay buffer suitable for detecting ROR2 (e.g. by ELISA, flow cytometry, magnetic sorting, or FACS). The kit may also contain one or more microtiter plates, standards, assay diluents, wash buffers, adhesive plate covers, magnetic beads, magnets, and/or instructions for carrying out a method of the invention using the kit. The kit scan include an antibody, antibody-based binding protein, antibody fragment thereof of the invention bound to a substrate (e.g., a multi-well plate or a chip), which is suitably packaged and useful to detect ROR2. In some embodiments, the kits include an antibody, antibody-based binding protein, antibody fragment thereof of the invention that is conjugated to a label, such as, a fluorescent label, a biologically active enzyme label, a luminescent label, or a chromophore label. The kits can further include reagents for visualizing the conjugated antibody, antibody-based binding protein, antibody fragment thereof, e.g., a substrate for the enzyme. In some embodiments, the kits include an antibody or antigen-binding fragment of the invention that is conjugated to a contrast agent and, optionally, one or more reagents or pieces of equipment useful for imaging the antibody, antibody-based binding protein, antibody fragment thereof in a subject.

Generally the antibody, antibody-based binding protein, antibody fragment thereof or ADC of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use, or they can be provided at the concentration of use. For use of the antibody of the invention in vivo, single dosages may be provided in sterilized containers having the desired amount and concentration of components.

EXAMPLES

The following examples are provided to further illustrate the invention but not to limit its scope. Other variants of the invention will be readily apparent to one of ordinary skill in the art and are encompassed by the appended claims.

Example 1. Generation of Human ROR2-Specific Monoclonal Antibodies

Cell lines: MDA-MB-231 and T47D from ATCC were cultured in DMEM (Invitrogen; Carlsbad, CA) supplemented with 10% (v/v) heat inactivated FBS (Thermo Scientific; Logan, UT), 100 U/mL penicillin, and 100 μg/mL streptomycin (Invitrogen). Mouse pre-B cells 63-12 (Shinkai et al., Cell 68, 855-867, 1992), as well as the 63-12 cells ectopically expressing hROR1 or hROR2, were cultured in IMEM (Invitrogen) supplemented with 10% (v/v) heat inactivated FBS (Thermo Scientific), 0.1% (v/v) beta-ME, 100 U/mL penicillin, and 100 μg/mL streptomycin (Invitrogen). HEK 293F cells were purchased from Invitrogen and maintained in FreeStyle Medium supplemented with 1% (v/v) heat inactivated FBS (Thermo Scientific), 100 U/mL penicillin, and 100 μg/mL streptomycin (Invitrogen).

Cloning of full-length hROR2 mammalian expression vectors: Transposable vector backbones (pPB-Puro) were assembled from modular parts with flanking restriction sites that were synthesized or derived from sequence-verified commercially available vectors, and are described in detail in Patent WO2014013026A1. These original transposable vector backbones were modified by exchanging IRES-driven expression of the Puromycin resistance gene in the original vector with separate, phosphoglycerate kinase promoter (PGK) driven expression. This was done by replacing the IRES sequence with an SV40-pA sequence located 3' of the multiple cloning site, followed by introduction of the PGK-promoter sequence 5' of the Puromycin resistance gene. Full-length ROR2 open reading frames were synthesized by total gene synthesis (Genscript, Piscataway) with flanking restriction sites (5'NotI/3'BstBI) and were then cloned into the multiple cloning site of the transposable vectors using the respective restriction enzymes.

Cell line engineering for ectopic expression of hROR2 in the EMT-6 murine breast cancer cell line: Murine EMT-6 breast cancer cells (kind gift from Prof. Dr. med. Alfred Zippelius, University Hospital of Basel, Switzerland) were cultured in DMEM complete (Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept, Allschwil, Switzerland)) at 37° C. and 5% $CO_2$. Cells were engineered to overexpress human ROR2 by transposition as follows: cells were centrifuged (6 min, 1200 rpm, 4° C.) and resuspended in RPMI-1640 media ($5 \times 10^6$ cells/mL). 400 μL of this cell suspension was then added to 400 μL of RPMI containing 13.3 μg of transposable vector pPB-PGK-Puro-ROR2, directing co-expression of full-length human ROR2 (NP_004551.2) and the puromycin-resistance gene, and 6.6 μg of transposase-containing vector pCDNA3.1_hy_mPB. DNA/EMT-6 cell mixture was transferred to electroporation cuvettes (0.4 cm-gap, 165-2088, BioRad, Cressier, Switzerland) and electroporated using the Biorad Gene Pulser II with capacitance extender at 300V and 950 μF. Then, cells were incubated for 5-10 min at room-temperature. Following the incubation, cells were centrifuged at 1200 rpm for 6 min, washed once and subsequently resuspended in DMEM complete prior to incubation at 37° C. in a humidified incubator at 5% $CO_2$ atmosphere. One day after electroporation, cell pools stably expressing human ROR2 were selected by adding 3 μg/mL puromycin (Sigma-Aldrich, P8833).

ROR2 expression on selected EMT-6-ROR2 cells was confirmed by flow cytometry. Briefly, following trypsinization, $10^6$ cells were centrifuged in FACS tubes; obtained pellets were resuspended in buffer (PBS with 2% (v/v) FCS). Cells were then incubated with XBR2-401 (mAb003); 30 min, 4° C., final concentration 2 μg/mL), followed by centrifugation and washing. Cells were then resuspended as previously and incubated with anti-human IgG antibody (Fc gamma-specific) PE (eBioscience, Vienna, Austria, 12-4998-82) with a 1:250 dilution in the dark (30 min, 4° C.), washed once in buffer and kept on ice until FACS sorting.

Using a FACS Aria II, cells were single cell sorted into a 96-well flat-bottom plate containing 200 μL of DMEM complete per well. This plate was incubated at 37° C. and clones were expanded to 6-well plates before analysis of ROR2-expression by flow cytometry as outlined above, using a FACSCalibur instrument (BD Biosciences) and FlowJo analytical software (Tree Star, Ashland, OR) for analysis.

FIG. 15C shows the FACS analysis data of clone 14 (high ROR2-expressing) and WT (ROR2 negative) EMT-6, detected with anti-ROR2 antibody XBR2-401 (mAb003).

Example 2. Generation of High-Complexity Rabbit Fab Library and Reagents for Screening Construction, expression, purification, and biotinylation of recombinant human ROR2 protein hFc-hROR2-T$^{245}$: A human ROR2 cDNA from Thermo Scientific (Clone ID: 40/46553) was used as template. ROR2 has a single nucleotide polymorphism (SNP) at amino acid position 245. As part of the cloning, we mutated the less common alanine at position 245 of clone 40/46553 to the more frequent threonine. Briefly, two cDNA fragments encoding N-terminal and C-terminal portions of the extracellular domain (ECD) of ROR2 were PCR-amplified with (i) primers hROR2ECD_F (gcctaagcttgtctccgggtgccgaagtggaggttctggatccgaacg) (SEQ ID NO:97) and hROR2_A245T_R (gctcacgcggcttgggtgtccgggagcgcgcgtcgc) (SEQ ID NO:98) and (ii) primers hROR2_A245T_F (gcgacgcgcgctcccggacacccaagccgcgtgagc) (SEQ ID NO:99) and hROR2ECD_R (agctctcgagtcaccccatcttgctgctgtctcggggactacacgagg) (SEQ ID NO:100). Subsequently, the whole ROR2 ECD (amino acids 55-394) was assembled by overlap extension PCR using the flanking primers hROR2ECD_F and hROR2ECD_R and cloned into pCEP4-hFc (Hofer et al., 2008) via HindIII/XhoI. The resulting pCEP4-hFc-hROR2 construct was then transiently transfected into HEK 293F cells (Invitrogen) using 293fectin (Invitrogen) and conditions detailed in the manufacturer's protocol. Transfected cells were cultured in FreeStyle protein-free medium (Invitrogen) and the hFc-hROR2 fusion protein was purified from supernatants by Protein A affinity chromatography. Purified hFc-hROR2 was biotinylated using the Biotin-Tag Micro Biotinylation kit (Sigma-Aldrich). Briefly, 300 μg hFc-hROR2 in 50 μL of 0.1 M sodium phosphate buffer (pH 7.2) was incubated with 1 μL of 5 mg/mL biotinamidohexanoic acid 3-sulfo-N-hydroxysuccinide ester for 30 min at room temperature with gentle stirring. Biotinylated hFc-hROR2 was isolated using MicroSpin G-50 Columns provided by the kit.

Construction, expression, and purification of recombinant human ROR1 (hROR1-His) and human ROR2 (hROR2-His) proteins: hROR1-His was PCR-amplified with primers SP-hROR1_F (5' gctgggtaccggcgcgccaccatggactggacttggagaatcctgtttctcgtagctgctgcaactggagcacactccgcccgggg cgccgccgcccag 3') (SEQ ID NO:101) and hROR1-His_R (5' cggcctcgagtcagtgatggtgatggtggtgctccatcttgttcttctcctt 3') (SEQ ID NO:102) using pCEP4-hFc-hROR1 (Yang et al., 2011) as template, while hROR2-His was PCR-amplified with primers SP-hROR2_F (gctgggtaccggcgcgccaccatggactggacttggagaatcctgtttctcgtagctgctgcaactggagcacactccgaagtgga ggttctggatccg) (SEQ ID NO:103) and hROR2-His_R (cggcctcgagtcagtgatggtgatggtggtgccccatcttgctgctgtctcg) (SEQ ID NO:104) using pCEP4-hFc-hROR2 as template. Following cloning into pCEP4 (Invitrogen) separately via KpnI/XhoI, the constructs were transiently transfected into HEK 293F cells (Invitrogen) using 293fectin (Invitrogen), and the corresponding recombinant protein products were purified by Immobilized Metal Ion Affinity Chromatography using a 1-mL HisTrap column (GE Healthcare) as described (Kwong and Rader, 2009). The quality and quantity of purified hROR1-His and hROR2-His were analyzed by SDS-PAGE and A280 absorbance, respectively.

Generation and selection of naïve chimeric rabbit/human Fab libraries: All rabbit handling was carried out by veterinary personnel at Pocono Rabbit Farm & Laboratory (Canadensis, PA) or R & R Research (Stanwood, WA). A total of nine rabbits (ages 3-4 months) were used. Five of these rabbits were of the New Zealand White (NZW) strain, with three obtained from Pocono Rabbit Farm & Laboratory (Canadensis, PA) and two obtained from R & R Research (Stanwood, WA). Four b9 wild-type rabbits were derived from a separate R & R Research colony that originated from a pedigreed colony developed and characterized at the National Institute of Allergy and Infectious Diseases (NIAID) (McCartney-Francis et al., 1984; Popkov et al., 2003). Spleen and bone marrow from each rabbit were collected and processed for total RNA preparation and RT-PCR amplification of rabbit $V_\kappa$, $V_\lambda$, and $V_H$ encoding sequences using established protocols (Rader, 2009). Rabbit (rb) $V_\kappa$/human (hu) $C_\kappa$/rbV$_H$ and rbV$_\lambda$/huC$_\lambda$/rbV$_H$ segments, respectively, were assembled in one fusion step based on 3-fragment overlap extension PCR. Note that the $V_L$ derived from b9 rabbits were also assembled with $V_H$ from NZW rabbits. The Fab-encoding fragments were digested with SfiI and ligated with SfiI-treated phage display vector pC3C (Hofer et al., 2007) at 16° C. for 24 h. Subsequently, 15 μg purified pC3C-rbV$_\lambda$/hC$_\kappa$/rbV$_H$ ligated products were transformed into E. coli strain SR320 (a kind gift from Dr. Sachdev S. Sidhu, University of Toronto, Toronto, Ontario, Canada) by 30 separate electroporations (each using 0.5 μg DNA in 50 μl electrocompetent cells) and yielded 7.5×10$^9$ independent transformants for library κ. For library λ, 4.8×10$^9$ independent transformants were obtained using the same procedure. Using VCSM13 helper phage (Stratagene; La Jolla, CA), the phagemid libraries were converted to phage libraries and stored at −80° C. Phage library κ and library λ were re-amplified using XL1-Blue (Stratagene) or ER2738 (Lucigen) and mixed equally before four rounds of panning against biotinylated hFc-hROR2. During the panning, 5 μg/mL antigen was pre-incubated with streptavidin coated magnetic beads (Dynabeads MyOne Streptavidin C1; Invitrogen) at 37° C. for 30 min and then binders from the phage library were captured in the presence of 1 mg/mL unspecific polyclonal human IgG (Thermo Scientific). Starting from the third round of panning, the input phage was negatively depleted by incubation with empty beads before selection against antigen-loaded beads. Following selection, supernatants of IPTG-induced bacterial clones were analyzed by ELISA and by flow cytometry. Repeated clones were identified by DNA fingerprinting with AluI, and the $V_L$ and $V_H$ sequences of unique clones were determined by DNA sequencing (FIG. 1).

Example 3. Expression and Purification of Chimeric Rabbit/Human Fab and Full-Length IgG1 Antibodies Construction, expression, and purification of chimeric rabbit/human Fab and IgG1: MAbs XBR2-401, XBR2-416, and XBR2-433 in chimeric rabbit/human Fab format were cloned into E. coli expression plasmid pC3C-His and expressed and purified as described (Kwong and Rader, 2009). For the expression of mAbs XBR2-401, XBR2-416, and XBR2-433 in chimeric rabbit/human IgG1 format, the previously described vector PIGG-R11 was used (Yang et al., 2011). The various primer sequences used in the expression are shown in Table 1. The $V_H$ encoding sequences of Fab XBR2-401, XBR2-416, and XBR2-433 were PCR amplified using primers 4-1_VH_F and 4-1_VH_R, 4-16_VH_F and 4-16_VH_R, and 4-33_VH_F and 4-33_VH_R, respectively, and cloned via ApaI/SacI into PIGG-R11. The light chain encoding sequences of Fab 4-1, 4-16, and 4-33 were PCR amplified using primers 4-1_κ_F, 4-16_κ _F, and 4-33_λ_F, respectively, in combination with LEAD-B, and cloned via HindIII/XbaI into PIGG-R11 with the corresponding heavy chain encoding sequences. Note that an internal ApaI site in FR4 of $V_H$ encoding sequences of Fab XBR2-401 was removed by silent mutation in primer 4-1_VH_R. In addition, for, XBR2-416, and XBR2-433, we changed a TAG stop codon, which was suppressed during selection in *E. coli* strain XL1-Blue, to CAG (glutamine) encoding the first amino acid of native $V_H$ of both, XBR2-416, and XBR2-433 (FIG. 1) with primers 4-16_VH_F and 4-33_VH_F. The resulting PIGG-XBR2-401, PIGG-XBR2-416, and PIGG-XBR2-433 plasmids were transiently transfected into HEK 293F cells (Invitrogen) using 293fectin (Invitrogen), and the corresponding protein products were purified with a 1-mL recombinant Protein A HiTrap column (GE Healthcare, Piscataway, NJ) as described (Yang et al., 2011; Yang and Rader, 2012). The quality and quantity of purified IgG1 were analyzed by SDS-PAGE and A280 absorbance, respectively.

All the other mAbs in chimeric rabbit/human Fab format were cloned into *E. coli* expression plasmid pET11a and expressed and purified as described (Kwong and Rader, 2009) For the expression of mAbs ERR2-302, ERR2-308, ERR2-317, XBR2-327 and XBR2-TOP72 in chimeric rabbit/human IgG1 format, pCEP4 (Invitrogen) was used to clone the heavy chain and light chain separately. For heavy chain, a gBlock containing a heavy-chain signal peptide encoding sequence, $V_H$ of ERR2-302 and $C_H1$ (1-49) of human IgG1 was synthesized by IDT (San Jose, CA) and amplified with primers KpnI/AscI-Signal and CH1-internal/overlap-R, and fused to $C_H1$ (50-88)-$C_H2$-$C_H3$ amplified from PIGG with primers CH1-internal/overlap-F and HC-CH3-R-XhoI by overlap extension PCR with primers KpnI/AscI-Signal and HC-CH3-R-XhoI, and then cloned into pCEP4 by AscI/XhoI. Note that a NheI site was introduced into $C_H1$ at Ala$^{12}$ by synonymous mutation when the gBLOCK was synthesized. This construct served as vector to clone other mAb heavy chain by replacing the $V_H$ using AscI/NheI: $V_H$ of ERR2-308, ERR2-317, XBR2-327 and XBR2-TOP72 were amplified with forward primer ERR2-308 HC-F, ERR2-317 HC-F, XBR2-327 and ERR2-308 HC-F and reverse primer VH-CH1-R-EheI separately, followed by extension PCR to add the signal peptide with primer KpnI/AscI-Signal and VH-CH1-R-EheI. Then each $V_H$ was inserted into the vector by AscI/NheI. For light chain cloning, while lambda light chains of ERR2-302 and XBR2-TOP72 were amplified with primers ERR2-302 LC-F and XBR2-TOP72 LC-F separately combined with primer LC—R-XhoI, kappa light chains of ERR2-308, ERR2-317 and XBR2-327 were amplified with primers ERR2-308 KC-F, ERR2-317 KC-F and ERR2-317 KC-F separately combined with primer KC—R-XhoI. Then signal peptide was added by extension PCR with forward primer KpnI/AscI-Signal and reverse primer LC—R-XhoI or KC—R-XhoI. Subsequently, each light chain PCR products was cloned into pCEP4 by AscI/XhoI. The resulting constructs containing heavy chain or light chain for each IgG were co-transfected transiently into HEK 293F cells (Invitrogen) using 293fectin (Invitrogen), and the corresponding recombinant protein products were purified with a 1-mL recombinant Protein A HiTrap column (GE Healthcare, Piscataway, NJ) as described (Yang et al., 2011; Yang and Rader, 2012). The quality and quantity of purified IgG1 were analyzed by SDS-PAGE and $A_{280}$ absorbance, respectively.

TABLE 1

Primer sequences for cloning antibody sequences

| Primer | Sequence | SEQ ID NO: |
|---|---|---|
| 4-1_VH_F | GAGGAGGAGCTCACTC TCAGTCAGTGAAGGAG TCCGAGGGAG | 105 |
| 4-1_VH_R | CGATGGGCCCTTGGTG GAGGCTGAAGAGACGG TGACGAGGGTCCCTGG TCCCCAGATGTT | 106 |
| 4-16_VH_F | GAGGAGGAGCTCACTC TCAGGAGCAGCTGGAG GAGTCCGGG | 107 |
| 4-16_VH_R | CGATGGGCCCTTGGTG GAGGCTGAGGAGATGG TGACCAGGGTGCCTGG CCCCCACAAGTC | 108 |
| 4-33_VH_F | GAGGAGGAGCTCACTC TCAGTCAGTGAAGGAG TCCGAGGGA | 109 |
| 4-33_VH_R | CGATGGGCCCTTGGTG GAGGCTGAGGAGATGG TGACCAGGGTGCCTGG CCCCCAGATGTT | 110 |
| 4-1_κ_F | GAGAAGCTTGTTGCTC TGGATCTCTGGTGCCT ACGGGGACCCTATGCT GACCCAGACTCC | 111 |
| 4-16_κ_F | GAGAAGCTTGTTGCTC TGGATCTCTGGTGCCT ACGGGCAAGTGCTGAC CCAGACTCCATC | 112 |
| 4-33_λ_F | GAGAAGCTTGTTGCTC TGGATCTCTGGTGCCT ACGGGTCCTTCGTGCT GACTCAGCCAGC | 113 |
| LEAD-B | GGCCATGGCTGGTTGG GCAGC | 114 |
| KpnI/AscI-Signal | GGTACCGGCGCGCCAC CATGGACTGGACTTGG AGAATCCTGTTTCTCG TAGCTGCTGCAA | 115 |
| CH1-internal/overlap-R | GCCGCTGGTCAGGGCT CCTG | 116 |
| CH1-internal/overlap-F | CAGGAGCCCTGACCAG CGGC | 117 |
| HC-CH3-R-XhoI | GGCCTCGAGTCATTTA CCCGGAGACAGGGA | 118 |

TABLE 1-continued

Primer sequences for cloning antibody sequences

| Primer | Sequence | SEQ ID NO: |
|---|---|---|
| ERR2-308 HC-F | TTTCTCGTAGCTGCTG CAACTGGAGCACACTC CCAGGAGCAGCTGGAG GAGTCC | 119 |
| ERR2-317 HC-F | TTTCTCGTAGCTGCTG CAACTGGAGCACACTC CCAGTCGTTGGAGGAG TCCGGG | 120 |
| XBR2-327 HC-F | TTTCTCGTAGCTGCTG CAACTGGAGCACACTC CCAGGAGCAGCTGAAG GAGTCC | 121 |
| VH-CH1-R-EheI | GGAGGGCGCCAGGGGG AAGACCGATGGGCCCT TGGT | 122 |
| ERR2-302 LC-F | TTTCTCGTAGCTGCTG CAACTGGAGCACACTC CTCCTATGAGCTGACA CAGCTG | 123 |
| XBR2-TOP72 LC-F | TTTCTCGTAGCTGCTG CAACTGGAGCACACTC CCAGTTTGTGCTGACT CAGTCG | 124 |
| ERR2-308 KC-F | TTTCTCGTAGCTGCTG CAACTGGAGCACACTC CGACCCTATGCTGACC CAGACT | 125 |
| ERR2-317 KC-F | TTTCTCGTAGCTGCTG CAACTGGAGCACACTC CGACCCTGTGCTGACC CAGACT | 126 |
| LC-R-XhoI | GGCCTCGAGTTATGAA CATTCTGTAGGGGC | 127 |
| KC-R-XhoI. | GGCCTCGAGTTAACAC TCTCCCCTGTTGAA | 128 |

Example 4. Examination of Antibody Binding Activities

ELISA: Binding properties of the ROR2 antibodies were examined via ELISA. For coating, each well of a 96-well Costar 3690 plate (Corning, Corning, NY) was incubated with 100 ng antigen in 25 µL coating buffer (0.1 M $Na_2CO_3$, 0.1 M $NaHCO_3$, pH 9.6) for 1 h at 37° C. After blocking with 150 µL 3% (w/v) BSA/TBS for 1 h at 37° C., 100 ng/50 µL of Fab was added, incubated for 2 h at 37° C., washed with 150 µL PBS ten times and incubated with 50 µL of a 1:1000 dilution of a mouse anti-His tag mAb conjugated to horse radish peroxidase (HRP) (R&D Systems, Minneapolis, MN) in 1% (w/v) BSA/TBS for 1 h at 37° C. Washing with PBS was repeated and colorimetric detection was performed using 2,2'-azino-bis (3-ethylbenzthiazoline)-6-sulfonic acid (Roche) as substrate according to the manufacturer's directions. The absorbance was measured at 405 nm using a SpectraMax M5 microplate reader (Molecular Devices; Sunnyvale, CA) and SoftMax Pro software (Molecular Devices), as shown in FIG. 2A.

Flow cytometry: Antigen binding characteristics of the antibodies were also examined via flow cytometry analysis. Specifically, cells were stained using standard flow cytometry methodology. Briefly, for purified anti-ROR2 Fab, 0.1-1×10$^6$ cells were stained with 1 µg/100 µL of Fab on ice for 1 h. After washing twice with ice-cold flow cytometry buffer (PBS containing 1% (v/v) BSA, 0.1% sodium azide and 1 mM EDTA), the cells were incubated with a 1:1000 dilution of a mouse anti-His tag mAb conjugated to Alexa Fluor 488 (Qiagen) in 100 µL flow cytometry buffer on ice for 30 min. For purified anti-ROR2 IgG1, 0.1-1×10$^6$ cells were incubated with 100 ng/100 µL of IgG on ice for 1 h. After washing twice with ice-cold flow cytometry buffer, cells were stained with a 1:500 dilution of goat anti-human IgG, Fcγ pAbs conjugated to APC (Jackson ImmunoResearch) in 100 µL flow cytometry buffer on ice for 30 min. Finally, 4'6-diamidino-2-phenylindole (DAPI) was added to a final concentration of 100 ng/mL to exclude dead cells from analysis. Cells were analyzed using a FACSCalibur instrument (BD Biosciences) and FlowJo analytical software (Tree Star, Ashland, OR). Results of the study are shown in FIG. 2B, FIGS. 4-8, and FIG. 11.

Figure 4:
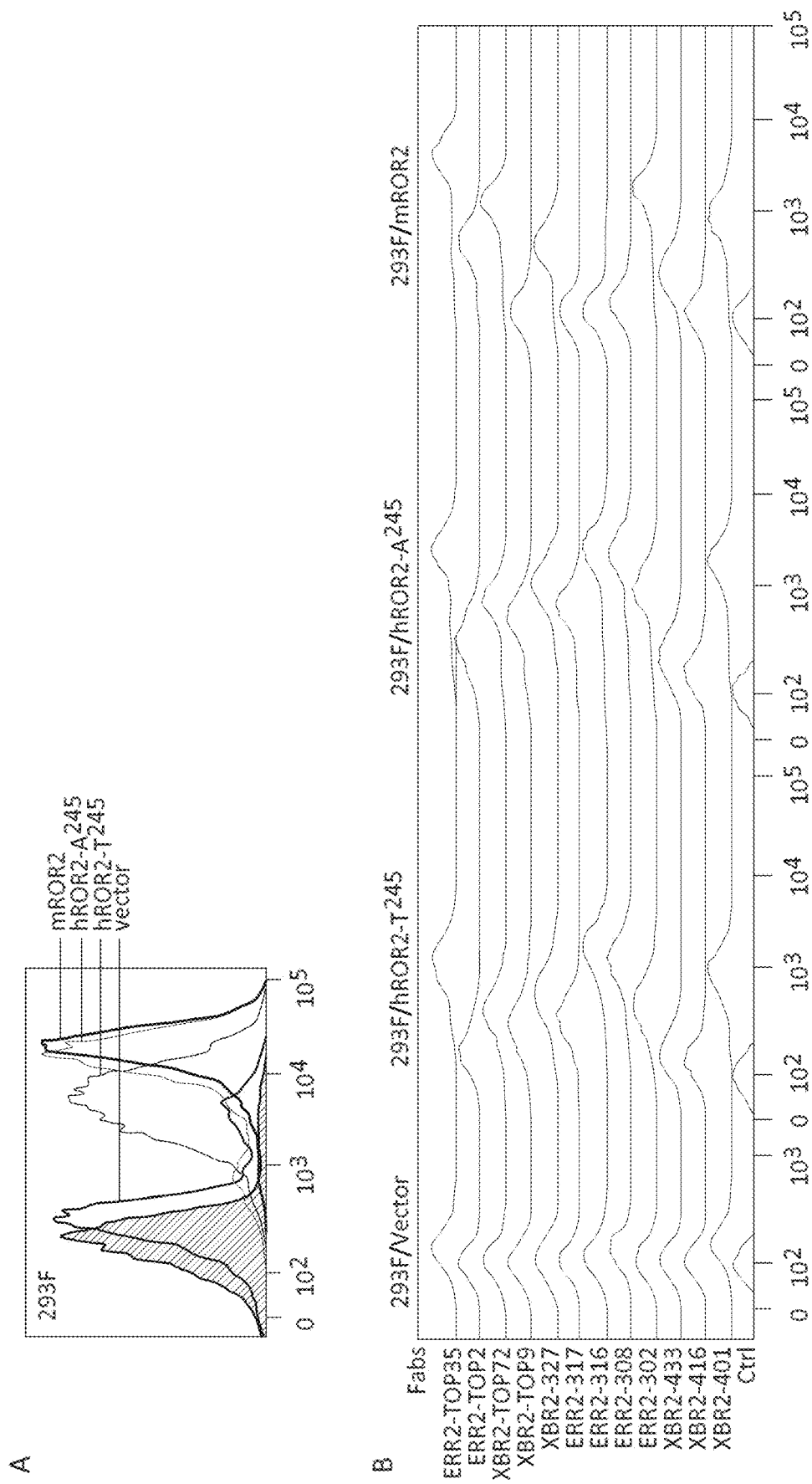
FIG. 4 shows binding of various antibodies to recombinantly expressed human ROR2 (hROR2). (A) The ectopic expression of hROR2 with different SNP at amino acid position 245 and mouse ROR2 (mROR2) in HEK 293F cells was detected by flow cytometry using a commercially available biotinylated rat anti-hemagglutinin (HA) monoclonal antibody (Roche) followed by phycoerythrin (PE)-conjugated streptavidin (BioLegend). (B) The binding of each novel chimeric rabbit/human Fab to hROR2-T245, hROR2-A245 and mROR2 displayed on the HEK 293F cell surface was analyzed by flow cytometry.
Figure 5:
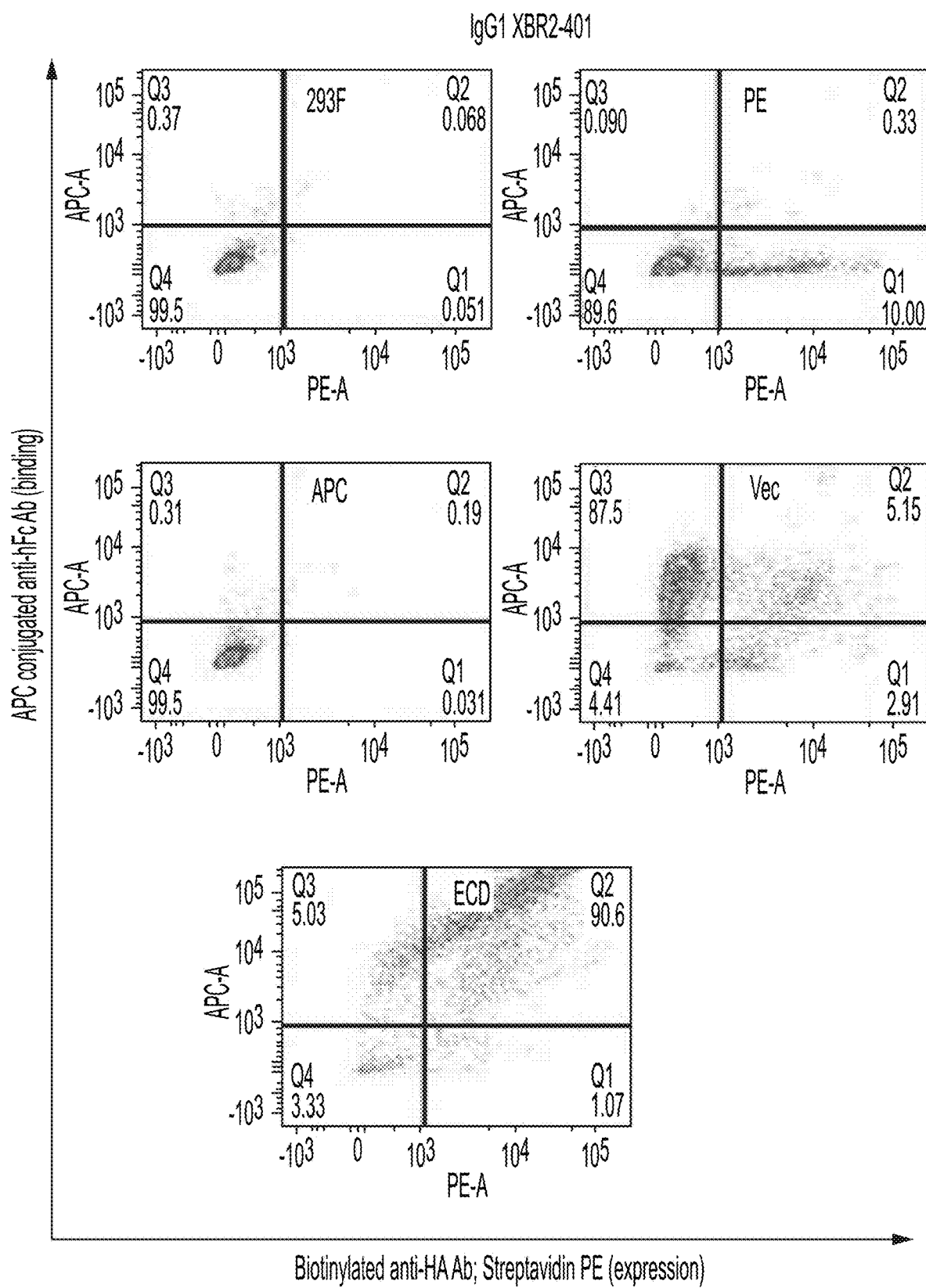
FIG. 5 shows epitope mapping studies for mAb XBR2-401 by flow cytometry. The epitope of chimeric rabbit/human IgG1 XBR2-401 was determined by flow cytometry using HEK 293F cells displaying different compositions of the three extracellular domains (Immunoglobulin, Frizzled and Kringle domain, abbreviated Ig, Fr and Ki) of hROR2-T245. Binding to hROR2 Ig, Fr, Ki, Ig+Fr, Fr+Ki and complete ECD (extracellular domain) expressed on HEK 293F cells was detected by flow cytometry.
Figure 5:
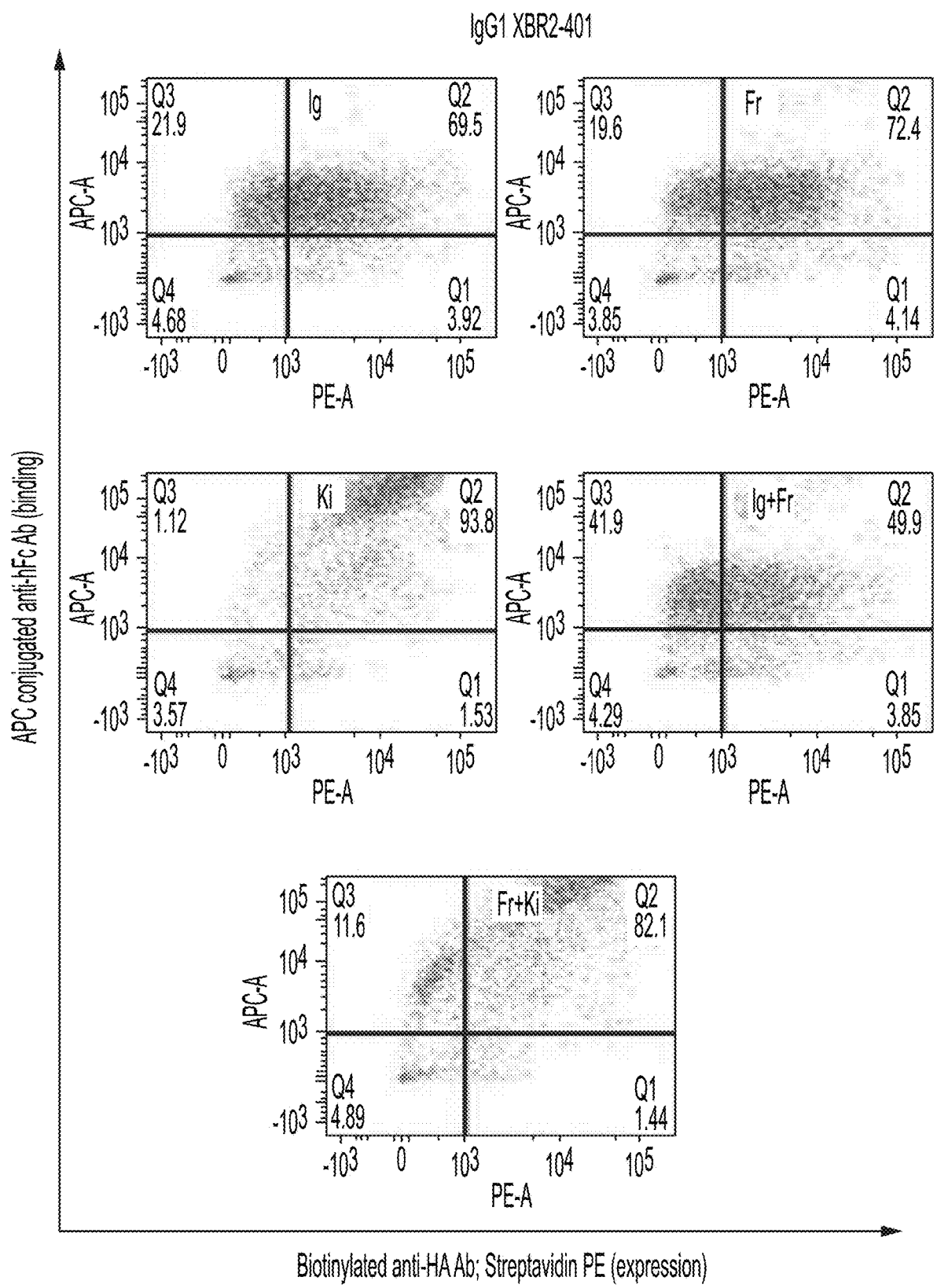
Figure 6:
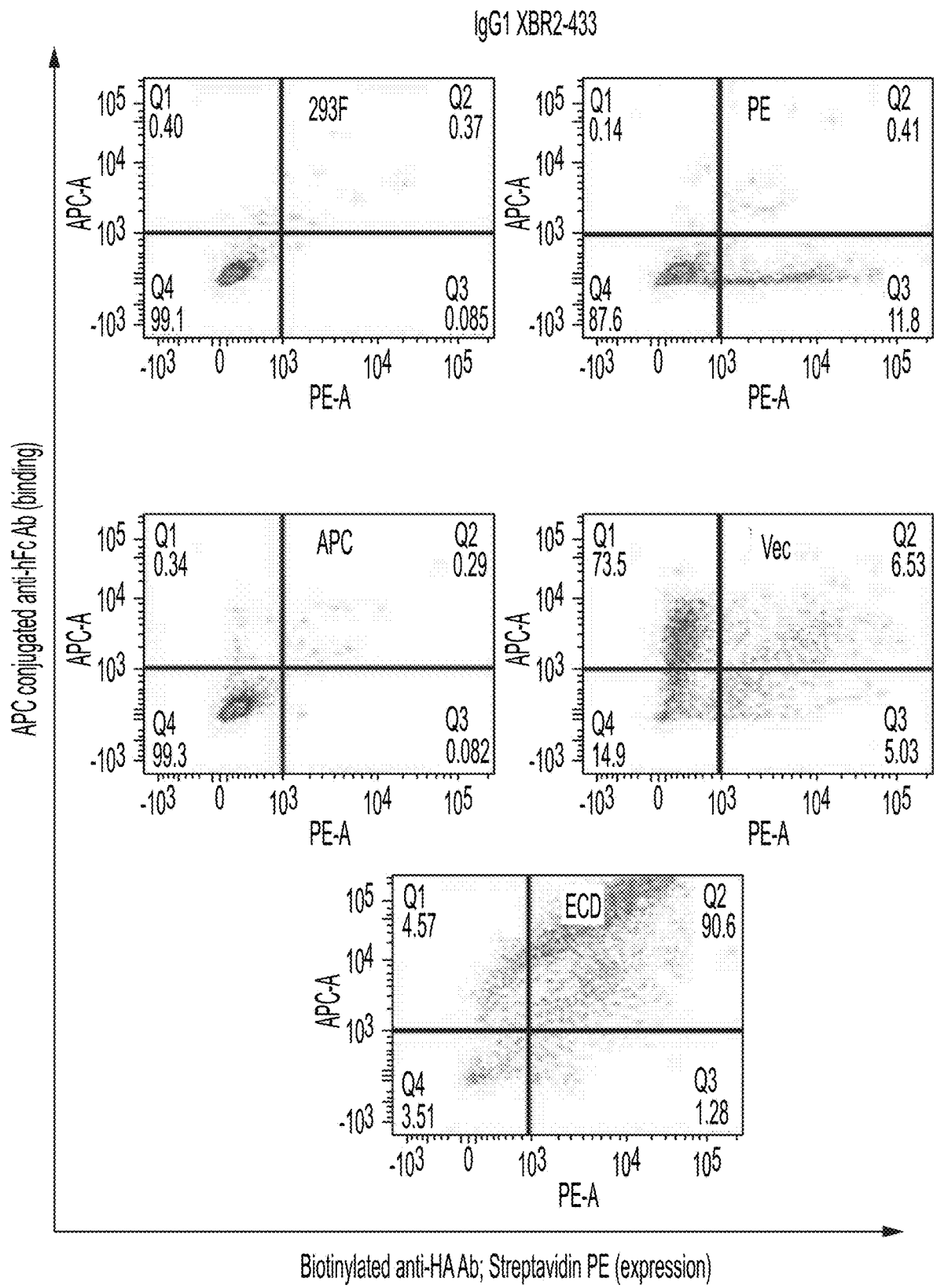
FIG. 6 shows epitope mapping studies for XBR2-433 by flow cytometry. The epitope of chimeric rabbit/human IgG1 XBR2-433 was determined by flow cytometry using HEK 293F cells displaying different compositions of the three extracellular domains (Immunoglobulin, Frizzled and Kringle domain, abbreviated Ig, Fr and Ki) of ROR2-T245. Binding to hROR2 Ig, Fr, Ki, Ig+Fr, Fr+Ki and complete ECD (extracellular domain) expressed on HEK 293F cells was detected by flow cytometry.
Figure 6:
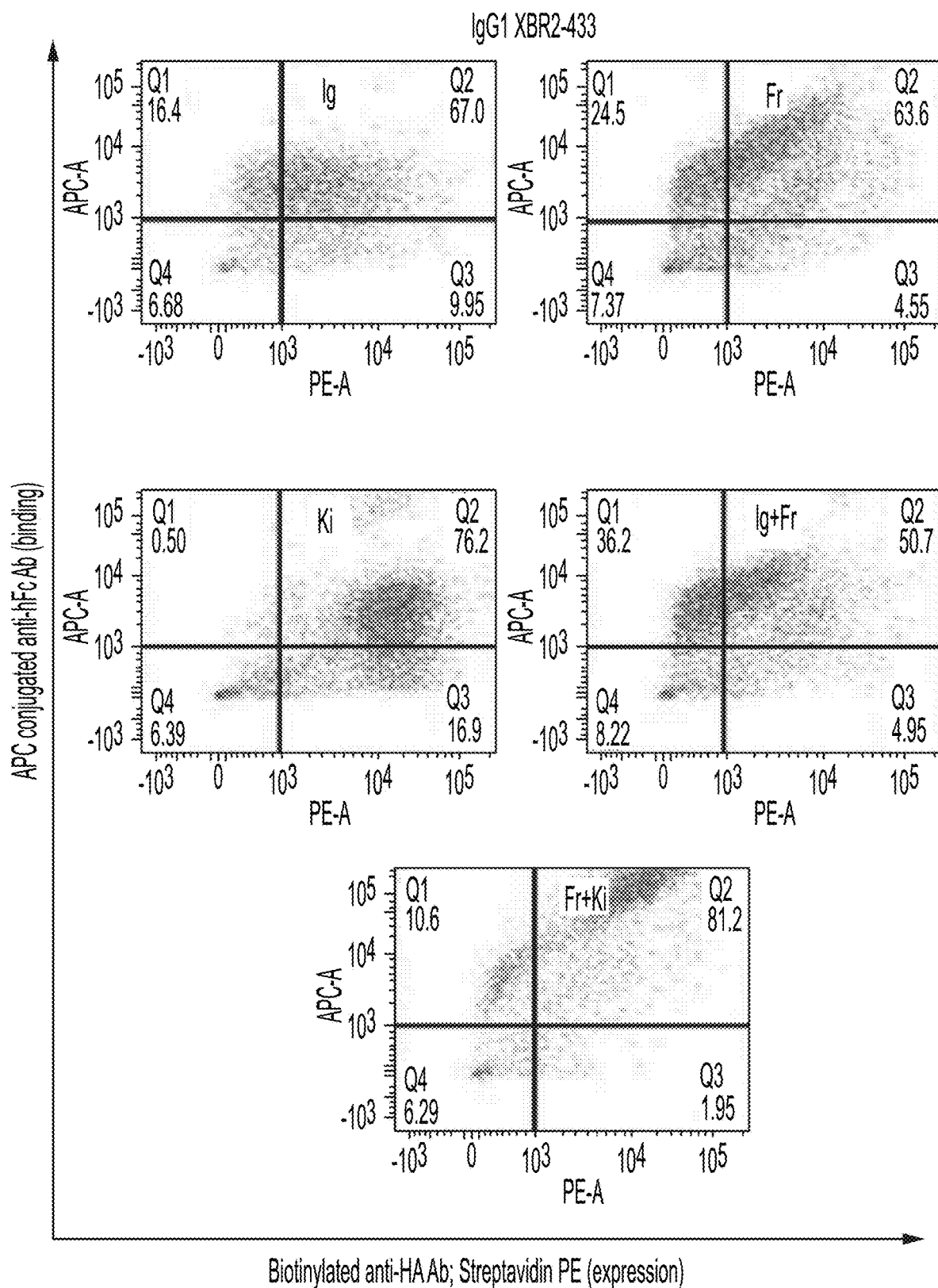
Figure 7:
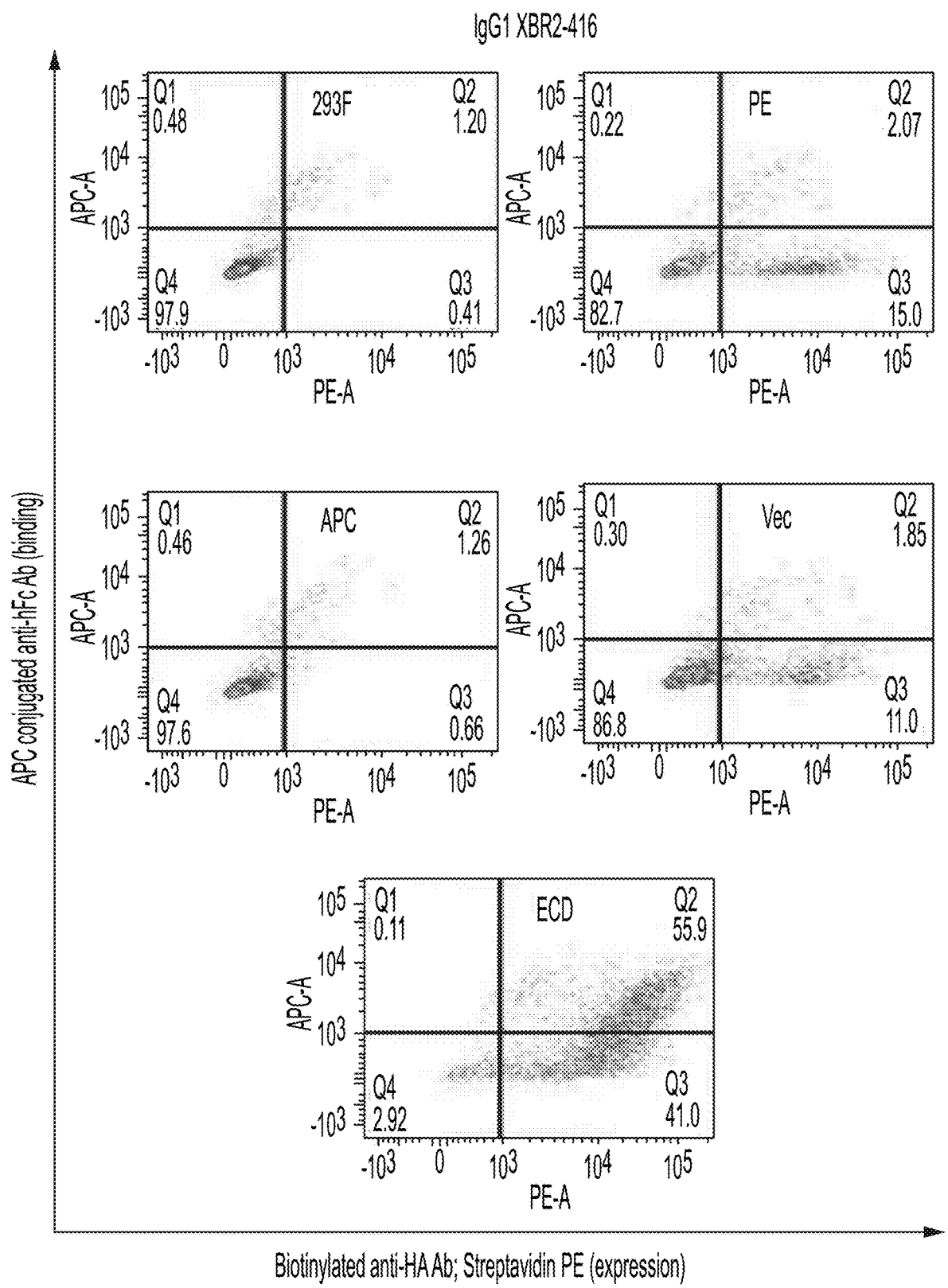
FIG. 7 shows epitope mapping studies for XBR2-416 by flow cytometry. The epitope of chimeric rabbit/human IgG1 XBR2-416 was determined by flow cytometry using HEK 293F cells displaying different compositions of the three extracellular domains (Immunoglobulin, Frizzled and Kringle domain, abbreviated Ig, Fr and Ki) of hROR2-T245. Binding to hROR2 Ig, Fr, Ki, Ig+Fr, Fr+Ki and complete ECD (extracellular domain) expressed on HEK 293F cells was detected by flow cytometry.
Figure 7:
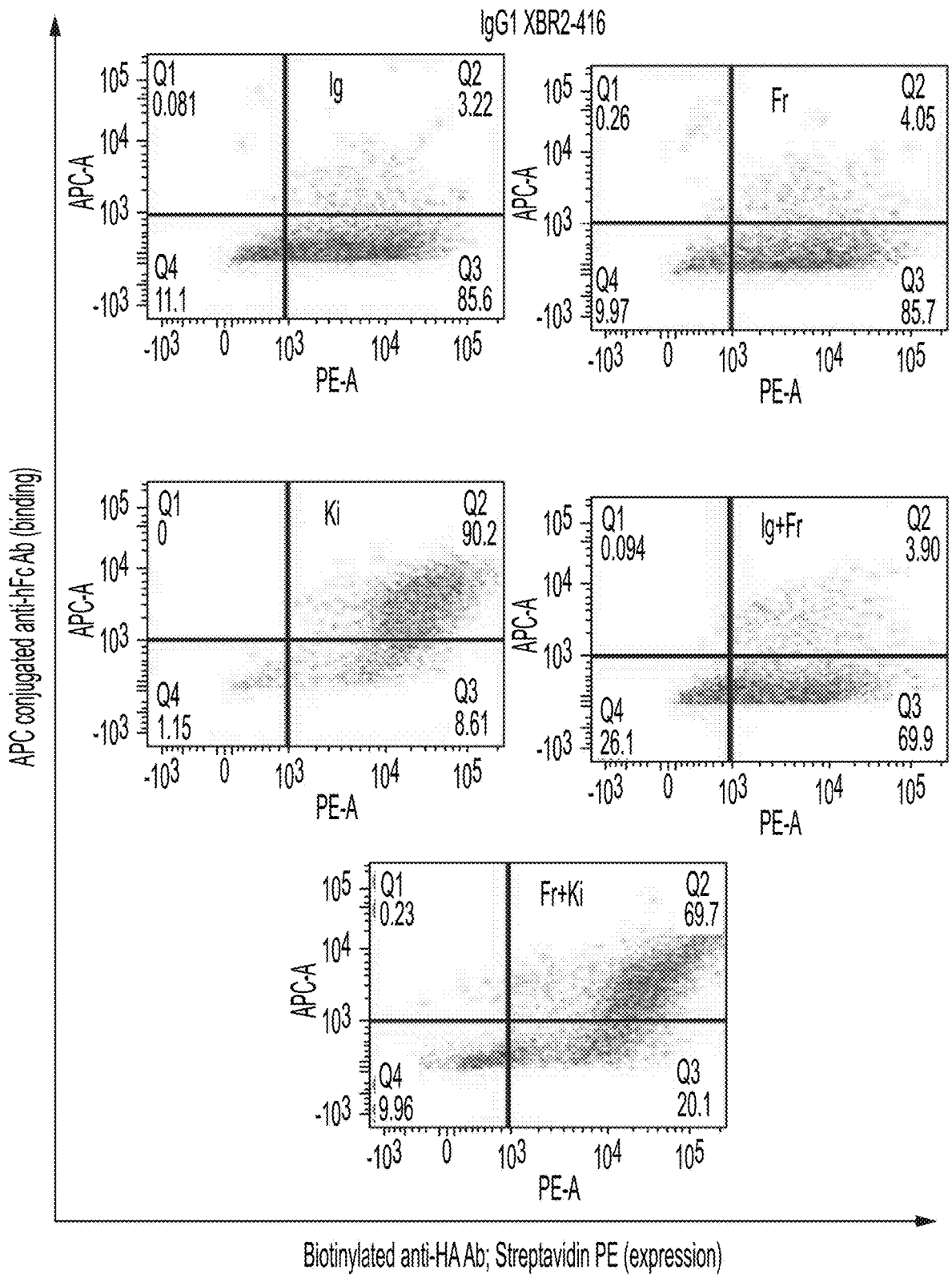
Figure 8:
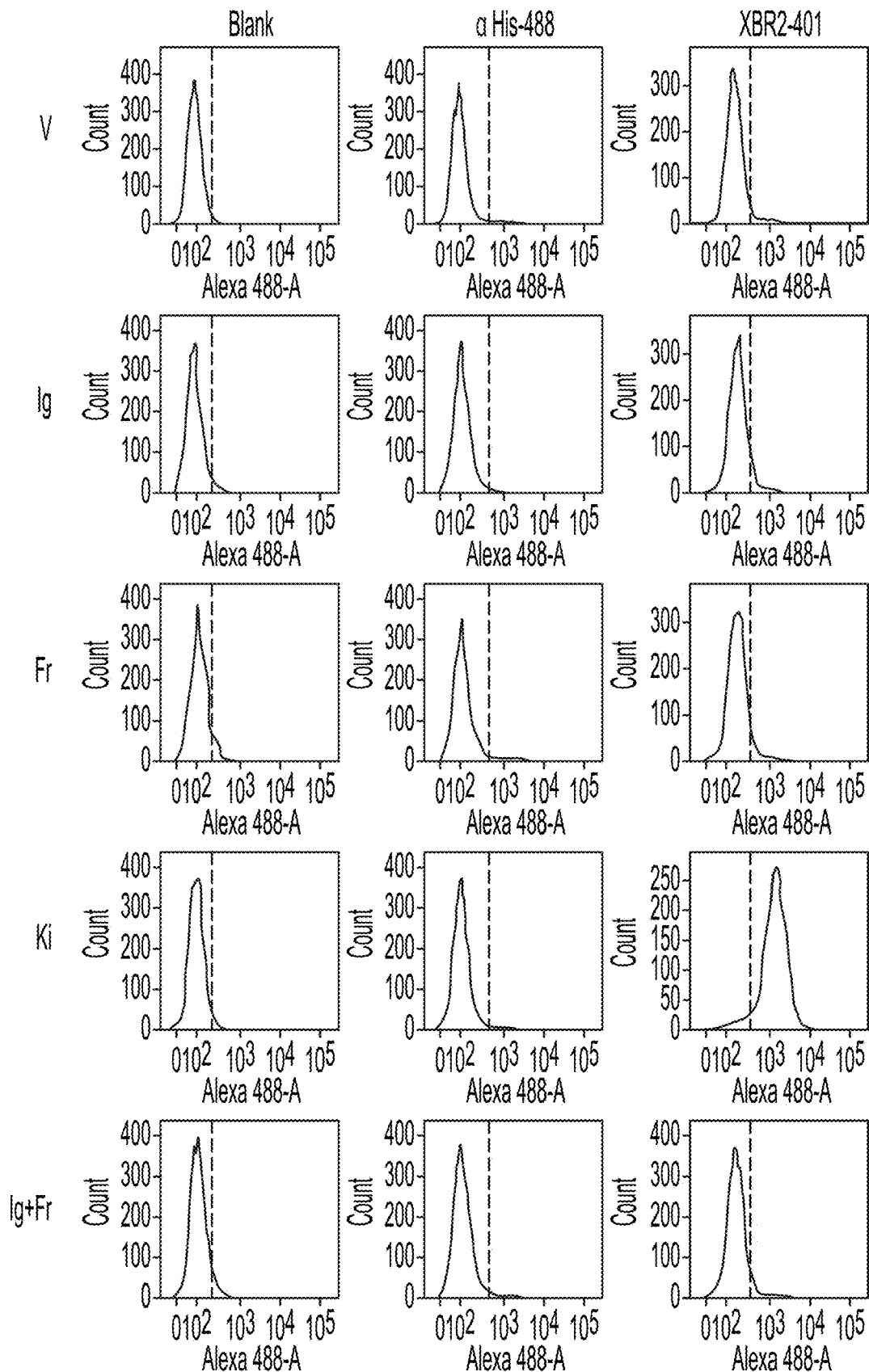
FIG. 8 shows epitope mapping studies for ten chimeric rabbit/human Fabs by flow cytometry. The epitopes of each chimeric rabbit/human Fab were determined by flow cytometry using HEK 293F cells displaying different compositions of the three extracellular domains (Immunoglobulin, Frizzled and Kringle domain, abbreviated Ig, Fr and Ki) of hROR2-T245. Binding to hROR2 Ig, Fr, Ki, Ig+Fr, Fr+Ki and complete ECD (extracellular domain) expressed on HEK 293F cells was detected by flow cytometry.
Figure 8:
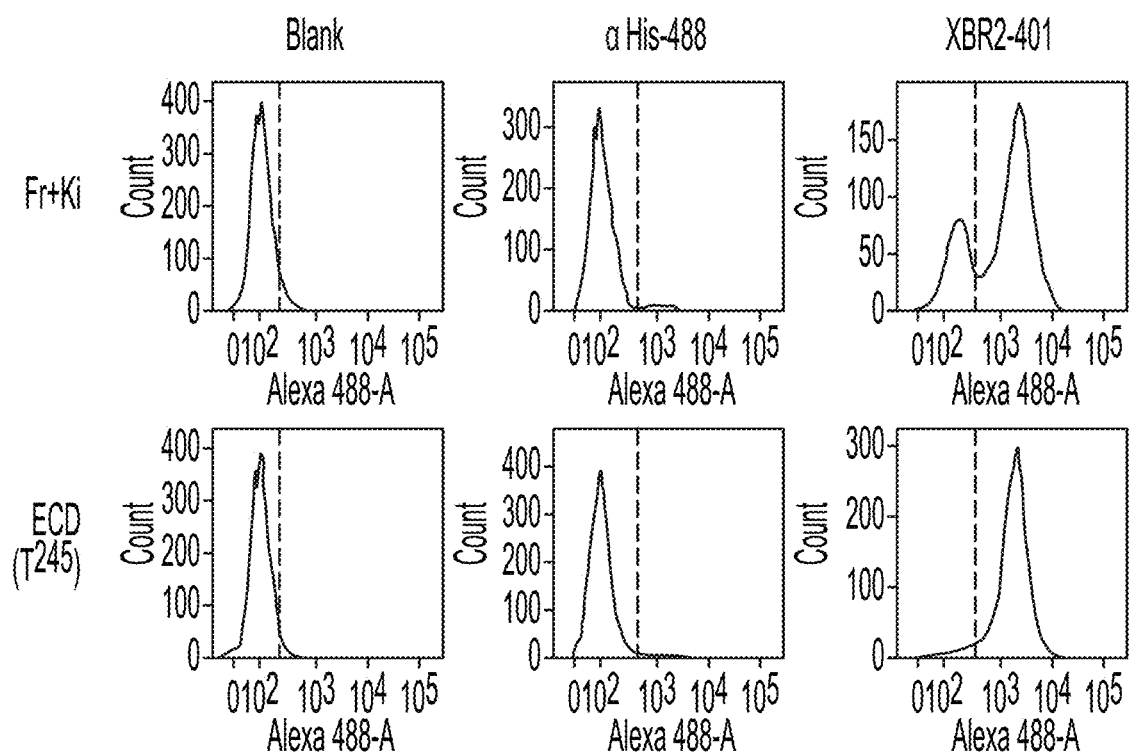
Figure 8:
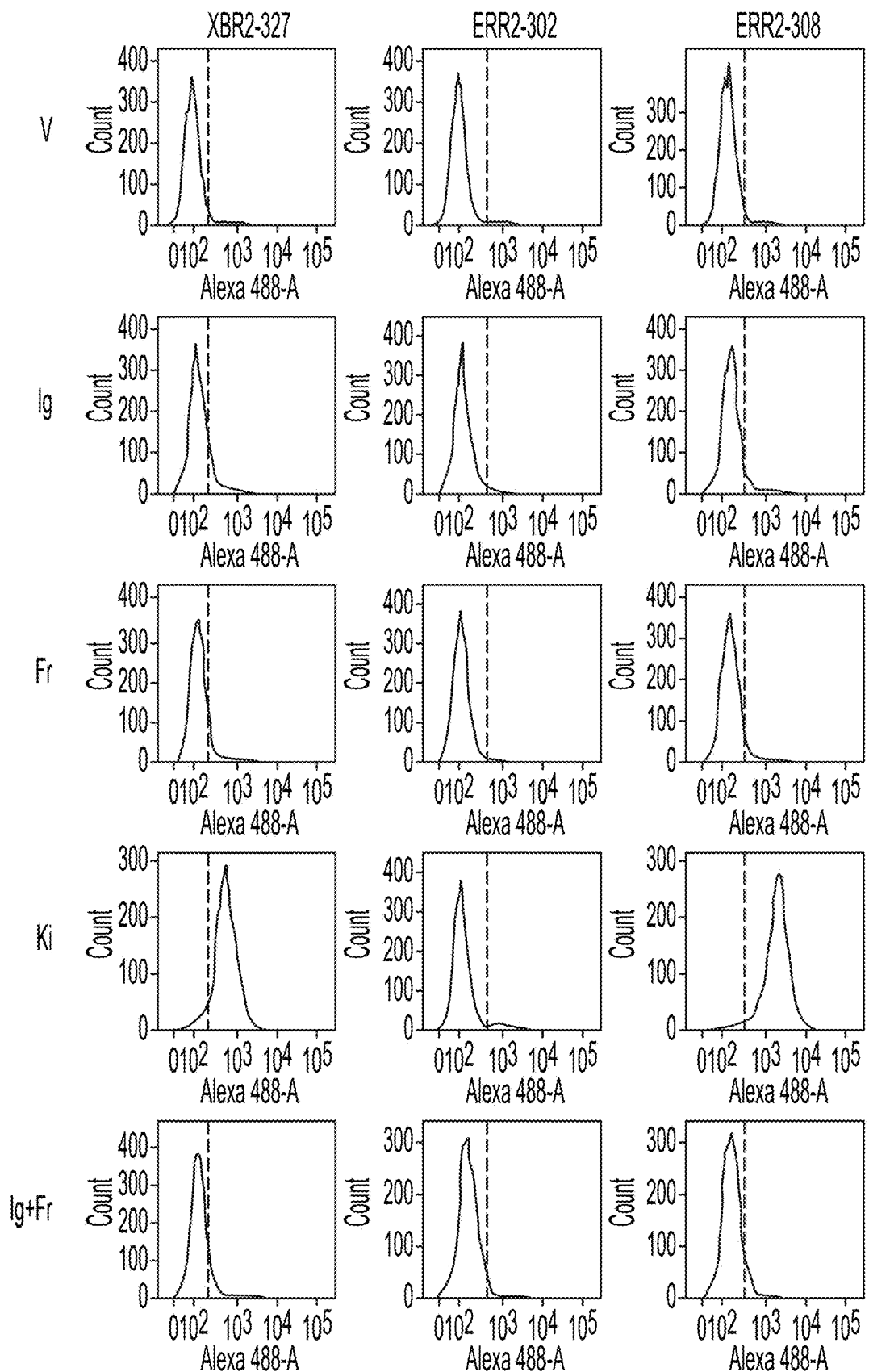
Figure 8:
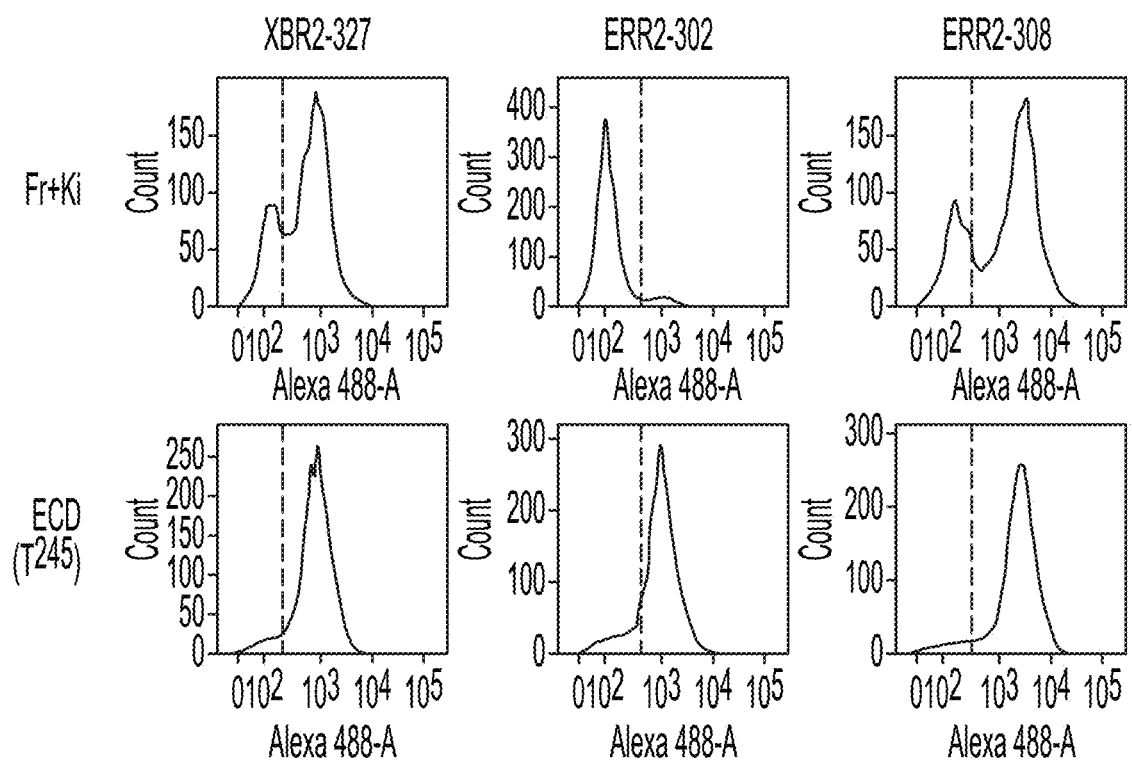
Figure 8:
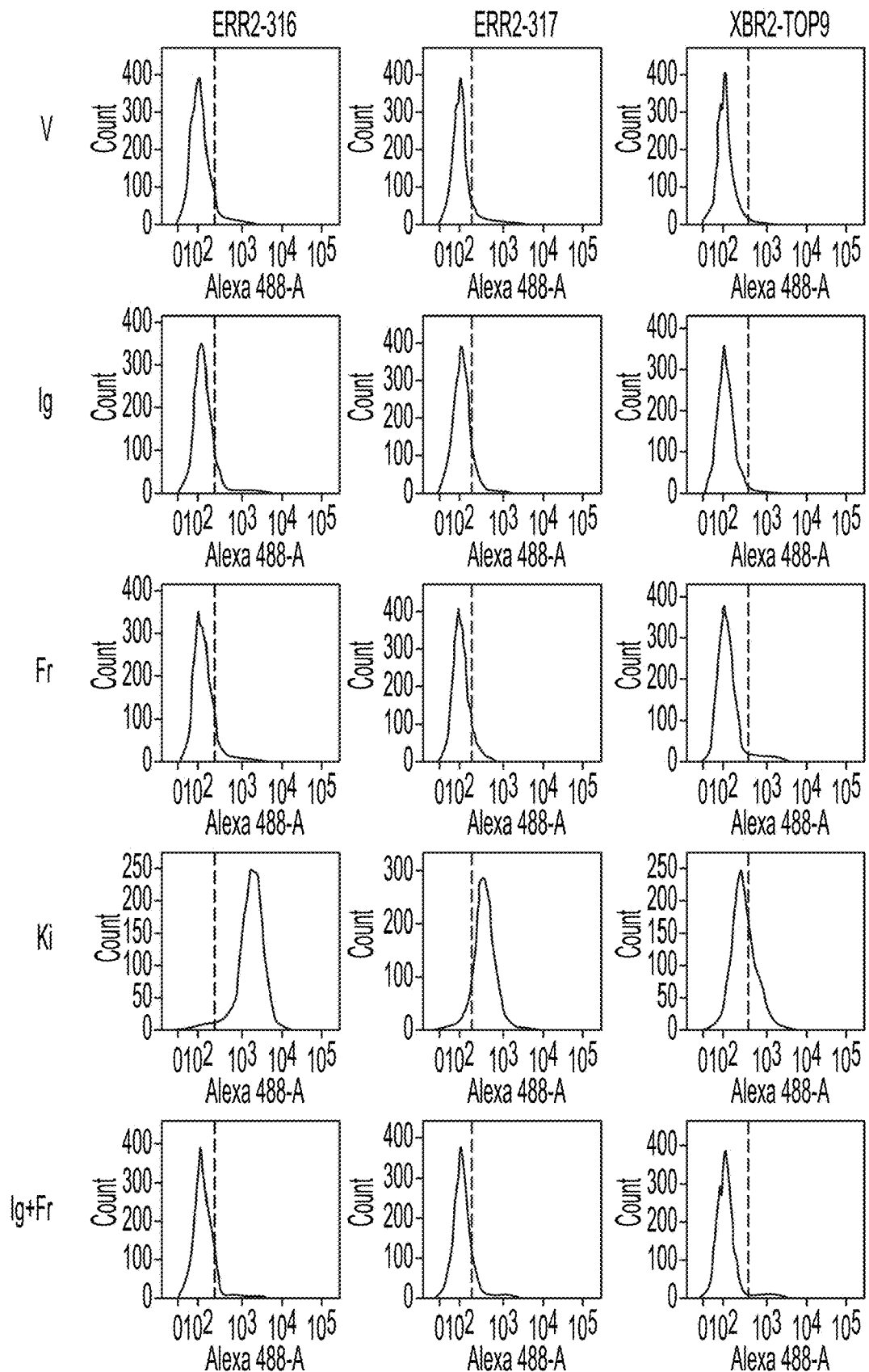
Figure 8:
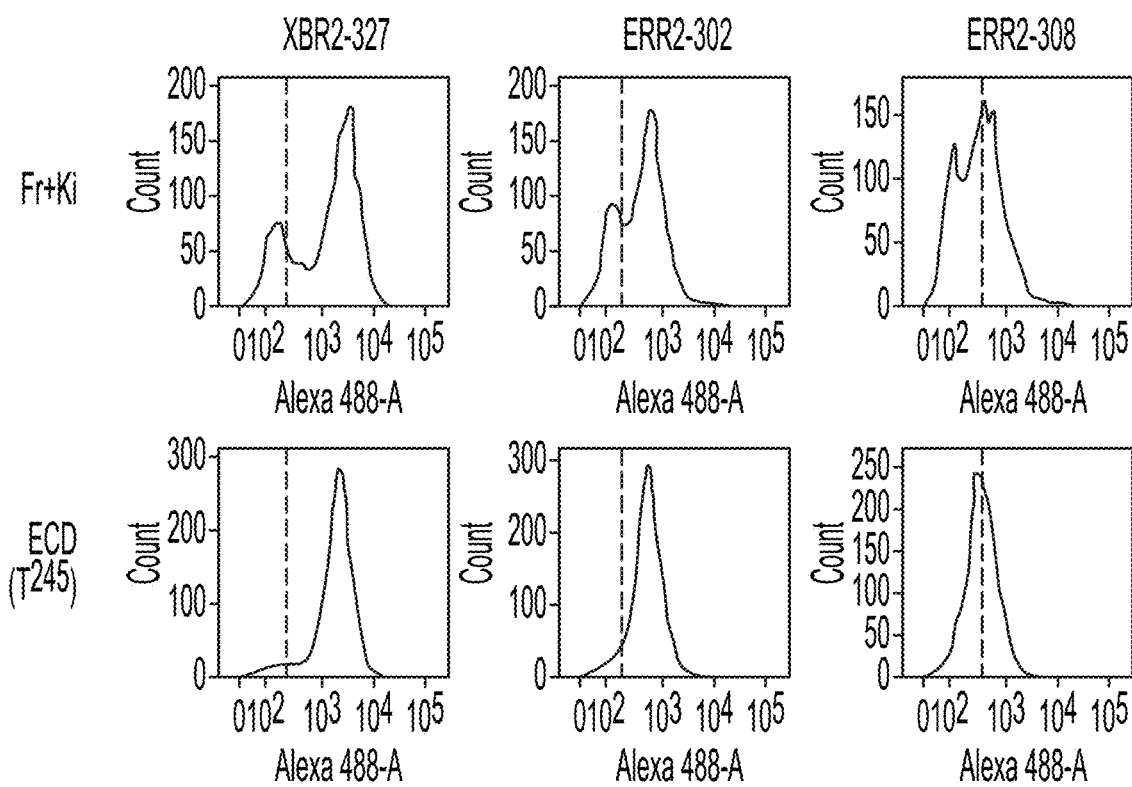
Figure 8:
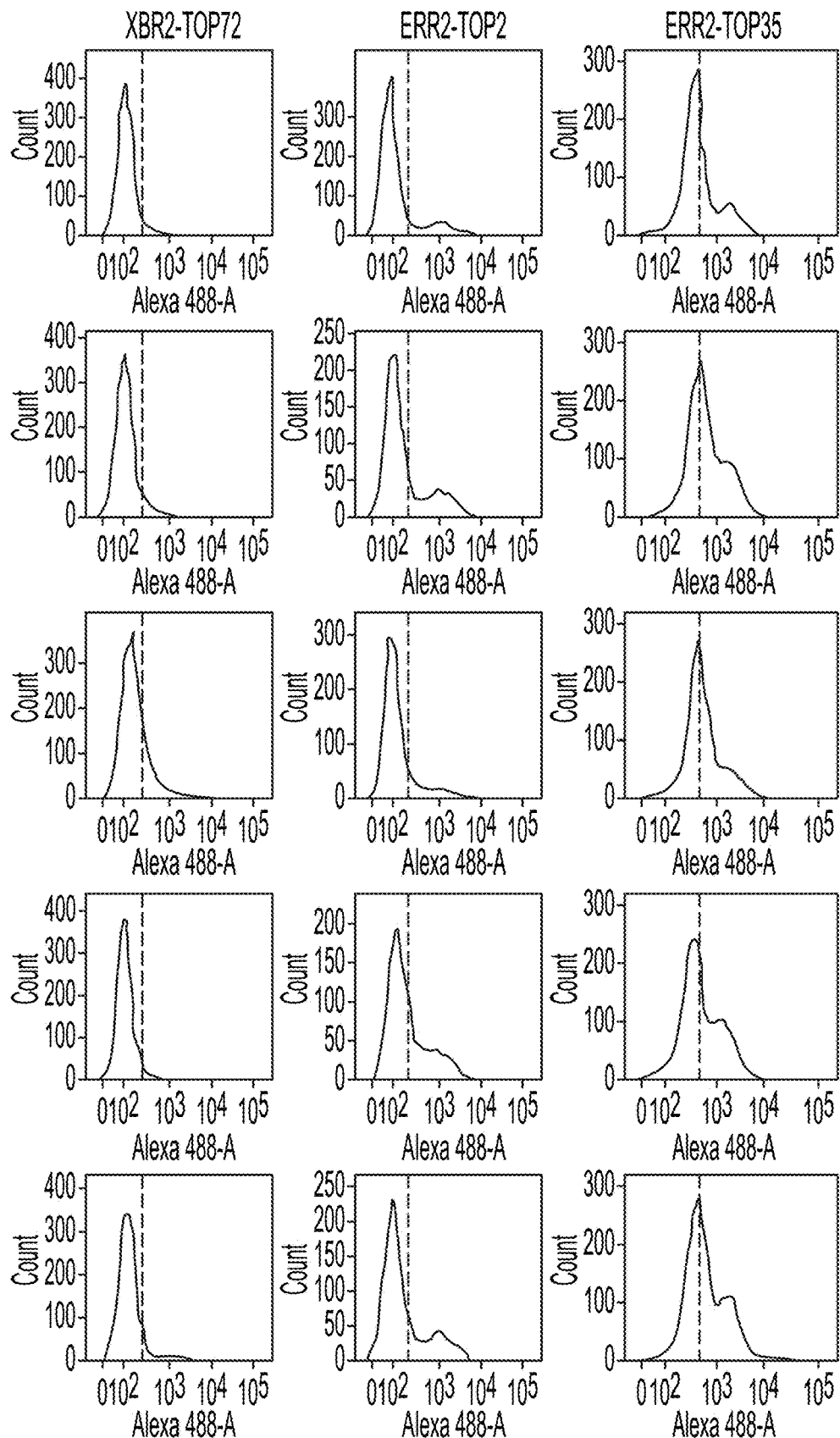
Figure 8:
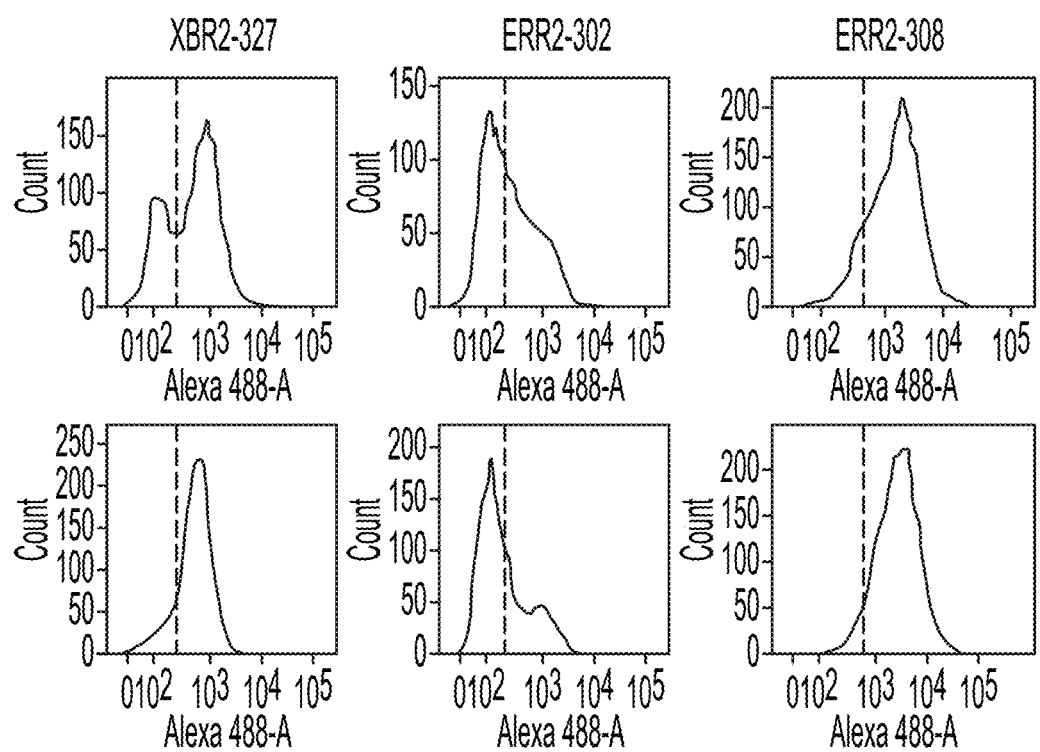

Additional studies were performed to examine cross-reactivity and epitope mapping of the isolated antibodies. In these studies, extracellular domains of human ROR2 with Thr at 145 (hROR2-T$^{245}$) (55-394) and human ROR2 with less frequent SNP hROR2-A$^{245}$ (55-394), as well as mouse ROR2 (34-403), were separately fused to a (G4S)$_3$ linker followed by an HA tag (YPYDVPDYAS) and a PDGFRB segment (amino acids 513-561) that included the transmembrane domain (amino acids 533-553), and stably displayed on HEK 293F cells (FIG. 3). Then, the cross reactivity of all the mAbs in chimeric rabbit/human Fab format to hROR2-T$^{245}$, hROR2-A$^{245}$ and mROR2 was tested by flow using these cells (FIG. 4). Similarly, different compositions of the three extracellular domains of hROR2-T$^{245}$, Ig (amino acids 55-145), Fr (169-303), Ki (316-394), Ig+Fr (55-303), Fr+Ki (169-394) were also stably displayed on HEK 293F cells separately (FIG. 3). Using these ROR2 domain displaying cell lines, the epitopes of mAbs XBR2-401 (FIG. 5), XBR2-433 (FIG. 6), and XBR2-416 (FIG. 7) were determined with chimeric rabbit/human IgG1 by flow cytometry. Briefly, 0.1~1×10$^6$ cells were incubated with purified (1 µg/mL) chimeric rabbit/human IgG1 on ice for 1 h. After washing twice with ice-cold flow cytometry buffer (PBS containing 1% (v/v) BSA, 0.1% sodium azide and 1 mM EDTA), the cells were incubated with a 1:500 dilution of goat anti-human IgG, Fcγ pAbs conjugated to APC (Jackson ImmunoResearch) in 100 µL flow cytometry buffer on ice for 30 min. After washing twice with ice-cold flow cytometry buffer, the cells were incubated with a 1:500 dilution of biotinylated rat anti-HA mAb 3F10 (Roche) in 100 µL flow cytometry buffer on ice for 1 h, washed as before, and stained with 2 µg/mL PE-conjugated streptavidin (BD Biosciences) on ice for 30 min. DAPI was added to a final concentration of 100 ng/mL to exclude dead cells from analysis. All the epitopes of other mAbs were determined with chimeric rabbit/human Fab by flow cytometry as the same procedure described above. Cells were analyzed using a FACSCalibur instrument (BD Biosciences) and FlowJo analytical software (Tree Star, Ashland, OR).

Figure 9:
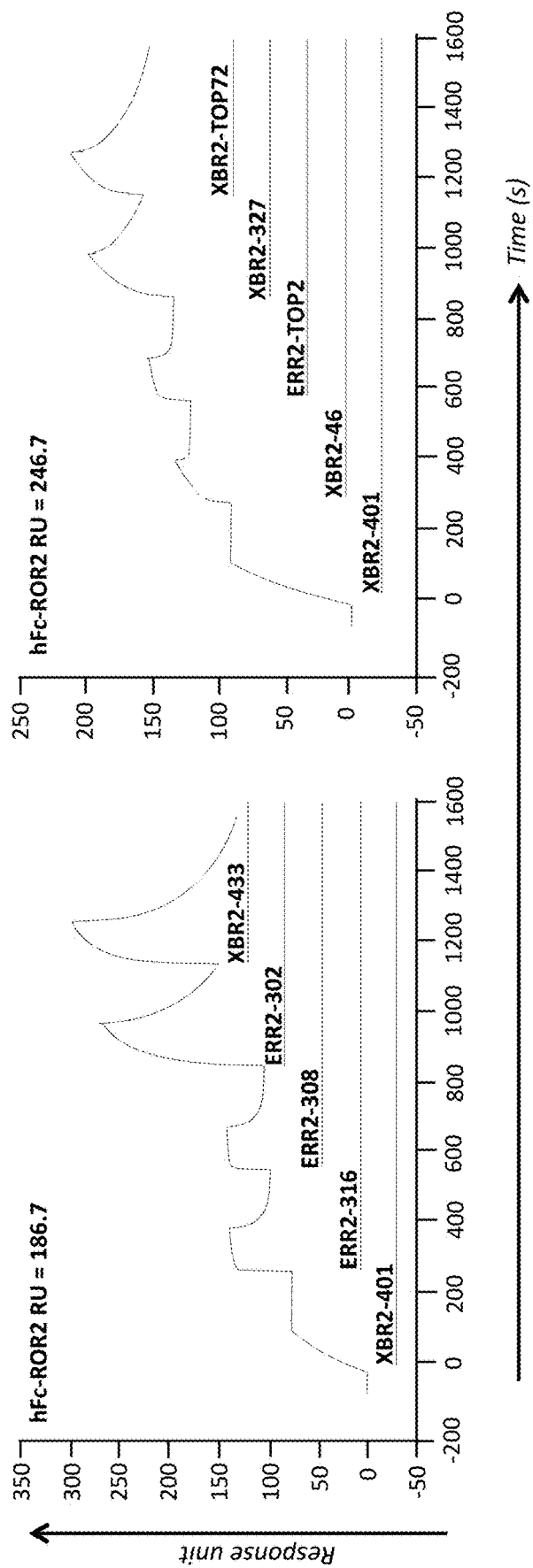
FIG. 9 shows epitope binding studies performed by surface plasmon resonance (SPR). Shown are SPR sensorgrams obtained for the binding of different Fabs to hFc-hROR2 captured by anti-human Fc-γ antibody immobilized on a CM5 chip. Fabs were injected in different orders and mixtures to identify independent and overlapping epitopes. Resonance unit (RU, y axis) increases that exceeded the values found for previously existed Fabs indicated independent epitopes because they allow simultaneous binding. For example, the RUs found for the combination of Fab XBR2-TOP72, XBR2-327, ERR2-TOP2, XBR2-416, and XBR2-401 (right graph) exceeded the values found for XBR2-401 alone or the combination of XBR2-327, ERR2-TOP2, XBR2-416, and XBR2-401, indicating that all those five Fabs can bind simultaneously to human ROR2 and therefore to different regions of the protein. The x axis depicts the time in seconds (s).

Surface plasmon resonance: Furthermore, a surface plasmon resonance study was performed to measure the affinities of all Fabs to hFc-hROR2 and epitope mapping studies were performed on a Biacore X100 instrument using Biacore reagents and software (GE Healthcare, Piscataway, NJ). Anti-Human IgG (Fc) antibody was immobilized on a CM5 sensor chip following the instruction of Human Antibody Capture Kit (GE Healthcare, Piscataway, NJ). Then hFc-hROR2 fusion proteins were captured at certain density (indicated in FIG. 9 and FIG. 10B). Each sensor chip included an empty flow cell for instantaneous background depletion. All binding assays used 1×HBS-EP+ running buffer (10 mM HEPES, 150 mM NaCl, 3 mM EDTA (pH 7.4), and 0.05% (v/v) Surfactant P20) and a flow rate of 30 mL/min. For affinity measurements, all Fabs were injected at five different concentrations (dilution factor was 2), with one of which was tested in duplicates (the highest concentrations for each Fab were indicated in FIG. 10B). The sensor chips were regenerated with 3 M $MgCl_2$ from the Human Antibody Capture Kit without any loss of binding capacity. Calculation of association ($k_{on}$) and dissociation ($k_{off}$) rate constants was based on a 1:1 Langmuir binding model. The equilibrium dissociation constant ($K_D$) was calculated from $k_{off}/k_{on}$. For epitope mapping studies, each Fab was prepared at 500 nM alone or in a mixture in 1×HBS-EP+ running buffer and then injected in order as indicated in FIG. 9.

Figure 12:
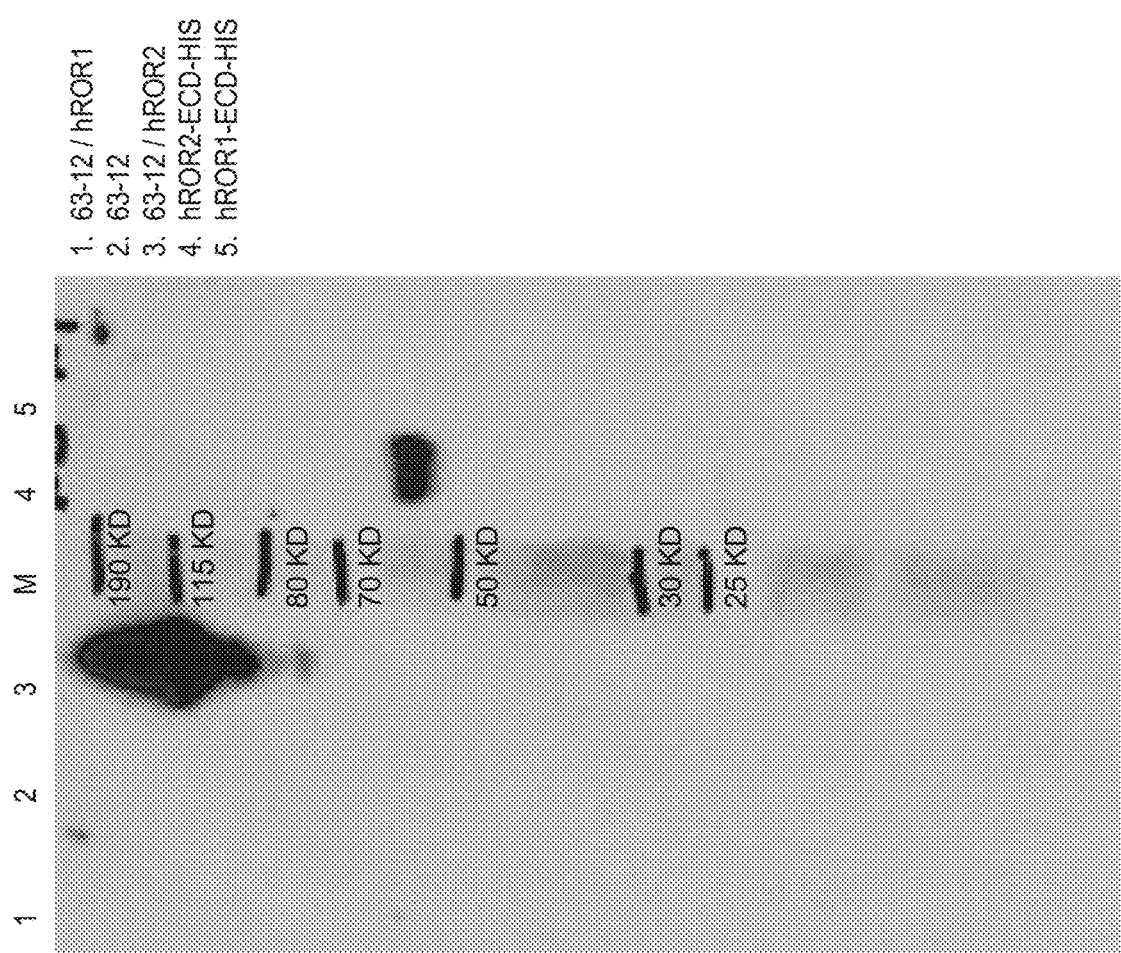
FIG. 12 shows the binding activity of chimeric rabbit/human IgG1 XBR2-401 to denatured hROR2 in Western-blotting experiments using lysates from non-transfected 63-12 cells (lane 2), as well as 63-12 cells ectopically expressing hROR1 (lane 1) or hROR2 (lane 3). In addition, Western-blotting was used to determine the binding to the purified extracellular domain of hROR2 (lane 4) or hROR1 (lane 5).

Western blotting: A Western blotting assay was performed to examine the binding activity of the isolated antibodies for denatured ROR2 polypeptide. Cells or proteins were lysed by 1× sample buffer (containing 1% β-mercaptoethanol) and boiled before running on NuPAGE Novex 4-12% Bis-Tris gels (Invitrogen). After membrane transferring and blocking by 5% milk, 2 µg/mL chimeric rabbit/human IgG1 XBR2-401 was applied to detect the denatured proteins, followed by incubation with 1/1000 anti-human Fc conjugated to HRP before developing using ECL Prime Western Blotting Detection Reagent (GE Healthcare). As shown in FIG. 12, the results indicate the antibody indeed recognizes denatured hROR2.

Example 5. Expression of Purified, Recombinant Twin Strep-Tagged Human, Murine and Cynomolgus ROR2

Twin strep-tagged human, mouse and cynomolgus ROR2-extracellular domain was produced as follows: the nucleotide sequence encoding the extracellular domain of human ROR2 (NP_004551.2), murine ROR2 (NP_038874.3) and cynomolgus ROR2 (XP_055582291.1) were each N-terminally fused to a signal sequence (MNFGLRLIFLVLTLKGVQC) and C-terminally fused with a sequence encoding a twin strep-tag (SAWSHPQFEKGGGSGGGSGGSAWSHPQFEKG). The entire nucleotide sequences with flanking 5'NotI and 3'HindIII sites were produced by total gene synthesis (GenScript, Piscataway, USA), assembled in the mammalian expression vector pCB14 and verified by DNA sequencing. This vector, a derivative of the episomal mammalian expression vector pCEP4 (Invitrogen), carries the EBV replication origin, encodes the EBV nuclear antigen (EBNA-1) to permit extrachromosomal replication, and contains a puromycin selection marker in place of the original hygromycin B resistance gene.

Recombinant human twin strep-tagged ROR2 (NP_004551.2), murine twin strep-tagged ROR2 (NP_038874.3) and cynomolgus twin strep-tagged ROR2 (XP_055582291.1) were expressed and purified in-house according to the following protocol: the EBNA expression vector pCB14b-ROR2-ECD-TwinStrep (human ROR2), pCB14g-mouseROR2-ECD-TwinStrep (mouse ROR2) or pCB14b-cynomolgusROR2-ECD-TwinStrep (cynomolgus monkey ROR2), directing expression of ROR2 extracellular domain (ECD), C-terminally tagged with a TwinStrep tag, was transfected into HEK293T using Lipofectamine® LTX with PLUS™ Reagent (Thermo Fisher Scientific, 15388100). Following a 1-day incubation (37° C., 5% $CO_2$, growth media: Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept)), cells were expanded under selection conditions (2 µg/mL of puromycin (Sigma-Aldrich, P8833-25 mg stock at 2 mg/mL)). Cells were split and further expanded (37° C., 5% $CO_2$); once confluency was reached, tissue culture dishes were coated with 20 µg/ml poly-L-Lysine (Sigma-Aldrich, P1524) for 2 hrs at 37° C. and washed twice with PBS. Then, cells were trypsinized, washed with PBS and split 1:3 onto poly-L-lysine-coated plates. Again after reaching confluency, cells were washed with PBS followed by with media replacement using production media (DMEM/F-12, Gibco/Thermo Fisher Scientific, 31330-03) supplemented with 1 µg/mL puromycin (Sigma-Aldrich, P8833), 100 IU/mL of Pen-Strep-Fungizone (Bioconcept, 4-02F00-H), 161 µg/mL of N-acetyl-L-cysteine (Sigma-Aldrich, A8199) and 10 µg/mL of L-glutathione reduced (Sigma-Aldrich, G6529). Supernatant, harvested bi-weekly and filtered (0.22 µm) to remove cells, was stored at 4° C. until purification. For purification, filtered supernatant was loaded onto a Streptactin® Superflow® high capacity cartridge (IBA, Gottingen, Germany, 2-1238-001) column; purification and elution was performed according to the manufacturer's protocol on an AEKTA pure (GE Healthcare). Fractions were analyzed for protein purity and integrity by SDS-PAGE. Protein-containing fractions were mixed and subjected to buffer exchange using Amicon filtration units (Millipore, Schaffhausen, Switzerland) to reach a dilution of ≥1:100 in PBS, and then sterile filtered using a low retention filter (0.20 µm, Carl Roth, Karlsruhe, Germany, PA 49.1).

Example 6. Expression of Purified, Recombinant Anti-Human ROR2 and Isotype Control Antibodies Expression vectors: Antibody variable region coding regions were produced by total gene synthesis (GenScript) using MNFGLRLIFLVLTLKGVQC as leader sequence, and were assembled with human IgH-γ 1 and IgL-κ (ERR2-308, ERR2-316, ERR2-317, XBR2-327, Huluc63) or IgL-λ (ERR2-302, ERR2-Top35) constant regions in the expression vector pCB14.

Expression vectors encoding each of the full-length heavy and light chains were assembled in a proprietary mammalian expression vector, Switzerland. Antibodies were transiently expressed in CHO cells by methods known in the art and recombinant antibodies were purified by standard protein A purification from CHO cell supernatants, as known in the art. In short, the CHO cell supernatants were harvested by centrifugation and sterile filtered (0.2 µm) before FPLC-based affinity purification using Amsphere protein A columns (JSR Life Sciences) performed as described below.

In-house expression and purification: pCB14-based expression vectors were transfected into HEK293T cells using Lipofectamine® LTX Reagent with PLUS™ Reagent (Thermo Fisher Scientific, Reinach, Switzerland, 15388100); following a 1-day incubation (37° C., 5% $CO_2$, growth media: Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept, Allschwil, Switzerland)), cells were expanded under selection conditions (2 µg/mL of puromycin (Sigma-Aldrich, Buchs SG, Switzerland, P8833-25 mg stock at 2 mg/mL)). Cells were split and further expanded (37° C., 5% $CO_2$); once confluency was reached, tissue culture dishes were coated with 20 µg/ml poly-L-Lysine (Sigma-Aldrich, P1524) for 2 h at 37° C. and washed twice with PBS. Then, cells were trypsinized and split 1:3 onto poly-L-lysine-coated plates. Again after reaching confluency, cells were washed with PBS followed by media replacement to production media (DMEM/F-12, Gibco/Thermo Fisher Scientific, 31330-03) supplemented with 1 µg/mL puromycin (Sigma, P8833), 100 IU/mL of Pen-Strep-Fungizone (Bioconcept), 161 µg/mL of N-acetyl-L-cysteine (Sigma-Aldrich, A8199) and 10 µg/mL of L-glutathione reduced (Sigma-Aldrich, G6529). Supernatant, harvested bi-weekly and filtered (0.22 µm) to remove cells, was stored at 4° C. until purification.

For purification, filtered supernatant was loaded onto a PBS-equilibrated Protein A HiTrap column (GE Healthcare, Frankfurt am Main, Germany, 17-0405-01) or a JSR Amsphere™ Protein A column (JSR Life Sciences, Leuven, Belgium, JWT203CE) and washed with PBS; elution was performed using 0.1 M glycine (pH 2.5) on an AEKTA pure (GE Healthcare). Fractions were immediately neutralized with 1 M Tris-HCl buffer (pH 8.0), and analyzed for protein purity and integrity by SDS-PAGE. Protein-containing fractions were mixed and subjected to buffer exchange using Amicon filtration units (Millipore, Schaffhausen, Switzerland, UFC901008) to reach a dilution of 1:100 in the buffer listed in Table 2, and then sterile filtered using a low retention filter (0.20 µm, Carl Roth, Karlsruhe, Germany, PA 49.1).

Table 2 lists the antibodies used in subsequent examples, along with their final concentration and buffer.

TABLE 2

List of antibodies used in the Examples

| Antibody (ref.) | Antibody SEQ ID HC/LC | C-Terminal Tags (HC: Heavy Chain, LC: Light Chain) | Buffer | Final conc. (mg/mL) |
|---|---|---|---|---|
| ERR2-302 (mAb004) | HC: SEQ ID NO. 7 LC: SEQ ID NO. 19 | HC: LPETG-Strep LC: $G_5$SLPETG-Strep | PBS | 2.7 |
| ERR2-308 (mAb037) | HC: SEQ ID NO. 8 LC: SEQ ID NO. 20 | HC: LPETG-Strep LC: $G_5$SLPETG-Strep | PBS | 4.5 |
| ERR2-316 (mAb005) | HC: SEQ ID NO. 9 LC: SEQ ID NO. 21 | HC: LPETG-Strep LC: $G_5$SLPETG-Strep | PBS | 3.2 |
| ERR2-317 (mAb006) | HC: SEQ ID NO. 10 LC: SEQ ID NO. 22 | HC: LPETG-Strep LC: $G_5$SLPETG-Strep | PBS | 2.5 |
| XBR2-327 (mAb007) | HC: SEQ ID NO. 4 LC: SEQ ID NO. 16 | HC: LPETG-Strep LC: $G_5$SLPETG-Strep | PBS | 3.7 |
| ERR2-top35 (mAb130) | HC: SEQ ID NO. 12 LC: SEQ ID NO. 24 | HC: LPETG-Strep LC: $G_5$SLPETG-Strep | PBS | 3.3 |
| XBR2-401 (mAb003) | HC: SEQ ID NO. 11 LC: SEQ ID NO. 13 | HC: LPETG-Strep LC: $G_5$SLPETG-Strep | PBS | 6.0 |
| Huluc63 (mAb047) | HC: SEQ ID NO. 135 LC: SEQ ID NO. 136 | HC: LPETG-Strep LC: $G_5$SLPETG-Strep | PBS | 8.0 |

Huluc63 corresponds to an unrelated control antibody; the heavy and light chain sequences are given below.

| SEQ ID NO. Name | Amino Acid Sequence (with constant domain underlined) |
|---|---|
| SEQ ID NO. 135 Huluc63 HC amino acid sequence | EVQLVESGGGLVQPGGSLRLSCAASGFDFSRYWMSWV RQAPGKGLEWIGEINPDSSTINYAPSLKDKFIISRDN AKNSLYLQMNSLRAEDTAVYYCARPDGNYWYFDVWGQ GTLVTVSS<u>ASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSRDELTKNQVSLTCL VKGFYPSDIAVEWESNGQPENNYKTTPPVLDSDGSFF LYSKLTVDKSRWQQGNVFSCSVMHEALHNHYTQKSLS LSPGK</u> |
| SEQ ID NO. 136 Huluc63 LC amino acid sequence | DIQMTQSPSSLSASVGDRVTITCKASQDVGIAVAWYQ QKPGKVPKLLIYWASTRHTGVPDRFSGSGSGTDFTLT ISSLQPEDVATYYCQQYSSYPYTFGQGTKVEI<u>KRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC</u> |

Example 7. Cross-Reactivity of Anti-Human ROR2 Antibodies on Murine and Cynomolgus ROR2

Each well of a 96-well plate was coated with 50 µL of 2 µg/mL twinstrep-tagged human, murine or cynomolgus ROR2 (from Example 4) in 0.1 M bicarbonate coating buffer (pH 9.6), and incubated for 12 h at 4° C. An additional 96-well plate was likewise prepared but with anti-human Fc (Jackson ImmunoResearch, 109-006-008).

Figure 14:
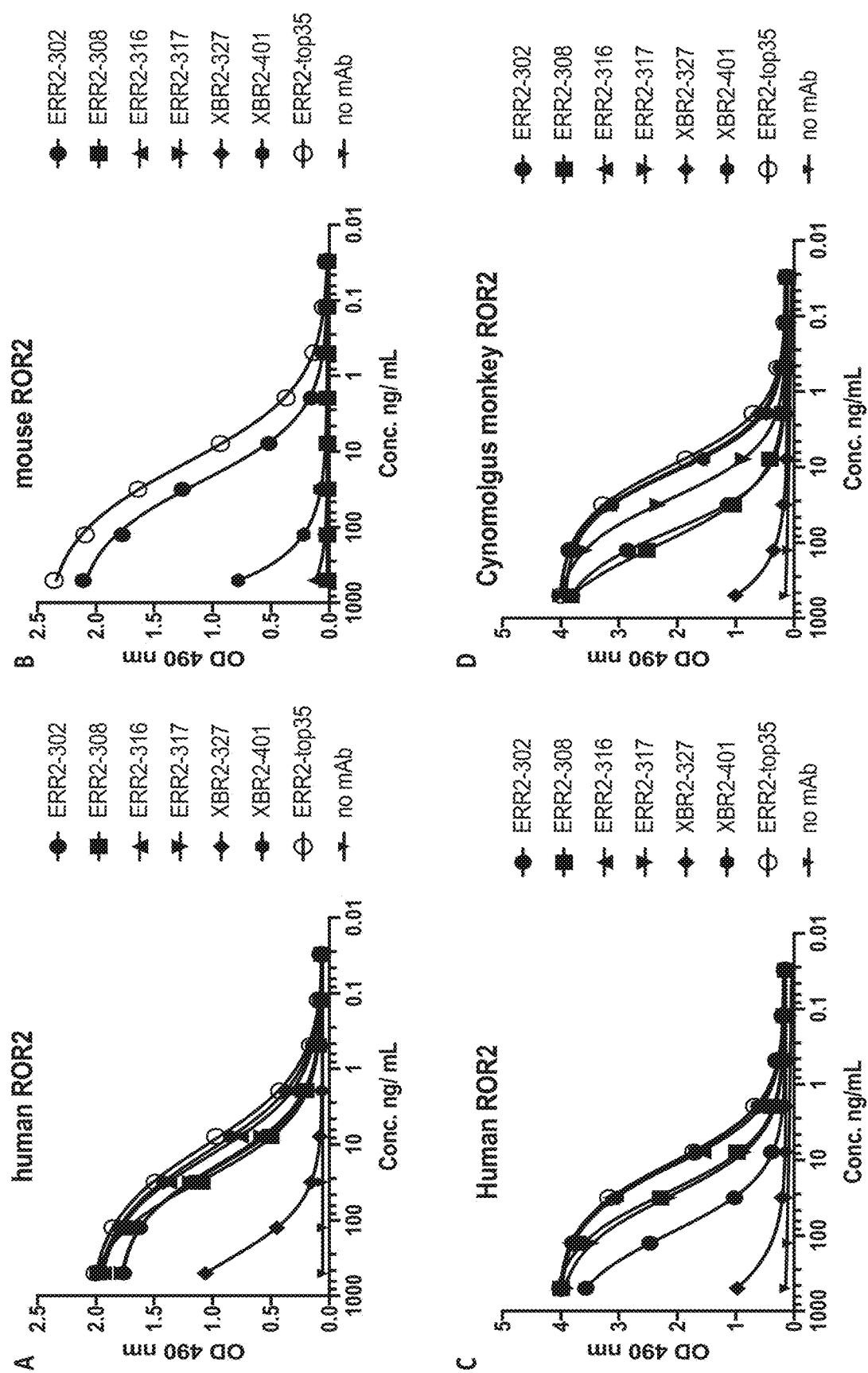
FIG. 14 shows binding of full length IgG1 antibodies to recombinant ECD of human and mouse ROR2. Panels (A) and (B) show the binding specificity of selected clones of the invention expressed as full-length chimeric rabbit-human IgG1 antibodies to purified, recombinant ECD of human and mouse ROR2 analyzed by ELISA. Panels (C) and (D) show the binding specificity of selected clones of the invention expressed as full-length chimeric rabbit-human IgG1 antibodies to purified, recombinant ECD of human and cynomolgus ROR2 analyzed by ELISA.

After blocking with 150 µL of 3% (w/v) bovine serum albumin (BSA)/TBS for 1 h at 37° C., the following antibodies were added to a well within each plate at a concentration of 0.5 µg/mL, and serially diluted (dilution factor 4) with 1% (w/v) BSA/TBS, before incubation for 1 h at 37° C.: ERR2-302 (mAb004), ERR2-308 (mAb037), ERR2-316 (mAb0005), ERR2-317 (mAb006), XBR2-327 (mAb007), ERR2-Top35 (mab130), and XBR2-401 (mab003). After washing with PBS with 0.05% Tween 20, HRP-conjugated F(ab')$_2$ anti-human FC-gamma (Jackson Immunoresearch, 109-036-008) was then added at a 1:10'000 dilution, 50 µl per well, and incubated for 1 h at 37° C. prior to detection using an Spark 10M plate reader (Tecan). Curves of OD 490 nm versus antibody concentration (ng/mL) were fitted with Graphpad Prism Software (Graphpad Software, La Jolla, CA, U.S.A.). The $IC_{50}$ values, determined using the built-in "log(inhibitor) vs. response—Variable slope (four parameters)" $IC_{50}$ determination function of Prism Software, are reported in Table 3 for human and mouse ROR2, and in Table 4 for human and cynomolgus ROR2. As shown in FIG. 14, the anti-human ROR2 antibodies ERR2-302 and ERR2-Top35 bind human ROR2 (panel A, C) and mouse ROR2 (panel B); the remaining are not cross-reactive with mouse ROR2. All of the inventive anti-human ROR2 antibodies are, however, cross-reactive with cynomolgus ROR2 (panel D).

TABLE 3

Human and mouse ROR2 binding by anti-ROR2 antibodies.

| | IC50 ng/mL | | | ratio IC50 | |
| --- | --- | --- | --- | --- | --- |
| Antibody | anti-human Fc | human ROR2 | mouse ROR2 | human ROR2/IgG | mouse ROR2/IgG |
| ERR2-302 | 32.2 | 102.3 | 60.6 | 0.31 | 0.53 |
| ERR2-308 | 33.6 | 466.8 | 150.7 | 0.07 | 0.22 |
| ERR2-316 | 40 | 29.9 | 994.6 | 1.34 | 0.04 |
| ERR2-317 | 39.1 | 1354.1 | 167.2 | 0.03 | 0.23 |
| XBR2-327 | 43.3 | 167901.4 | 443.7 | 0 | 0.1 |
| XBR2-401 | 85.6 | 50.5 | 361.1 | 1.69 | 0.24 |
| ERR2-top35 | 41.9 | 24.4 | 17.3 | 1.72 | 2.41 |

TABLE 4

Human and cynomolgus ROR2 binding by anti-ROR2 antibodies

| | IC50 ng/mL | | | ratio IC50 | |
| --- | --- | --- | --- | --- | --- |
| Antibody | anti-human Fc | human ROR2 | cynomolgus ROR2 | human ROR2/IgG | cynomolgus ROR2/IgG |
| ERR2-302 | 13.4 | 5.5 | 7.1 | 0.41 | 0.53 |
| ERR2-308 | 16.7 | 18.6 | 4.6 | 1.11 | 0.28 |
| ERR2-316 | 11.2 | 40.7 | 44 | 3.63 | 3.93 |
| ERR2-317 | 8.4 | 16.8 | 19 | 2 | 2.26 |
| XBR2-327 | 10.2 | 0.57 | 0 | 0.06 | 0 |
| XBR2-401 | 6.8 | 41.9 | 43.3 | 6.16 | 6.37 |
| ERR2-top35 | 14.3 | 46.2 | 53.1 | 3.23 | 3.71 |

Example 8. Binding Affinities of Anti-Human ROR2 Antibodies on Human and Cynomolgus ROR2

Surface plasmon resonance for the measurement of the affinities of anti-ROR2 antibodies to human ROR2 and cynomolgus ROR2 was performed on a Biacore T200 instrument (GE Healthcare). Goat α-human Fcγ-specific IgG (Jackson ImmunoResearch, 109-005-098) was covalently immobilized on a CM5 sensor chip (GE Healthcare, BR-1005-30. For affinity measurements, purified anti-human ROR2 antibodies were used. In all cases, anti-ROR2 antibodies were diluted to 7.5 µg/ml in 1×HBS-EP+ running buffer (10 mM HEPES, 150 mM NaCl, 3 mM EDTA (pH 7.4), and 0.05% (v/v) Tween P20) and captured for 60 s with a flow of 10 µl/min. Human ROR2-TwinStrep or cynomolgus ROR2-TwinStrep was diluted in running buffer using 2-fold serial dilutions ranging from 200 nM to 12.5 nM. Association and dissociation were measured at a flow of 30 µl/min for 120 s and 200 s, respectively. Calculation of association ($k_{on}$) and dissociation ($k_{off}$) rate constants was based on a 1:1 Langmuir binding model. The equilibrium dissociation constant ($K_d$) was calculated from $k_{off}/k_{on}$. Values are reported in Table 5.

TABLE 5

Binding characteristics of anti-ROR2 antibodies against human and cynomolgus ROR2 as determined by SPR

| Antigen | Antibody | $k_{on}$ (M$^{-1}$s$^{-1}$) | $k_{off}$ (s$^{-1}$) | $K_d$ (nM) |
| --- | --- | --- | --- | --- |
| Human ROR2 | XBR2-401 (mab003) | 9.78E+02 | ≤1.00E−05 | ≤10.2 |
| Cynomolgus ROR2 | XBR2-401 (mab003) | 8.71E+03 | ≤1.00E−05 | ≤1.1 |
| Human ROR2 | ERR2-302 (mab004) | 1.07E+05 | 5.60E−03 | 52.4 |
| Cynomolgus ROR2 | ERR2-302 (mab004) | 1.08E+05 | 5.27E−03 | 48.6 |
| Human ROR2 | ERR2-308 (mab037) | 1.37E+04 | 1.53E−04 | 11.2 |
| Cynomolgus ROR2 | ERR2-308 (mab037) | 2.38E+04 | 1.27E−04 | 5.4 |

Example 9. Generation of Site-Specifically Conjugated ADCs Using SMAC-Technology Sortase A enzyme. Recombinant and affinity purified Sortase A enzyme from Staphylococcus aureus was produced in E. coli as disclosed in WO2014140317A1.

Generation of glycine-modified toxins. In order to generate SMAC-Technology™ conjugated ADCs with penta-glycine-modified PNU-159682 derivative Gly$_5$-EDA-PNU (FIG. 13B) was manufactured as disclosed in WO2016102697. The identity and the purity of the penta-glycine-modified PNU toxin was confirmed by mass-spectrometry and HPLC. The Gly$_5$-modified toxin exhibited >95% purity, as determined by the single peak in the HPLC chromatogram.

Sortase-mediated antibody conjugation. The above-mentioned toxin was conjugated to anti-ROR2 antibodies as per Table 3 by incubating LPETG-tagged mAbs [10 µM] with glycine modified toxin [200 µl M] and 3 µM Sortase A in the listed conjugation buffer for 3.5 h at 25° C. The reaction was stopped by passing it through an rProtein A GraviTrap column (BioRad). Bound conjugate was eluted with 5 column volumes of elution buffer (0.1 M glycine pH 2.5, 50 nM NaCl), with 1 column volume fractions collected into tubes containing 25% v/v 1M HEPES pH 8 to neutralise the acid. Protein containing fractions were pooled and formulated in the formulation buffer of Table 7 using a ZebaSpin desalting column.

ADC analytics. DAR was assessed by Reverse Phase Chromatography performed on a Polymer Labs PLRP 2.1 mm×5 cm, 5 µm column run at 1 mL/min/80° C. with a 25 minute linear gradient between 0.05 to 0.1% TFA/H$_2$O and 0.04 to 0.1% TFA/C$_H$3CN. Samples were first reduced by incubation with DTT at pH 8.0 at 37° C. for 15 minutes. The DAR determined by Reverse Phase Chromatography is summarized in Table 6 below.

TABLE 6

Manufacturing conditions and analytical summary of ADCs manufactured in this study.

| ADC (ref.) | mAb (ref.) | Toxin | Conjugation Buffer | Formulation Buffer | DAR |
| --- | --- | --- | --- | --- | --- |
| ERR2-302-G5-PNU (adc142) | ERR2-302 (mAb004) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.5 |

TABLE 6-continued

Manufacturing conditions and analytical summary of ADCs manufactured in this study.

| ADC (ref.) | mAb (ref.) | Toxin | Conjugation Buffer | Formulation Buffer | DAR |
|---|---|---|---|---|---|
| ERR2-308-G5-PNU (adc143) | ERR2-308 (mAb037) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.5 |
| ERR2-317-G5-PNU (adc145) | ERR2-317 (mAb006) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.5 |
| XBR2-327-G5-PNU (adc146) | XBR2-327 (mAb007) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.8 |
| XBR2-401-G5-PNU (adc096) | XBR2-401 (mAb003) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.6 |
| ERR2-top35-G5-PNU (adc207) | ERR2-top35 (mAb130) | G5-PNU | 50 mM HEPES (pH 7.5), 150 mM NaCl, 1 mM CaCl$_2$ | 25 mM HEPES (pH 6.8), 150 mM NaCl | ND |
| Huluc63-G5-PNU (adc101) | Huluc63 (mAb047) | G5-PNU | 50 mM HEPES (pH 7.5), 15 mM NaCl, 5 mM CaCl$_2$ | 10 mM sodium succinate (pH 5.0), 175 mM sucrose, 0.02% (w/v) Tween 20 | 3.6 |

DAR, drug-to-antibody ratio.
ND, not determined.

Example 10. In Vitro Cytotoxicity Assays of Anti-ROR2 Antibody-Based ADCs on Wild Type EMT-6 and ROR2-Overexpressing EMT-6 Breast Cancer Cells Cytotoxicity of the anti-ROR2 ADCs of Table 5 was investigated using wild type (WT) EMT-6 and EMT-6 cells engineered to overexpress human ROR2 (from Example 1). Huluc-G5-PNU (adc101) was included as isotype control.

For this, 9.75×10$^3$ WT EMT-6 and hROR2 overexpressing EMT-6 cells per well were plated on 96-well plates (excluding edge wells, which contained water) in 75 µL DMEM supplemented with 10% by vol. FCS, 100 IU/ml Pen-Strep-Fungizone and 2 mM L-Glutamine and were grown at 37° C. in a humidified incubator at 7.5% CO$_2$ atmosphere. After 1-day incubation, each ADC was added to respective wells in an amount of 25 µL of 3.5-fold serial dilutions in growth medium (resulting in final ADC concentrations from 20 µg/mL to 0.88 ng/ml). After 4 additional days, plates were removed from the incubator and equilibrated to room temperature. After approximately 30 min, 50 µL was removed from each well, and then 50 µL of CellTiter-Glo® 2.0 Luminescent Solution (Promega, G9243) was added to each well. After shaking the plates at 750 rpm for 5 min followed by 20 min incubation without shaking, luminescence was measured on a Tecan iControl plate reader.

Curves of luminescence versus ADC concentration (ng/mL) were fitted with Graphpad Prism Software. The IC50 values, determined using the built-in "log(inhibitor) vs. response—Variable slope (four parameters)" IC$_{50}$ determination function of Prism Software, are reported in Table 7.

TABLE 7

In vitro cell killing of EMT-6 cells and EMT-6/hROR2 expressing cells by anti-ROR2 or isotype control ADCs (IC$_{50}$, ng/mL)

| ADC | WT EMT-6 | hROR2-overexpressing EMT-6 |
|---|---|---|
| ERR2-302-G5-PNU (adc142) | 2.1 × 10$^8$ | 3.2 |
| ERR2-308-G5-PNU (adc143) | 8'983 | 10.3 |
| ERR2-317-G5-PNU (adc145) | 25'205 | 6.2 |
| XBR2-401-G5-PNU (adc096) | 7'452 | 10.2 |
| XBR2-327-G5-PNU (adc146) | 11'568 | 10.2 |
| ERR2-top35-G5-PNU (adc207) | 364 | 7.2 |
| Huluc63-G5-PNU (adc101) | 3398 | 1'207 |

Figure 15:
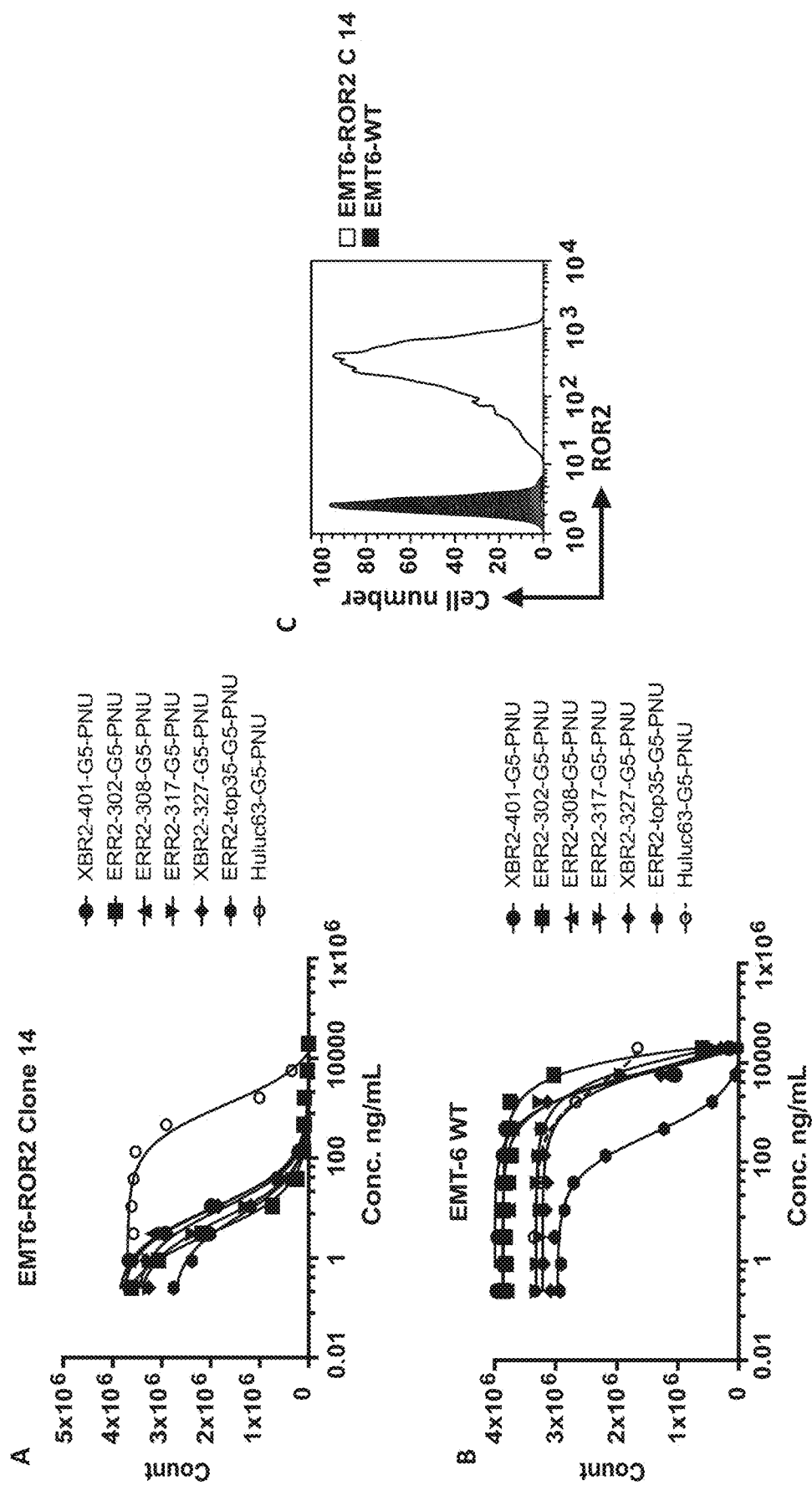
FIG. 15 shows in vitro cell killing activity of site-specifically conjugated PNU-ADCs generated with selected clones of the invention expressed as full-length chimeric rabbit-human IgG1 on (B) mouse breast cancer cell line EMT6, or (A) human ROR2 transfected EMT6 cells (clone 14). An unrelated, PNU-ADC with irrelevant specificity was used as an isotype-matched control ADC. Panel (C) shows the relative expression of hROR2 in hROR2 transfected EMT6-clone 14 versus untransfected EMT6 cells as detected by flow cytometry with a hROR2-specific antibody.

FIG. 15 shows the dose-repose curves of the in vitro cell killing assays on WT and hROR2-overexpressing EMT6 cells with the ADCs of Table 7. As per the above Table and FIG. 15, the ADCs of the invention provide specific killing dependent on ROR2 expression status.

Example 11. Functional Evaluation of CAR-T Cells Expressing Anti-hROR2 CAR Based on XBR2-401

CAR-T cells based on XBR2-401 were engineered using previously described methods (Hudecek, M., Lupo-Stanghellini, M. T., Kosasih, P. L., Sommermeyer, D., Jensen, M. C., Rader, C., and Riddell, S. R. (2013) Receptor affinity and extracellular domain modifications affect tumor recognition by ROR1-specific chimeric antigen receptor T cells. Clin. Cancer Res. 19, 3153-3164). Ex vivo expanded primary human CD8$^+$ CD62L$^+$ T cells were lentivirally transduced with XBR2-401 CARs containing CD3ζ and 4-1BB signaling domains and a short or long spacer. Transduced T cells were purified via tEGFR by FACS and their phenotype was assesed the day before functional assays. CD8+ purity varied between 97% and 99%, tEGFR expression varied between 95% and 99%. Following 72 h co-culture with ROR2-positive or ROR2-negative human breast cancer cells, CFSE-stained CD8+CD62L+ cells were analyzed by flow cytometry, revealing target-dependent proliferation of XBR2-401 (FIG. 16; upper panel). Selective cytotoxicity was measured with a luciferase-based cytotoxicity assay following 11 h of co-culture with ROR2-positive and ROR2-negative cells (FIG. 16; lower panel).

Example 12. Specificity Analysis of XBR2-401

Figure 18:
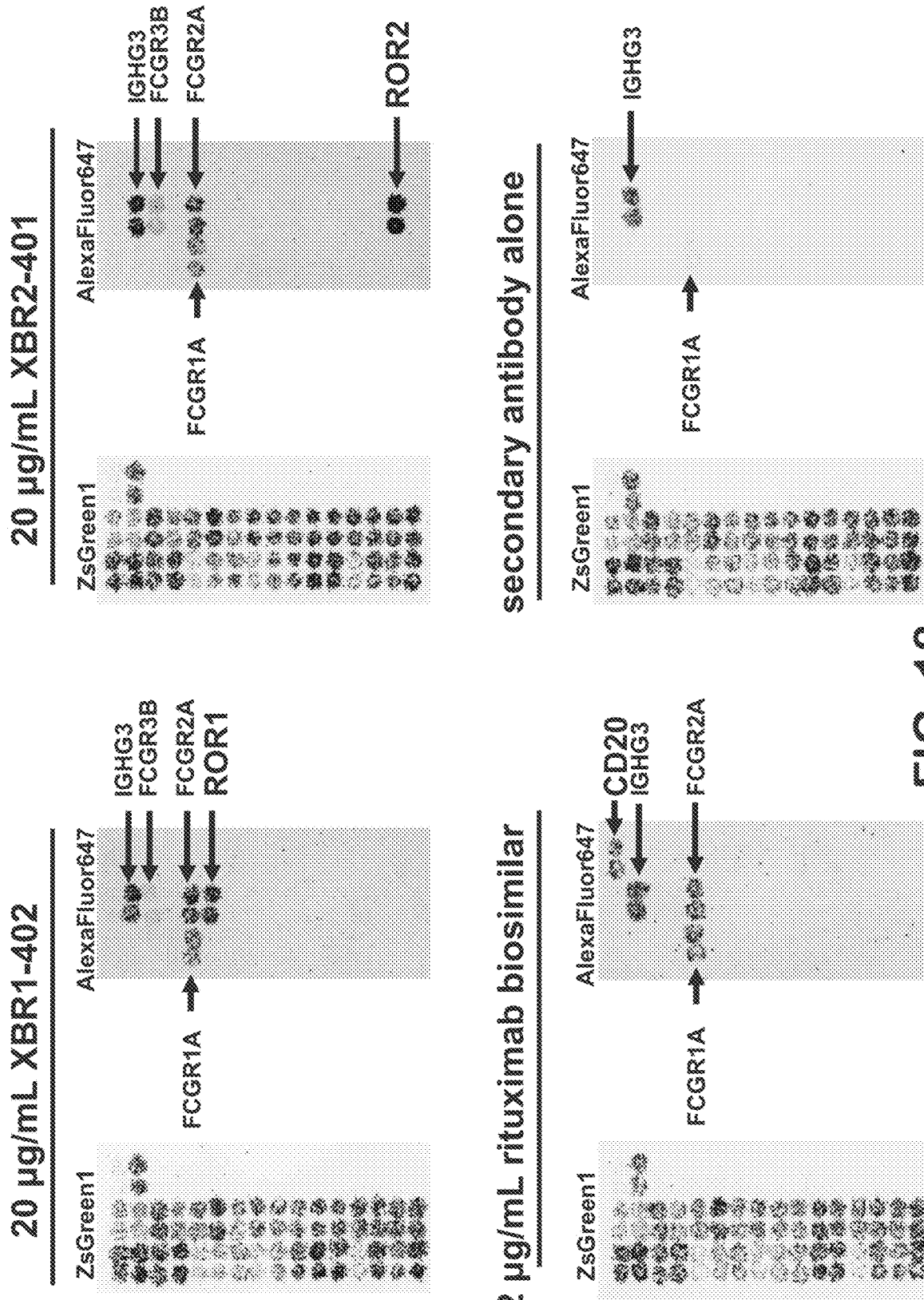
FIG. 18 shows a specificity analysis of chimeric rabbit/human anti-human ROR2 IgG1 XBR2-401 and, as a control, chimeric rabbit/human anti-human ROR1 IgG1 XBR1-402, with the Retrogenix Cell Microarray Platform. Primary binding hits from the large screen involving 4,336 human plasma membrane proteins (see FIG. 17) were combined on a single slide and stained with chimeric rabbit/human anti-human ROR2 IgG1 XBR2-401 and, as controls, chimeric rabbit/human anti-human ROR1 IgG1 XBR1-402 and a rituximab biosimilar. ZsGreen1 signals on the left indicate the expression levels of the various human membrane proteins. In addition to their respective cognate antigens (ROR2, ROR1, and CD20), the tested antibodies for ROR1 and ROR2 in IgG1 format also bind to Fcγ receptors FCGR3B (CD16B), FCGR1A (CD64A), and FCGR2A (CD32A) as expected. Staining with the secondary antibody alone detects the human IgG3 heavy chain (IGHG3) as expected.

FIG. 18 provides an overview of the Retrogenix Cell Microarray Platform. Primary screen: Purified chimeric rabbit/human IgG1 XBR2-401 targeting ROR2 and purified chimeric rabbit/human IgG1 XBR1-402 targeting ROR1 were pooled to a concentration of 2 μg/mL each. The pool was screened for binding against fixed HEK293 cells/slides expressing 4,336 human plasma membrane proteins individually (13 slide sets; n=2 slides per slide set). All transfection efficiencies exceeded the minimum threshold. An AlexaFluor647 anti-human IgG Fc detection antibody was used. Primary hits (duplicate spots) were identified by analyzing fluorescence (AlexaFluor647 and ZsGreen1) on ImageQuant. Vectors encoding all hits were sequenced to confirm their correct identities. Confirmation screen: Vectors encoding all hits, plus control vectors, were spotted in duplicate on new slides, and used to reverse transfect human HEK293 cells as before. All transfection efficiencies exceeded the minimum threshold. Identical fixed slides were treated with each of the two test antibodies (XBR2-401 and XBR1-402) individually, plus positive and negative controls (n=2 slides per treatment). Slides were analyzed as before (FIG. 18).

Some additional references cited here are listed below.

Hofer, T., W. Tangkeangsirisin, M. G. Kennedy, R. G. Mage, S. J. Raiker, K. Venkatesh, H. Lee, R. J. Giger, and C. Rader. 2007. Chimeric rabbit/human Fab and IgG specific for members of the Nogo-66 receptor family selected for species cross-reactivity with an improved phage display vector. *J Immunol Meth* 318:75-87.

Hofer, T., J. D. Thomas, T. R. Burke, Jr., and C. Rader. 2008. An engineered selenocysteine defines a unique class of antibody derivatives. *Proc Natl Acad Sci USA* 105:12451-12456.

Kwong, K. Y., S. Baskar, H. Zhang, C. L. Mackall, and C. Rader. 2008. Generation, affinity maturation, and characterization of a human anti-human NKG2D monoclonal antibody with dual antagonistic and agonistic activity. *J Mol Biot* 384:1143-1156.

Kwong, K. Y., and C. Rader. 2009. E. coli expression and purification of Fab antibody fragments. *Curr Protoc Protein Sci* Chapter 6:Unit 6 10.

McCartney-Francis, N., R. M. Skurla, Jr., R. G. Mage, and K. E. Bernstein. 1984. Kappa-chain allotypes and isotypes in the rabbit: cDNA sequences of clones encoding b9 suggest an evolutionary pathway and possible role of the interdomain disulfide bond in quantitative allotype expression. *Proc Natl Acad Sci USA* 81:1794-1798.

Popkov, M., R. G. Mage, C. B. Alexander, S. Thundivalappil, C. F. Barbas, 3rd, and C. Rader. 2003. Rabbit immune repertoires as sources for therapeutic monoclonal antibodies: the impact of kappa allotype-correlated variation in cysteine content on antibody libraries selected by phage display. *J Mol Biol* 325:325-335.

Rader, C. 2009. Generation and selection of rabbit antibody libraries by phage display. *Methods Mol Biol* 525:101-128, xiv.

Yang, J., S. Baskar, K. Y. Kwong, M. G. Kennedy, A. Wiestner, and C. Rader. 2011. Therapeutic potential and challenges of targeting receptor tyrosine kinase ROR1 with monoclonal antibodies in B-cell malignancies. *PloS One* 6:e21018.

Yang, J., and C. Rader. 2012. Cloning, expression, and purification of monoclonal antibodies in scFv-Fc format. *Methods Mol Biol* 901:209-232.

Some additional nucleotide sequences described herein are listed below.

SEQ ID NO: 129
5'-CAGTCAGTGAAGGAGTCCGAGGGAGGTCTCTTCAAGCCAACGGA
TACCCTGACACTCACCTGCACAGTCTCTGGATTCTCCCTCAGTAGCT
ATGGAGTGACCTGGGTCCGCCAGGCTCCAGGGAGCGGGCTGGAATGG
ATCGGATACATTAATACTGCTGGTAACACATACTACGCGAGCTGGGC
GAAAAGCCGGTCCACCATCACCAGGAACACCAACGAGAACACGGTGA
CTCTGAAAATGACCAGTCTGACAGCCGCGGACACGGCCACCTATTTC
TGTGCGAGAGATTGGACATCCCTTAACATCTGGGGACCAGGGACCCT
CGTCACCGTCTCTTCA-3'.

SEQ ID NO: 130
5'-CAGGAGCAGCTGGAGGAGTCCGGGGGTCGCCTGGTCACGCCTGG
GACACCCCTGACACTCACCTGCACAGTCTCTGGATTCTCCCTCAGTA
GCTACTGGATGAGCTGGGTCCGCCAGGCTCCAGGGAAGGGGCTGGAA
TGGATCGGGACCATTACGCCTGGTGGTAACACGGACTACGCGACCTG
GGCGAAAGCCCGATTCACCGTCTCCAAAACCTCGACCACGGTGGATC
TAAAAATCACCAGTCCGACAACCGAGGACACGGCCACCTATTTCTGT
GCCAGAGGGATAGGTGGTGCTGCTGACTTGTGGGGGCCAGGCACCCT
GGTCACCATCTCCTCA-3'.

SEQ ID NO: 131
5'-CAGTCAGTGAAGGAGTCCGAGGGAGGTCTCTTCAAGCCAACGGA
TAGCCTGACACTCACCTGCACAGTCTCTGGATTCTCCCTCAGTACCT
ATGGAGTGAGCTGGGTCCGCCAGGCTCCAGGGAACGGGCTGGAATGG
ATCGGGGCCATTGGTAGTAGTGGTAGCGCAAACTACGCGAGCTGGGC
GAAAGACCGATCCACCATCACCAGAAACACCAACCTGAACACGGTGA
CTCTGAAAATGACCAGTCTGACAGCCGCGGACACGGCCACCTATTTC
TGTGCGAGAGATGGTTACTATAGTAGTGGCTGGGGTCCCTACTTTAA
CATCTGGGGCCAGGCACCCTGGTCACCATCTCCTCA-3'.

SEQ ID NO: 132
5'-GACCCTATGCTGACCCAGACTCCATCCTCCACGTCTACCGCTGT
GGGAGACACAGTCACCATCAAGTGCCAGGCTAGTCAGAGCATTAGTA
GTGACTTATCCTGGTATCAGCAGAAACCAGGGCAGCGTCCCAAGCTC
CTGATCTACCAGGCATCCACTCTGGCATCTGGGGTCCCATCGCGGTT
CAAAGGCAGTGGATATGGGACAGAGTACACTCTCACCATCAGCGGCG
TGCAGCGTGAGGATGCTGCCATCTACTACTGTCTAGGTGGTTATGCT
GATGCTTCTTATCGAACTGCTTTCGGCGGAGGAACCAAGCTGGAGAT
CAAA-3'.

-continued

SEQ ID NO: 133
5'-CAAGTGCTGACCCAGACTCCATCCTCCACGTCTGCCGCTGTGGG

AGGCACAGTCACCATCAAGTGCCAGGCCAGTCAGAGCATTAGTAGTA

GCGACTTATCCTGGTATCAGCAGAAACCAGGGCAGCCTCCCAAGCTC

CTGATCTATGCTACATCCTATCTGGCATCTGGAGTCCCATCGCGGTT

CAAAGGCAGTGGATCTGGGACAGAGTACACTCTCACCATCAGCGGCG

TGCAGCGTGAGGATGCTGCCACCTACTACTGTCTAGGTGGTTATCCT

AATACTTCTTACCGGTCTGCTTTCGGCGGAGGGACCAAGGTGGAGAT

CAAA-3'.

SEQ ID NO: 134
5'-TCCTTCGTGCTGACTCAGCCAGCCTCAGTGCAGGTGAACTTGGG

ACAGACGGTCTCCCTCACATGCACTGCAGATACACTGAGCAGAAGTT

ATGCTTCCTGGTACCAGCAGAAGCCAGGCCAGGCCCCTGTGCTGCTC

ATCTACAGGGATACCAGTCGGCCCTCAGGGGTCCCTGACCGCTTCTC

TGGCTCCAGCTCAGGGAACACGGCCACCCTGACCATCAGTGGGGCCC

AGGCTGGGGACGAGGCTGACTACTATTGTGCTACAAGCGGTGGCAGT

GGCAGCAACCCTCAGTATGTGTTCGGCGGAGGGACCCAGCTGACCGT

CACAGGC-3'.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

We claim:

1. An antibody, an antibody-based binding protein or an antibody fragment that specifically binds to the extracellular domain of human receptor tyrosine kinase-like orphan receptor 2 (ROR2), comprising heavy chain CDR1-3 sequences and light chain CDR1-3 sequences that are that are respectively identical to (i) SEQ ID NOs:28-30 and SEQ ID NOs:64-66, (ii) SEQ ID NOs:31-33 and SEQ ID NOs:67-69, (iii) SEQ ID NOs:34-36 and SEQ ID NOs:70-72, (iv) SEQ ID NOs:37-39 and SEQ ID NOs:73-75, (v) SEQ ID NOs:40-42 and SEQ ID NOs:76-78, (vi) SEQ ID NOs:43-45 and SEQ ID NOs:79-81, (vii) SEQ ID NOs:46-48 and SEQ ID NOs:82-84, (viii) SEQ ID NOs:49-51 and SEQ ID NOs:85-87, (ix) SEQ ID NOs:52-54 and SEQ ID NOs:88-90, (x) SEQ ID NOs:55-57 and SEQ ID NOs:91-93, or (xi) SEQ ID NOs:58-60 and SEQ ID NOs:94-96.

2. The antibody, antibody-based binding protein or antibody fragment of claim 1, comprising a heavy chain variable region sequence and a light chain variable region sequence that are at least 95% identical, respectively, to (i) SEQ ID NO:2 and SEQ ID NO:14; (ii) SEQ ID NO:3 and SEQ ID NO:15; (iii) SEQ ID NO:4 and SEQ ID NO:16; (iv) SEQ ID NO:5 and SEQ ID NO:17; (v) SEQ ID NO:6 and SEQ ID NO:18; (vi) SEQ ID NO:7 and SEQ ID NO:19; (vii) SEQ ID NO:8 and SEQ ID NO:20; (viii) SEQ ID NO:9 and SEQ ID NO:21; (ix) SEQ ID NO:10 and SEQ ID NO:22; (x) SEQ ID NO:11 and SEQ ID NO:23; or (xi) SEQ ID NO:12 and SEQ ID NO:24.

3. The antibody, antibody-based binding protein or antibody fragment of claim 1, comprising a heavy chain variable region sequence and a light chain variable region sequence that are respectively shown in (i) SEQ ID NO:2 and SEQ ID NO:14; (ii) SEQ ID NO:3 and SEQ ID NO:15; (iii) SEQ ID NO:4 and SEQ ID NO:16; (iv) SEQ ID NO:5 and SEQ ID NO:17; (v) SEQ ID NO:6 and SEQ ID NO:18; (vi) SEQ ID NO:7 and SEQ ID NO:19; (vii) SEQ ID NO:8 and SEQ ID NO:20; (viii) SEQ ID NO:9 and SEQ ID NO:21; (ix) SEQ ID NO:10 and SEQ ID NO:22; (x) SEQ ID NO:11 and SEQ ID NO:23; or (xi) SEQ ID NO:12 and SEQ ID NO:24.

4. The antibody, antibody-based binding protein or antibody fragment of claim 1, wherein the antibody or antibody fragment is chimeric or humanized.

5. An antibody drug conjugate (ADC), comprising the antibody or antibody fragment of claim 1 and at least one cytotoxic agent.

6. The antibody, antibody-based binding protein or antibody fragment of claim 1, wherein the antibody or antibody fragment is IgA1, IgA2, IgD, IgE, IgG1, IgG2, IgG3, IgG4, synthetic IgG, IgM, F(ab)2, Fv, scFv, IgGACH2, F(ab')2, scFv2CH3, Fab, VL, VH, scFv4, scFv3, scFv2, dsFv, Fv, scFv-Fc, (scFv)2, a non-depleting IgG, a diabody, or a bivalent antibody.

7. The antibody, antibody-based binding protein or antibody fragment of claim 1, which is conjugated to a synthetic molecule.

8. The antibody, antibody-based binding protein or antibody fragment of claim 7, wherein the synthetic molecule is a cytotoxic agent, a label, a therapeutic radioisotope, or a liposome.

9. The antibody or antigen-binding fragment of claim 8, wherein the cytotoxic agent is selected from a small molecular weight toxin, or a peptide toxin, or a protein toxin.

10. A pharmaceutical composition comprising (1) a therapeutically effective amount of (a) an antibody, antibody-based binding protein or antibody fragment of claim 1, and (2) a pharmaceutically acceptable carrier.

* * * * *